(12) United States Patent
Diwu et al.

(10) Patent No.: US 9,810,700 B1
(45) Date of Patent: Nov. 7, 2017

(54) FLUOROGENIC CALCIUM ION INDICATORS AND METHODS OF USING THE SAME

(71) Applicant: AAT Bioquest, Inc., Sunnyvale, CA (US)

(72) Inventors: Zhenjun Diwu, Sunnyvale, CA (US); Haitao Guo, Sunnyvale, CA (US); Ruogu Peng, San Jose, CA (US); Qin Zhao, Sunnyvale, CA (US); Jinfang Liao, Foster City, CA (US); Feng Liu, San Jose, CA (US)

(73) Assignee: AAT Bioquest, Inc., Sunnyvale, CA (US)

( * ) Notice: Subject to any disclaimer, the term of this patent is extended or adjusted under 35 U.S.C. 154(b) by 0 days.

(21) Appl. No.: 15/610,184

(22) Filed: May 31, 2017

(51) Int. Cl.
| | |
|---|---|
| C07D 311/90 | (2006.01) |
| G01N 33/84 | (2006.01) |
| C07D 493/10 | (2006.01) |
| C07C 229/22 | (2006.01) |
| C07F 5/02 | (2006.01) |
| C07D 307/94 | (2006.01) |
| G01N 33/58 | (2006.01) |

(52) U.S. Cl.
CPC ........... *G01N 33/84* (2013.01); *C07C 229/22* (2013.01); *C07D 307/94* (2013.01); *C07D 311/90* (2013.01); *C07D 493/10* (2013.01); *C07F 5/022* (2013.01); *G01N 33/582* (2013.01)

(58) Field of Classification Search
CPC ........ C07D 311/90; C07D 307/94; C09B 5/00
See application file for complete search history.

(56) References Cited

U.S. PATENT DOCUMENTS

| | | | |
|---|---|---|---|
| 4,146,712 A | 3/1979 | Loew | |
| 4,200,753 A | 4/1980 | Henry | |
| 4,603,209 A | 7/1986 | Tsien et al. | |
| 4,849,362 A | 7/1989 | DeMarinis et al. | |
| 4,921,827 A | 5/1990 | Ali et al. | |
| 4,945,171 A | 7/1990 | Haugland et al. | |
| 5,049,673 A | 9/1991 | Tsien et al. | |
| 5,380,836 A | 1/1995 | Rogart | |
| 5,436,128 A | 7/1995 | Harpold et al. | |
| 5,453,517 A | 9/1995 | Kuhn et al. | |
| 5,459,276 A | 10/1995 | Kuhn et al. | |
| 5,501,980 A | 3/1996 | Katerinopoulos et al. | |
| 5,516,911 A | 5/1996 | London et al. | |
| 5,696,157 A | 12/1997 | Wang et al. | |
| 5,773,227 A | 6/1998 | Kuhn et al. | |
| 6,057,114 A | 5/2000 | Akong et al. | |
| 6,162,931 A | 12/2000 | Gee et al. | |
| 6,340,750 B1 | 1/2002 | Burgess et al. | |
| 6,420,183 B1 | 7/2002 | Krahn et al. | |
| 6,566,508 B2 | 5/2003 | Bentsen et al. | |
| 8,779,165 B2 | 7/2014 | Diwu et al. | |
| 8,927,224 B2 | 1/2015 | Diwu et al. | |
| 9,097,730 B2 | 8/2015 | Diwu et al. | |
| 9,279,817 B2 | 3/2016 | Diwu et al. | |
| 9,346,778 B2 * | 5/2016 | Diwu | G01N 33/84 |
| 2002/0164616 A1 | 11/2002 | Martin et al. | |
| 2008/0254498 A1 | 10/2008 | Diwu et al. | |

FOREIGN PATENT DOCUMENTS

WO    WO201606638 A1    1/2016

OTHER PUBLICATIONS

Boens et al., Fluorescent indicators based on BODIPY, Chem Soc Rev. Feb. 7, 2012;41(3):1130-72.
Chen et al., Design and synthesis of a fluorescent reporter of protein kinase activity, J Am Chem Soc. Apr. 17, 2002;124(15)3840-1.
Grynkiewcz et al., A new generation of Ca2+ indicators with greatly improved fluorescence properties, J Biol Chem. Mar. 25, 1985;260(6):3440-50.
Koide et al., Evolution of group 14 rhodamines as platforms for near-infrared fluorescence probes utilizing photoinduced electron transfer, ACS Chem Biol. Jun. 17, 2011;6(6):600-8.
Kolmakov et al., A Versatile Route to Red-Emitting Carbopyronine Dyes for Optical Microscopy and Nanoscopy, European Journal of Organic Chemistry, 2010, 2010(19)3593-3610.
Mishra et al., Cyanines during the 1990s: A Review, Chem Rev. Jun. 14, 2000;100(6):1973-2012.
Nagant et al., Effect of pluronic acid F-127 on the toxicity towards eukaryotic cells of CSA-13, a cationic steroid analogue of antimicrobial peptides, J Appl Microbial. Jun. 2012;112(6):1173-83.
Robbins et al., The history and future of probenecid, Cardiovasc Toxicol. Mar. 2012;12(1):1-9.
Sednev et al., Carborhodol: a new hybrid fluorophore obtained by combination of fluorescein and carbopyronine dye cores, Bioconjug Chem. Apr. 17, 2013;24(4):690-700.
Thivierge et al., Fluorescent Proton Sensors Based on Energy Transfer, J. Org. Chem., 2011, 76 (13), pp. 5219-5228.
Tsien, New Calcium Indicators and Buffers with High Selectivity against Magnesium and Protons: Design, Synthesis, and Properties of Prototype Structures, Biochemistry, 1980, 19 (11), pp. 2396-2404.

(Continued)

*Primary Examiner* — Michael G Hartley
*Assistant Examiner* — Jagadishwar Samala
(74) *Attorney, Agent, or Firm* — Glenn J. Foulds; Bozicevic, Field & Francis LLP

(57) ABSTRACT

The present disclosure provides fluorogenic compounds useful for preparing fluorescent calcium ion indicators, the fluorescent indicators themselves, and the use of the fluorescent indicators in methods of detection, discrimination and quantification of metal ions. The subject fluorogenic compounds and fluorescent ion indicators can include a chelating group based on a 2-aminophenoxyethylene glycol 2-aminoethyl ether, N,N,N',N'-tetraacetic acid (PEGTA) moiety or precursor thereof where the phenyl group of the PEGTA is substituted with or fused with a fluorophore moiety of interest. The subject methods find use in the detection of intracellular calcium ions. Also provided are kits for use in practicing the subject methods.

20 Claims, 6 Drawing Sheets

(56) References Cited

OTHER PUBLICATIONS

Urano et al., Evolution of fluorescein as a platform for finely tunable fluorescence probes, J Am Chem Soc. Apr. 6, 2005;127(13):4888-94.

Zhou et al., Chemoselective Alteration of Fluorophore Scaffolds as a Strategy for the Development of Ratiometric Chemodosimeters, Angew Chem Int Ed Engl. Apr. 3, 2017;56(15):4197-4200.

* cited by examiner

FLUOROGENIC CALCIUM ION INDICATORS AND METHODS OF USING THE SAME

INTRODUCTION

Metal ions play important roles in many biological systems. Cells utilize metal ions for a wide variety of functions, such as regulating enzyme activities, protein structures, cellular signaling, as catalysts, as templates for polymer formation and as regulatory elements for gene transcription. Metal ions can also have a deleterious effect when present in excess of bodily requirements or capacity to excrete. A large number of natural and synthetic materials are known to selectively or non-selectively bind to or chelate metal ions. Ion chelators are commonly used in solution for in vivo control of ionic concentrations and detoxification of excess metals, and as in vitro buffers. Ion chelators can also be used as optical indicators of ions when bound to a fluorophore, and may be useful in the analysis of cellular microenvironments or dynamic properties of proteins, membranes and nucleic acids. Among metal ions, $Ca^{2+}$ ion plays an important role in many biological events, and thus the cellular $Ca^{2+}$ determination is an important biological application. BAPTA-incorporated fluorescent dyes have been used for the optical detection of calcium ion by monitoring their fluorescence intensity changes or wavelength shifts. These sensitive and convenient calcium probes include Indo-1, Fura-2, Fluo-3, Fluo-4. Fluo-8, Rhod-2, Rhod-4 and X-Rhod, etc. These fluorescent indicators utilizing a polycarboxylate BAPTA chelator have been predominantly used for intracellular calcium detections. Fluorescent indicators for metal ions, including indicators that find use in measuring intracellular calcium are of interest.

SUMMARY

The present disclosure provides fluorogenic compounds useful for preparing fluorescent calcium ion indicators, the fluorescent indicators themselves, and the use of the fluorescent indicators in methods of detection, discrimination and quantification of metal ions. The subject fluorogenic compounds and fluorescent ion indicators can include a chelating group based on a 2-aminophenoxyethylene glycol 2-aminoethyl ether, N,N,N',N'-tetraacetic acid (PEGTA) moiety or precursor thereof where the phenyl group of the PEGTA is substituted with or fused with a fluorophore moiety of interest. The subject methods find use in the detection of intracellular calcium ions. Also provided are kits for use in practicing the subject methods.

DEFINITIONS

Figure 1A:
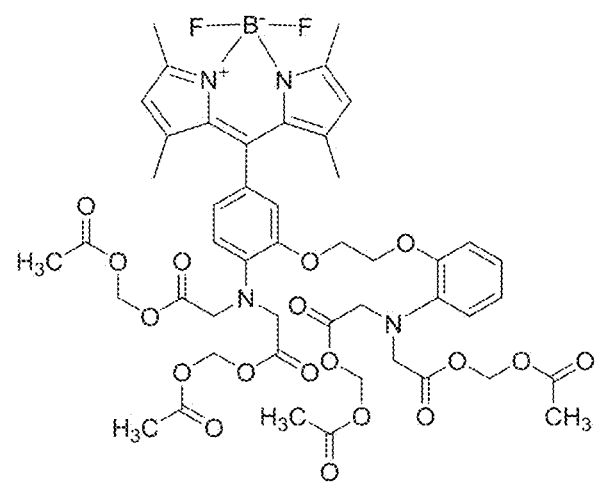
FIG. 1A to FIG. 1C show the chemical structures of BAPTA Bodipy AM (FIG. 1A), BAPTA fluorescein AM (FIG. 1B), Fluo-3 AM (R=Cl) and Fluo-4 AM (R=F) (FIG. 1C).
Figure 1B:
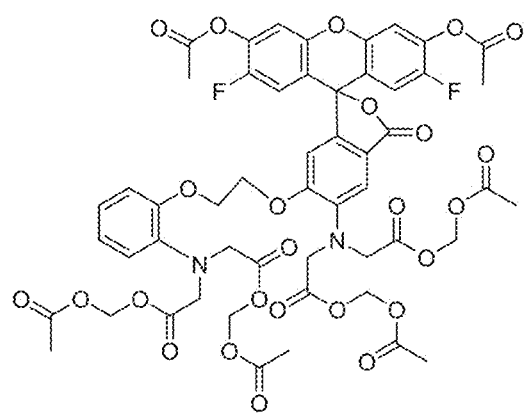
Figure 1C:
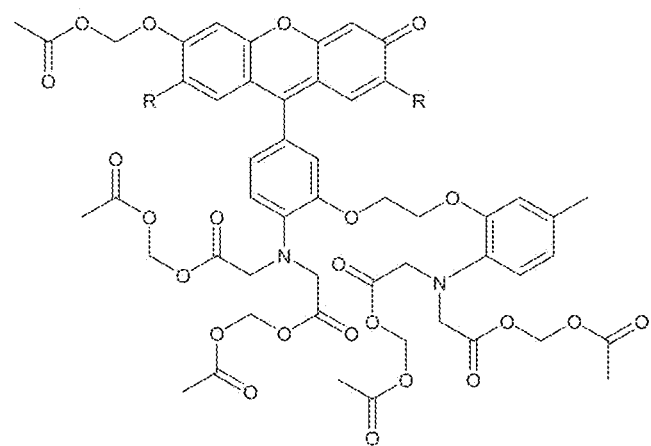

The following definitions are set forth to illustrate and define the meaning and scope of the various terms used to describe the invention herein.

The term "organic substituent", as used herein, refers to a carbon-containing organic radical that incorporates straight, branched chain or cyclic radicals having up to 50 carbons, unless the chain length or ring size is limited thereto. The organic substituent may include one or more elements of unsaturation, such as carbon-carbon double or triple bonds. Organic substituents may include alkyl, alkylene, alkenyl, alkenylene and alkynyl moieties, among others.

The term "alkyl," as used herein, by itself or as part of another group, refers to straight, branched chain or cyclic radicals having up to 50 carbons, unless the chain length or ring size is limited thereto, such as methyl, ethyl, propyl, cyclopropanyl, isopropyl, butyl, t-butyl, isobutyl, pentyl, hexyl, cyclohexyl, isohexyl, heptyl, 4,4-dimethylpentyl, octyl, 2,2,4-trimethylpentyl, nonyl, and decyl, among others.

The term "alkylene," as employed herein, by itself or as part of another group, refers to straight, branched chain or cyclic divalent radicals having up to 50 carbons, unless the chain length or ring size is limited thereto. Typical examples include methylene (—$CH_2$—), ethylene (—$CH_2CH_2$—), propylene, butylene, pentylene, hexylene, heptylene, octylene, nonylene, and decylene, among others.

The term "alkenyl," as used herein, by itself or as part of another group, means a straight, branched chain or cyclic radical having 2-50 carbon atoms and one or more carbon-carbon double bonds, unless the chain length or ring size is limited thereto, such as ethenyl, I-propenyl, 2-propenyl, 2-methyl-1-propenyl, 1-butenyl, and 2-butenyl, among others. The alkenyl chain may be 2 to 10 carbon atoms in length. Alternatively, the alkenyl chain may be 2 to 4 carbon atoms in length.

The term "alkenylene," as used herein, by itself or as part of another group, means straight branched chain or cyclic divalent radical having 2-50 carbon atoms, unless the chain length or ring size is limited thereto, said straight, branched chain or cyclic radical containing at least one carbon-carbon double bond. Typical examples include ethenylene (—CH=CH—), propenylene (—CH=$CHCH_2$— and —$CH_2$CH=CH—), n-butenylene, and 3-methyl-2-pentenylene, hexenylene, heptenylene, octenylene, nonenylene, and decenylene, among others.

The term "alkynyl," as used herein, by itself or as part of another group, means a straight, branched chain or cyclic radical of 2-50 carbon atoms, unless the chain length or ring size is limited thereto, having at least one carbon-carbon triple bond between two of the carbon atoms in the chain, such as acetylenyl, 1-propynyl, and 2-propynyl, among others. The alkynyl chain may be 2 to 10 carbon atoms in length. Alternatively, the alkynyl chain may be from 2 to 4 carbon atoms in length.

The term "alkynylene" as used herein, by itself or as part of another group, means a straight, branched chain or cyclic divalent radical having 2-50 carbon atoms, unless the chain length or ring size is limited thereto, that contains at least one carbon-carbon triple bond. Typical examples include ethynylene (—C≡C—), propynylene (—C≡$CCH_2$— and —$CH_2$C≡C—), n-butynylene, 4-methyl-2-pentynylene, 1-butynylene, 2-butynylene, 3-butynylene, 4-butynylene, pentynylene, hexynylene, heptynylene, octynylene, nonynylene, and decynylene, among others.

The term "alkoxy" as used herein, by itself or as part of another group, refers to any of the above radicals linked via an oxygen atom. Typical examples include methoxy, ethoxy, isopropyloxy, sec-butyloxy, n-butyloxy, t-butyloxy, n-pentyloxy, 2-methylbutyloxy, 3-methylbutyloxy, n-hexyloxy, and 2-ethylbutyloxy, among others. Alkoxy also may include PEG groups (—$OCH_2CH_2O$—) or alkyl moieties that contain more than one oxygen atom.

The term "aryl," as employed herein, by itself or as part of another group, refers to an aryl or aromatic ring system containing 1 to 4 unsaturated rings (each ring containing 6 conjugated carbon atoms and no heteroatoms) that are optionally fused to each other or bonded to each other by carbon-carbon single bonds, that is optionally further substituted as described below. Examples of aryl ring systems include, but are not limited to, substituted or unsubstituted derivatives of phenyl, biphenyl, o-, m-, or p-terphenyl, 1-naphthyl, 2-naphthyl, 1-, 2-, or 9-anthryl, 1-, 2-, 3-, 4-, or 9-phenanthrenyl and 1-, 2- or 4-pyrenyl. Aryl substituents may include phenyl, substituted phenyl, naphthyl or substituted naphthyl.

The term "heteroaryl," as employed herein, by itself or as part of another group, refers to groups having 5 to 14 ring atoms; 6, 10 or 14 π electrons shared in a cyclic array, and containing carbon atoms and 1, 2, 3, or 4 oxygen, nitrogen or sulfur heteroatoms (where examples of heteroaryl groups are: thienyl, benzo[b]thienyl, naphtho[2,3-b]thienyl, thianthrenyl, furyl, pyranyl, isobenzofuranyl, benzoxazolyl, chromenyl, xanthenyl, phenoxathiinyl, 2H-pyrrolyl, pyrrolyl, imidazolyl, pyrazolyl, pyridyl, pyrazinyl, pyrimidinyl, pyridazinyl, indolizinyl, isoindolyl, 3H-indolyl, indolyl, indazolyl, purinyl, 4H-quinolizinyl, isoquinolyl, quinolyl, phthalazinyl, naphthyridinyl, quinazolinyl, cinnolinyl, pteridinyl, carbazolyl, phenanthridinyl, acridinyl, perimidinyl, phenanthrolinyl, phenazinyl, isothiazolyl, phenothiazinyl, isoxazolyl, furazanyl, phenoxazinyl, and tetrazolyl groups).

Any aryl or heteroaryl ring system is unsubstituted or optionally and independently substituted by any synthetically accessible and chemically stable combination of substituents, such as H, halogen, cyano, sulfo, alkali or ammonium salt of sulfo, nitro, carboxy, alkyl, perfluoroalkyl, alkoxy, alkylthio, amino, monoalkylamino, dialkylamino or alkylamido, the alkyl portions of which having 18 or fewer carbons.

The terms "halogen" or "halo" as employed herein, by itself or as part of another group, refers to chlorine, bromine, fluorine or iodine.

The terms "AM ester" or "AM" as employed herein, by itself or as part of another group, refers to an acetoxymethyl ester of a carboxylic acid or a phenol.

The terms "amino" or "amine" include $NH_2$, "monoalkylamine" or "monoalkylamino," and "dialkylamine" or "dialkylamino". The terms "monoalkylamine" and "monoalkylamino," "dialkylamine" and "dialkylamino as employed herein, by itself or as part of another group, refers to the group $NH_2$ where one hydrogen has been replaced by an alkyl group, as defined above.

The terms "dialkylamine" and "dialkylamino" as employed herein, by itself or as part of another group, refers to the group $NH_2$ where both hydrogens have been replaced by alkyl groups, as defined above.

The term "hydroxyalkyl," as employed herein, by itself or as part of another group, refers to an alkyl group where one or more hydrogens thereof are substituted by one or more hydroxyl moieties.

The term "haloalkyl," as employed herein, by itself or as part of another group, refers to an alkyl group where one or more hydrogens thereof are substituted by one or more halo moieties. Typical examples include chloromethyl, fluoromethyl, difluoromethyl, trifluoromethyl, trichloroethyl, trifluoroethyl, fluoropropyl, and bromobutyl, among others.

The term "haloalkenyl," as employed herein, by itself or as part of another group, refers to an alkenyl group where one or more hydrogens thereof are substituted by one or more halo moieties.

The term "haloalkynyl," as employed herein, by itself or as part of another group, refers to an alkynyl group where one or more hydrogens thereof are substituted by one or more halo moieties.

The term "carboxyalkyl," as employed herein, by itself or as part of another group, refers to an alkyl group where one or more hydrogens thereof are substituted by one or more carboxylic acid moieties.

The term "heteroatom" as used herein, by itself or as part of another group, means an oxygen atom ("O"), a sulfur atom ("S") or a nitrogen atom ("N"). It will be recognized that when the heteroatom is nitrogen, it may form an $NR_1R_2$ moiety, where $R_1$ and $R_2$ are, independently from one another, hydrogen or alkyl, or together with the nitrogen to which they are bound, form a saturated or unsaturated 5-, 6-, or 7-membered ring.

Unless explicitly indicated otherwise, the organic substituent groups described herein may be unsubstituted or substituted. In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =$NR^{70}$, =N—$OR^{70}$, =$N_2$ or =S) on saturated carbon atoms in the specified group or radical are, unless otherwise specified, —$R^{60}$, halo, =O, —$OR^{70}$, —$SR^{70}$, —$NR^{80}R^{80}$, trihalomethyl, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2^-M^+$, —$OSO_2OR^{70}$, —$P(O)(O^-)_2(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$C(O)O^-M^+$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)O^-M^+$, —$OC(O)OR^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each M is a counter ion with a net single positive charge. Each $M^+$ may independently be, for example, an alkali ion, such as $K^+$, $Na^+$, $Li_+$; an ammonium ion, such as $^+N(R^6)_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —$NR^{80}R^{80}$ is meant to include —$NH_2$, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3^{-2}(M^+)_2$, —$P(O)(OR^{70})O^-M^+$, —$P(O)(OR^{70})_2$, —$C(O)R^{70}$, —$C(S)R^{70}$, —$C(NR^{70})R^{70}$, —$CO_2^-M^+$, —$CO_2R^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OCO_2^-M^+$, —$OCO_2R^{70}$, —$OC(S)OR^{70}$, —$NR^{70}C(O)R^{70}$, —$NR^{70}C(S)R^{70}$, —$NR^{70}CO_2^-M^+$, —$NR^{70}CO_2R^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined, provided that in case of substituted alkene or alkyne, the substituents are not —$O^-M^+$, —$OR^{70}$, —$SR^{70}$, or —$S^-M^+$.

In addition to the groups disclosed with respect to the individual terms herein, substituent groups for hydrogens on nitrogen atoms in "substituted" heteroalkyl and cycloheteroalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR$, —$P(O)(O^-)_2(M^+)_2$, —$P(O)(OR^{70})O^-M^+$, —$P(O)(OR^{70})(OR^{70})$, —$C(O)R^{70}$, —$C(S)R^{70}$, —$C(NR^{70})R^{70}$, —$C(O)OR^{70}$, —$C(S)OR^{70}$, —$C(O)NR^{80}R^{80}$, —$C(NR^{70})NR^{80}R^{80}$, —$OC(O)R^{70}$, —$OC(S)R^{70}$, —$OC(O)OR^{70}$, —$OC(S)OR^{70}$, —$NR^{70}C(O)R^{70}$, —$NR C(S)R^{70}$, —$NR^{70}C(O)OR^{70}$, —$NR^{70}C(S)OR^{70}$, —$NR^{70}C(O)NR^{80}R^{80}$, —$NR^{70}C(NR^{70})R^{70}$ and —$NR^{70}C(NR^{70})NR^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, compounds arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The terms "chelator", "chelate", "chelating group", "ionophore", or "ionophoric moiety" as used herein, by itself or as part of another group, refers to a chemical moiety that binds to, or complexes with, one or more metal ions, such as lithium, calcium, sodium, magnesium, potassium, and/or other biologically important metal ions. The binding affinity of a chelator for a particular metal ion can be determined by measuring the dissociation constant between that chelator and that ion. Chelators may include one or more chemical moieties that bind to, or complex with, a cation or anion. Examples of suitable chelators include 2-aminophenylethylene glycol-bis(β-aminoethyl ether)-N,N,N',N'-tetraacetic acid (PEGTA), 1,2-bis(2-aminophenoxy)ethane-N,N,N',N'-tetraacetic acid (BAPTA), bipyridyl (bipy); terpyridyl (terpy); ethylenediaminetetraacetic acid (EDTA); crown ethers; aza-crown ethers; succinic acid; citric acid; salicylic acids; histidines; imidazoles; ethyleneglycol-bis-(beta-aminoethyl ether) N,N'-tetraacetic acid (EGTA); nitroloacetic acid; acetylacetonate (acac); sulfate, dithiocarbamates; carboxylates; alkyldiamines; ethylenediamine (en); diethylenetriamine (dien); nitrate; nitro; nitroso; glyme; diglyme; bis(acetylacetonate)ethylenediamine (acacen); 1,4,7,10-tetraazacyclododecanetetraacetic acid (DOTA), 1,4,7,10-tetraazacyclododecane-1,4,7-triacetic acid (DO3A), 1-oxa-4,7,10-triazacyclododecane-triacetic acid (OTTA), 1,4,7-triazacyclononanetriacetic acid (NOTA), 1,4,8,11-tetraazacyclotetra-decanetetraacetic acid (TETA), DOTA-N-(2-aminoethyl) amide; DOTA-N-(2-aminophenethyl) amide; and 1,4,8,11-tetraazacyclotetradecane, among others.

The term "EGTA" or "ethylene glycol-bis(β-aminoethyl ether)-N,N,N',N'-tetraacetic acid" as used herein, by itself or as part of another group, refers to the following structure or its derivatives, such as esters, amides, carbamates and so on:

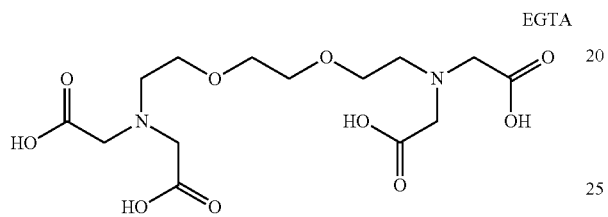

EGTA

The term "BAPTA" or "1,2-bis(2-aminophenoxy)ethane-N,N,N',N'-tetraacetic acid" as used herein, by itself or as part of another group, refers to the following ring structure or its derivatives, such as esters, amides, carbamates and so on:

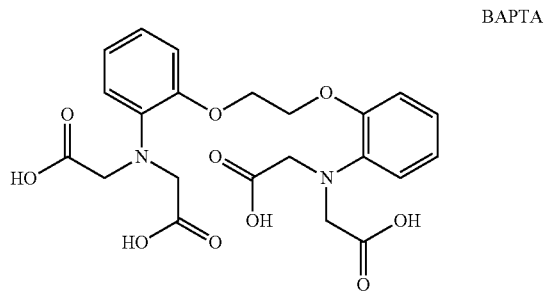 [SMILES: O=C(O)CN(CC(=O)O)c1ccccc1OCCOc1ccccc1N(CC(=O)O)CC(=O)O]

BAPTA

The term "PEGTA" or "2-aminophenoxyethylene glycol 2-aminoethyl ether, N,N,N',N'-tetraacetic acid" as used herein, by itself or as part of another group, refers to the following ring structure or its derivatives, such as esters, amides, carbamates and so on:

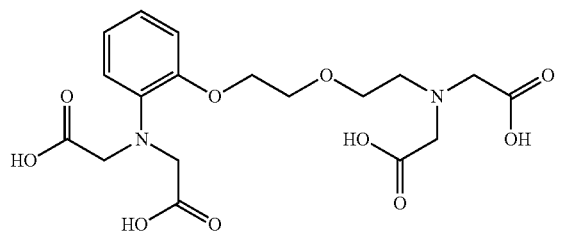

PEGTA

The term "fluorophore or fluorophore moiety" as used herein, by itself or as part of another group, means a molecule or a portion of a molecule which exhibits fluorescence. By fluorescence is meant that the molecule or portion of a molecule can absorb excitation energy having a given wavelength and emit energy at a different wavelength. The intensity and wavelength of the emitted energy depend on the fluorophore, the chemical environment of the fluorophore, and the specific excitation energy used. Exemplary fluorophores include, but are not limited to, fluoresceins, rhodamines, coumarins, oxazines, cyanines, pyrenes, and other polycyclic aromatic molecules.

The term "xanthene", or "xanthene derivative", as used herein, by itself or as part of another group, means any compounds or substituents that contain one or more of the following fused ring structures or its derivatives:

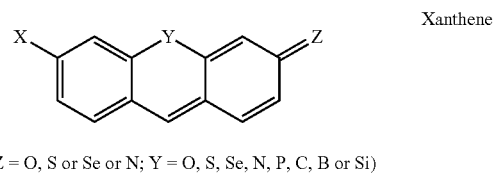

Xanthene (X, Z = O, S or Se or N; Y = O, S, Se, N, P, C, B or Si)

The term "fluorescein" as used herein, by itself or as part of another group, means any compounds or substituents that contain one or more of the following fused ring structures or its derivatives:

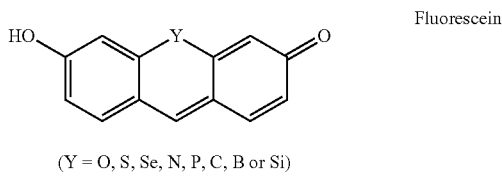

Fluorescein (Y = O, S, Se, N, P, C, B or Si)

The term "rhodamine" as used herein, by itself or as part of another group, means any compounds or substituents that contain one or more of the following fused ring structures or its derivatives:

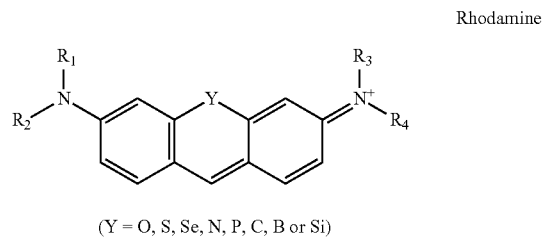

Rhodamine (Y = O, S, Se, N, P, C, B or Si)

The term "substituted," as used herein, refers to the formal replacement of a hydrogen on a chemical moiety or functional group with an alternative radical. Where a compound, chemical moiety or functional group is described as substituted, the alternative radical substituent moiety is generally selected from the group consisting of hydroxy, oxo, nitro, trifluoromethyl, halogen, alkoxy, alkylenedioxy, aminoalkyl, aminoalkoxy, amino, monoalkylamino, dialkylamino, alkylcarbonylamino, alkoxycarbonylamino, alkoxycarbonyl, carboxy, hydroxyalkoxy, alkoxyalkoxy, mono-alkylaminoalkoxy, dialkylaminoalkoxymono(carboxyalkyl)amino, bis(carboxy-alkyl)amino, alkoxycarbonyl, alkynylcarbonyl, alkylsulfonyl, alkenylsulfonyl, alkynylsulfonyl, arylsulfonyl, alkylsulfinyl, alkylsulfonamido, arylsulfonamido, carboxyalkoxy, carboxyalkyl, carboxyalkylamino, cyano, trifluoromethoxy, perfluoroethoxy, guanidine, amidino, oxyguanidino, alkylimino, formylimino, acyl nitrile, acyl azide, acetyl azide, dichlorotriazene, isothiocyante, sulfonyl halide, sulfosuccinimidyl ester, isocyante, acyl halide, aldehyde, haloacetamide, maleimido, aziridinyl, alkylthio (disulfide), acrylo, haloalkylcarbonyl, boronate, hydrazide, semicarbazide, carbohydrazide, arylalkyl, heteroarylalkyl, cycloalkylalkyl, cycloalkenylalkyl, cycloheteroalkylalkyl, and cycloheteroalkenylalkyl.

The term "indicator" refers to a dye or dye moiety that exhibits a change in a spectroscopic property in the presence of a target analyte. The term "indicator compound" refers to the compounds of the present disclosure, specifically to those compounds having utility as fluorescent metal ion indicators, as well as their acylated or otherwise protected fluorogenic precursor compounds, such as the acetoxymethyl ester derivatives suitable for adding to samples containing biological cells.

The term "fluorogenic" refers to a dye, dye moiety or compound that is capable of demonstrating a change in fluorescence upon interaction with a target analyte of interest. The fluorogenic dye can have a first fluorescent form in the absence of target analyte and is capable of being converted to a second fluorescent form in the presence of target analyte. The conversion of the fluorogenic dye to a fluorescent dye product (i.e., conversion from a first to a second fluorescent state, e.g., as described herein) can be achieved via direct or indirect action of the target analyte on the fluorogenic dye. The first and second fluorescent form of the dye refers to chemical or physical forms of the dye compounds. The term "chemical form" refers to the chemical structure of a molecule, where the first and second forms of a fluorogenic dye involve distinct chemical structures which can have different spectral properties. The term "physical form" is meant to encompass a variety of different physical forms of a molecule having identical chemical structure, but having different spectral properties due to the molecule being in a, e.g., different electronic state, a different steric state, or a different physical environment, such as an analyte bound form or an unbound form.

In certain instances, the fluorogenic dye is substantially non-fluorescent in the absence of target analyte. In some cases, the fluorogenic dye is ratiometric. The term "ratiometric" refers to a fluorescent indicator for a target analyte where the intensity of the fluorescence emission signal is proportional to the amount of target analyte that is present. As such, measurement of the fluorescence emission signal can be used to quantitate the amount of target analyte that is present in the composition.

The term "screening" refers to the testing and/or evaluation of a multiplicity of molecules or compounds for a selected property or therapeutic utility. Screening is typically a repetitive, or iterative process. A multiplicity of candidate molecules may be screened for their ability to bind to a target molecule which is capable of denaturing and/or unfolding. For example, a multiplicity of candidate molecules may be evaluated for their ability to bind to a target molecule (e.g., a protein receptor) in a thermal shift assay. If none of a selected subset of molecules from the multiplicity of candidate molecules (for example, a combinatorial library) binds to the target molecule, then a different subset may be tested for binding in the thermal shift assay.

The term "high-throughput", as used herein, encompasses screening activity in which human intervention is minimized, and automation is maximized. For example, high-throughput screening may include any of a variety of automated processes, including for example the automation of pipetting, mixing, and/or heating, the software-controlled generation of thermal unfolding information, and the software-controlled comparisons of thermal unfolding information. Alternatively, a high-throughput method is one in which hundreds of compounds can be screened per 24 hour period by a single individual operating a single suitable apparatus.

DETAILED DESCRIPTION

The present disclosure is directed to fluorescent dyes useful for preparing fluorescent metal ion indicators, the fluorescent indicators themselves, and the use of the fluorescent indicators for the detection, discrimination and quantification of metal cations. The present application provides a family of fluorescent dyes that find use in a variety of applications as fluorogenic calcium ion indicators. The indicators can include a fluorophore and a PEGTA ionophore, and find use in the detection, discrimination and quantification of calcium cations in a variety of applications. The fluorescent indicators of the present disclosure demonstrate greatly improved water solubility, little cytotoxicity and unexpectedly better cellular responses compared to BAPTA-based calcium ion indicators.

Before certain embodiments are described in greater detail, it is to be understood that this invention is not limited to certain embodiments described, as such may, of course, vary. It is also to be understood that the terminology used herein is for the purpose of describing certain embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

In further describing the various aspects of the invention, the structures of members of the various indicator compounds are described first in greater detail, followed by a description of methods of use and methods of screening and applications in which the indicator compounds find use.

Fluorogenic Ion Indicator Compounds

The present disclosure provides fluorescent ion indicator compounds that include a chelating group based on a 2-aminophenoxyethylene glycol 2-aminoethyl ether, N,N,N',N'-tetraacetic acid (PEGTA) moiety or precursor where the phenyl group of the PEGTA is substituted with group(s) that provides for the incorporation of a fluorophore moiety into the indicator. In some cases, the phenyl group of the PEGTA can be part of the fluorophore moiety and contribute to the spectroscopic properties of the compound. In certain cases, the substituted phenyl group is a fused benzo ring that becomes part of a fluorophore moiety of the resulting compound. In some cases, the substituted phenyl group is linked to the fluorophore moiety via a single covalent bond, where the phenyl group can be conjugated to the fluorophore moiety.

Fluorophore moieties of interest which can be adapted for incorporation into the subject compounds, include but are not limited to, a fluorescein, a rhodamine, a cyanine, a bodipy, a squaraine, a pyrene, an indole, an furan, a pyrylium, a thiazole, quinoline, a fluorene, an acridine, an acridone, a phenazine, a phenanthroline, a carbazole, a pyridine, a pyrimidine, a purine, a quinolizine, a quinoxaline, naphthyridine, phthalazine, pyridopyrimidine, pteridine, chromone, thiophene, oxadiazole, oxatriazole, thiadiazole, pyranopyrrole, furopyridine, oxazolopyridine, benzoisothiazole, thienopyridine, phenoxazine, phenothiazine, a ruthenium complex, an europium complex, a terbium complex, a perylenediimide, a coumarin, an oxazine, an oxazole, a phthalocyanine, derivatives thereof, and precursors thereof. Any convenient fluorogenic precursor forms of the fluorophore moieties described herein can find use in the subject compounds.

In some cases, the substituted phenyl group is connected to a fluorophore moiety that is a xanthene group via a fused 5-membered lactone ring (e.g., as described herein). Any convenient fluorophore moieties, or portions thereof, can be adapted for incorporation into the subject compounds, e.g., via fusion or substitution of the phenyl ring of the subject PEGTA chelating group.

The subject PEGTA-based calcium indicators can have unexpected and desirable water solubility. The subject PEGTA-based calcium indicators can have drastically improved cellular retention when used in intracellular metal ion assays. Thus, in some cases, the subject PEGTA-based fluorescent indicators can be utilized in assays (e.g., calcium ion assays) without the need for an organic anion transporter inhibitor such as probenecid, or a detergent (e.g., Pluronic F-127). Organic anion transporter inhibitor such as probenecid are used to prevent fast cell leakage of dyes from the cell, Detergents are commonly used to disperse the calcium indicator AM esters in cell culture medium, but can severely affect cell growth and have other cytotoxic effects on cells. As such, the subject indicator compounds can be cell-permeable in their precursor fluorogenic form, and also have high cell retention and/or low cell toxicity.

In some embodiments, the subject compounds are described by Formula 1:

Formula 1

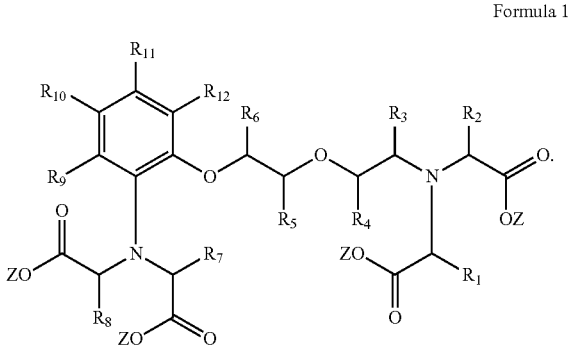

In this embodiment, substituents $R_1$-$R_8$ are independently H, an alkyl, an aryl or a heteroaryl; $R_9$-$R_{12}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl, a heteroaryl, a heterocycle or a fluorophore moiety; Z is H, a counter cation, or an alkyl having 1-10 carbons provided that at least one of $R_9$-$R_{12}$ is a fluorophore or two of $R_9$-$R_{12}$ can form a fluorophore by condensing to the PEGTA benzene ring. In certain instances of formula 1, at least one of $R_9$-$R_{12}$ is a fluorophore moiety or any two of $R_9$-$R_{12}$ are cyclically linked together with ring A to define a fluorophore moiety comprising a benzo-fused aryl, heteroaryl or heterocycle ring.

In some embodiments of formula 1, one of $R_9$-$R_{12}$ is a fluorophore moiety. In certain embodiments of formula 1, two adjacent $R_9$-$R_{12}$ groups are cyclically linked and together with ring A form or define a fused aryl, heteroaryl or heterocycle ring of the fluorophore moiety. As such, ring A can be a part of the resulting fluorophore of the subject compound via electronic linkage or conjugation. In certain embodiments of formula 1, $R^{10}$ or $R^{11}$ is a fluorophore moiety. In certain embodiments of formula 1, $R^{10}$ and $R^{11}$ are cyclically linked and together with ring A form or define a fused aryl, heteroaryl or heterocycle ring of the fluorophore moiety. As such, the fused ring defined by $R^{10}$ and $R^{11}$ can be optionally further substituted with any convenient groups of a fluorophore moiety (e.g., as described herein). In certain embodiments of formula 1, one of $R^{10}$ or $R^{11}$ is a xanthene group (e.g., of a fluorescein or rhodamine dye) and the other of $R^{10}$ or $R^{11}$ is a carboxy, wherein the carboxy group and the adjacent carbon atom of the xanthene are optionally cyclically linked to form a 5-membered lactone ring. In certain embodiments, the compound can include a lactone precursor of a xanthene type dye, or a fluorescent carboxylic acid open form of the dye.

In some embodiments, substituents $R_1$-$R_8$ are independently H, an alkyl, an aryl or a heteroaryl; $R_9$-$R_{12}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; Z is an acyloxymethyl having 1-10 carbons provided that at least one of $R_9$-$R_{12}$ is a fluorophore or can form a fused fluorophore by condensing to the PEGTA benzene ring at any two of $R_9$-$R_{12}$.

In some embodiments, substituents $R_1$-$R_8$ are independently H or alkyl; $R_9$-$R_{12}$ are independently H, halogen, an alkyl, carboxy, acyloxymethylcarbonyl, an alkoxy, an aryloxy, thiol, an alkylthiol, an arylthiol, azido, nitro, cyano, an amino, hydroxy, a carbonyl, a boronyl, an aryl or a heteroaryl; Z is acetoxymethyl provided that at least one of $R_9$-$R_{12}$ is a fluorophore or form a fluorophore by condensing to the PEGTA benzene ring.

In some embodiments, substituents $R_1$-$R_8$ are independently H or methyl; $R_9$-$R_{12}$ are independently H, halogen, an alkyl, carboxy, acyloxymethylcarbonyl, alkoxy, azido aryl or heteroaryl; Z is acetoxymethyl provided that at least one of $R_9$-$R_{12}$ is a fluorophore or form a fluorophore by condensing to the PEGTA benzene ring.

In some embodiments, substituents $R_1$-$R_8$ are independently H or methyl; $R_9$-$R_{12}$ are independently H, halogen, an alkyl, carboxy, acyloxymethylcarbonyl, alkoxy, nitro, aryl or heteroaryl; Z is acetoxymethyl provided that at least one of $R_9$-$R_{12}$ is a fluorescein, a rhodamine, a cyanine, a bodipy, a squaraine, a pyrene, an indole, an furan, a pyrylium, a thiazole, quinoline, a fluorene, an acridine, an acridone, a phenazine, a phenanthroline, a carbazole, a pyridine, a pyrimidine, a purine, a quinolizine, a quinoxaline, naphthyridine, phthalazine, pyridopyrimidine, pteridine, chromone, thiophene, oxadiazole, oxatriazole, thiadiazole, pyranopyrrole, furopyridine, oxazolopyridine, benzoisothiazole, thienopyridine, phenoxazine, phenothiazine, a ruthenium complex, an europium complex, a terbium complex, a perylenediimide, a coumarin, an oxazine, an oxazole or a phthalocyanine.

In some embodiments of formula 1, any two of $R_9$-$R_{12}$ are cyclically linked together with ring A to define a fluorophore moiety comprising a benzo-fused aryl, heteroaryl or heterocycle ring, where the resulting fluorophore moiety is selected from a quinoline dye, an indole dye, an furan dye, an oxazine dye, an oxazole dye, a thiazole dye, an oxadiazole dye, an oxatriazole dye, a thiadiazole dye, a benzoisothiazole dye, a fluorene dye, a phenoxazine dye, a phenothiazine dye and a coumarin dye.

In some embodiments, substituents $R_1$-$R_8$ are H; $R_9$-$R_{12}$ are independently H, fluoro, an alkyl, carboxy, an acyloxymethylcarbonyl, an alkoxy, azido, an aryl or a heteroaryl; Z is acetoxymethyl provided that at least one of $R_9$-$R_{12}$ is a fluorescein, a rhodamine, a bodipy, an indole, a furan, a coumarin, an oxazine, or an oxazole.

In some embodiments of formula 1, the subject compounds may be described by Formula 2:

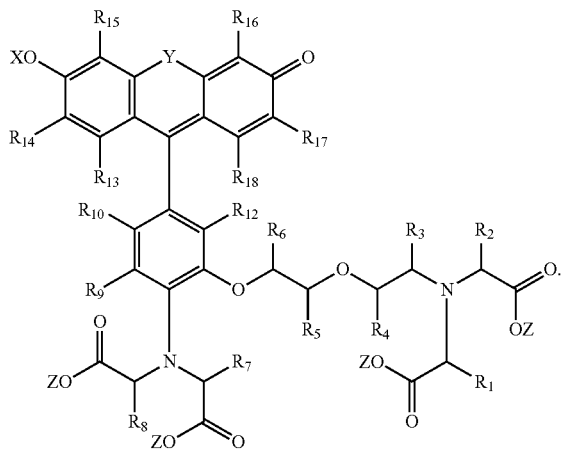

Formula 2

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; X and Z are independently H, a counter cation, an acyl, an acyloxymethyl, or an alkyl having 1-10 carbons. Y is O, S, S=O, O=S=O, B—OH, B(OH)$_2$, B—O$R_{25}$, $R_{25}$O—B—O$R_{26}$, Si(OH)$_2$, $R_{25}$OSiO$R_{26}$, N—$R_{25}$, P—$R_{25}$, O=P—$R_{25}$, $R_{25}$—C—$R_{26}$, or $R_{25}$—Si—$R_{16}$ wherein $R_{25}$ and $R_{26}$ are independently H, an alkyl, an aryl or a heteroaryl. Preferably X and Z are independently an acyl or an acyloxymethyl having 1-10 carbons. More preferably X and Z are independently acetyl or acetoxymethyl.

In some embodiments, Formula 2 has substituents wherein $R_1$-$R_8$ are independently H or alkyl; $R_9$-$R_{18}$ are independently H, an alkyl, chloro, fluoro, carboxy, an acyloxymethylcarbonyl, an alkoxy, cyano, an amino or hydroxy; X and Z are independently H, a metal ion, an ammonium, an acyl, an acyloxymethyl, or an alkyl having 1-10 carbons. Y is O, N—$R_{25}$, O=P—$R_{25}$, $R_{25}$—C—$R^{26}$, or $R_{25}$—Si—$R_{26}$ wherein $R_{25}$ and $R_{26}$ are independently H, an alkyl, an aryl or a heteroaryl.

In some embodiments, Formula 2 has substituents wherein $R_1$-$R_8$ are independently H or methyl; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; X and Z are independently H, a metal ion, an ammonium, an acyl, an acyoxymethyl or an alkyl having 1-10 carbons. Y is O, N—$R_{25}$, O=P—$R_{25}$, $R_{25}$—C—$R^{26}$, or $R_{25}$—Si—$R_{26}$ wherein $R_{25}$ and $R_{26}$ are independently H, an alkyl, an aryl or a heteroaryl.

In some embodiments, Formula 2 has substituents wherein $R_1$-$R_8$ are H; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; X is acetyl or acetoxymethyl; Y is O, O=P—$R_{25}$, $R_{25}$—C—$R_{26}$, or $R_{25}$—Si—$R_{26}$ wherein $R_{25}$ and $R_{26}$ are an alkyl; Z is acetoxymethyl.

In some embodiments, the subject compounds may be described by Formula 3:

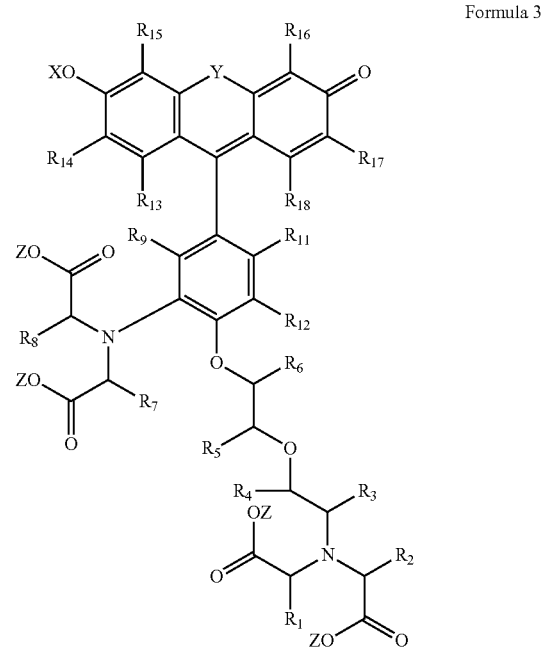

Formula 3

In some embodiments, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; X and Z are independently H, a counter cation, an acyl, an acyloxymethyl, or an alkyl having 1-10 carbons. O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl. In certain cases, X and Z are independently an acyl or an acyloxymethyl having 1-10 carbons. In certain cases, X and Z are independently acetyl or acetoxymethyl.

In some embodiments, Formula 3 has substituents wherein $R_1$-$R_8$ are independently H or alkyl; $R_9$-$R_{18}$ are independently H, an alkyl, chloro, fluoro, carboxy, an acyloxymethylcarbonyl, an alkoxy, cyano, an amino or hydroxy; X and Z are independently H, a metal ion, an ammonium, an acyl, an acyloxymethyl, or an alkyl having 1-10 carbons. Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

In some embodiments. Formula 3 has substituents wherein $R_1$-$R_8$ are independently H or methyl; $R_9$-$R_{12}$ are independently H, alkyl, chloro, fluoro, an acyloxymethylcarbonyl, an alkoxy or nitro, $R_{13}$-$R_{18}$ are independently H, chloro or fluoro; X and Z are independently H, a metal ion, an ammonium, an acyl, an acyoxymethyl or an alkyl having 1-10 carbons. Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

In some embodiments, Formula 3 has substituents wherein $R_1$-$R_8$ are H; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are an alkyl; Z is acetoxymethyl.

In some embodiments, the subject compounds may be described by Formula 4:

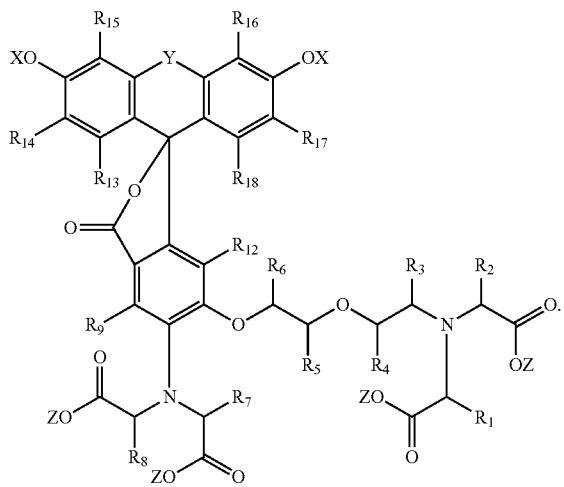

Formula 4

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; X and Z are independently an acyl or an acyloxymethyl having 1-10 carbons; Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl. Preferably X and Z are acetyl or acetoxymethyl.

In some embodiments, Formula 4 has substituents wherein $R_1$-$R_8$ are independently H or alkyl; $R_9$-$R_{18}$ are independently H, alkyl, chloro, fluoro, an alkoxy, azido, nitro, cyano, amino or hydroxy; X is acetyl or acetoxymethyl; Y is O, O=P—R$_{25}$, R$_{25}$—C—R$_{26}$, or R$_{25}$—Si—R$_2$ wherein R$_{25}$ and R$_{26}$ are an alkyl; Z is acetoxymethyl.

In some embodiments, Formula 4 has substituents wherein $R_1$-$R_8$ are independently H or methyl; $R_9$-$R_{12}$ are independently H, alkyl, chloro, fluoro, an alkoxy or nitro; $R_{13}$-$R_{18}$ are independently H, chloro or fluoro; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are an alkyl; Z is acetoxymethyl.

In some embodiments, Formula 4 has substituents wherein $R_1$-$R_8$ are H; $R_9$-$R_{12}$ are independently H, alkyl, chloro, fluoro, alkoxy or nitro; $R_{13}$-$R_{18}$ are independently H, chloro or fluoro; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are methyl, ethyl, propyl or butyl; Z is acetoxymethyl.

In some embodiments, the subject compounds may be described by Formula 5:

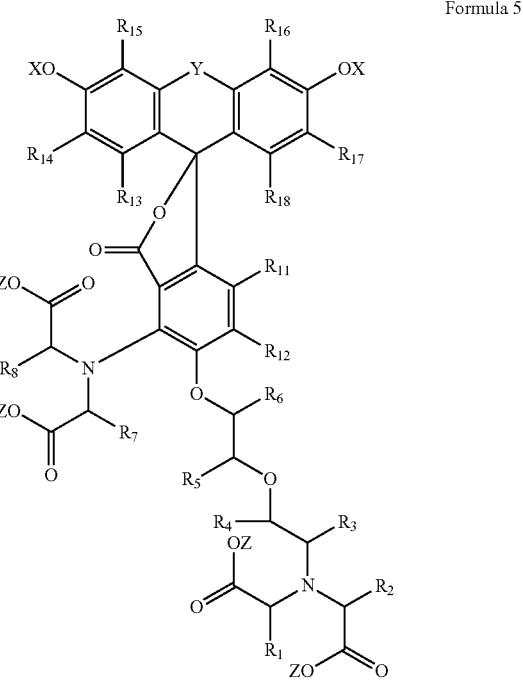

Formula 5

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; X and Z are independently an acyl or an acyloxymethyl having 1-10 carbons; Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R—C—R$_{26}$, or R$_{25}$—Si—R$_{26}$ wherein R$_{25}$ and R$_{26}$ are independently H, an alkyl, an aryl or a heteroaryl. Preferably X and Z are acetyl or acetoxymethyl.

In some embodiments, Formula 5 has substituents wherein $R_1$-$R_8$ are independently H or alkyl; $R_9$-$R_{18}$ are independently H, alkyl, chloro, fluoro, an alkoxy, azido, nitro, cyano, amino or hydroxy; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are an alkyl; Z is acetoxymethyl.

In some embodiments, Formula 5 has substituents wherein $R_1$-$R_8$ are independently H or methyl; $R_9$-$R_{12}$ are independently H, alkyl, chloro, fluoro, an alkoxy or nitro; $R_{13}$-$R_{18}$ are independently H, chloro or fluoro; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are an alkyl; Z is acetoxymethyl.

In some embodiments, Formula 5 has substituents wherein $R_1$-$R_8$ are H; $R_9$-$R_{12}$ are independently H, alkyl, chloro, fluoro, alkoxy or nitro; $R_{13}$-$R_{18}$ are independently H, chloro or fluoro; X is acetyl or acetoxymethyl; Y is O, O=P—R$_{25}$, R$_{25}$—C—R$_{26}$, or R$_{25}$—Si—R$_{26}$ wherein R$_{25}$ and R$_{26}$ are methyl, ethyl, propyl or butyl; Z is acetoxymethyl.

In some embodiments, the subject compounds may be described by Formula 6:

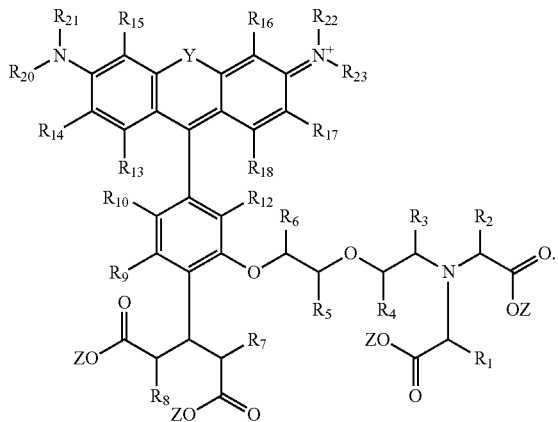

Formula 6

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; $R_{20}$-$R_{23}$ are independently H, an alkyl, or a cycloalkyl, or a heterocycle wherein R$_{20}$ and R$_{14}$, R$_{21}$ and R$_{15}$, R$_{20}$ and R$_{21}$, R$_{22}$ and R$_{16}$, R$_{23}$ and R$_{17}$, or R$_{22}$ and R$_{23}$ combine to form a 3-8 membered ring; Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl; Z is H, a counter cation, an acyl, an acyloxymethyl, or an alkyl having 1-10 carbons. In certain cases, Z is an acyloxymethyl having 1-10 carbons. In certain cases, Z is acetoxymethyl.

In some embodiments, Formula 6 has substituents wherein $R_1$-$R_8$ are independently H or alkyl; $R_9$-$R_{18}$ are independently H, an alkyl, chloro, fluoro, carboxy, an acyloxymethylcarbonyl, an alkoxy, cyano, an amino or hydroxy; $R_{20}$-$R_{23}$ are independently H, an alkyl, or a cycloalkyl, or a heterocycle wherein R$_{20}$ and R$_{14}$, R$_{21}$ and R$_{15}$, R$_{20}$ and R$_{21}$, R$_{22}$ and R$_{16}$, R$_{23}$ and R$_{17}$, or R$_{22}$ and R$_{23}$ combine to form a 5- or 6-membered ring; Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl; Z is H, a metal ion, an ammonium, an acyl, an acyloxymethyl, or an alkyl having 1-10 carbons.

In some embodiments, Formula 6 has substituents wherein $R_1$-$R_8$ are independently H or methyl; $R_9$-$R_{12}$ are independently H, alkyl, chloro, fluoro, an acyloxymethylcarbonyl, an alkoxy or nitro; $R_1$-$R_{18}$ are independently H, chloro or fluoro; $R_{20}$-$R_{23}$ are independently H, an alkyl, or a cycloalkyl, or a heterocycle wherein R$_{20}$ and R$_{14}$, R$_{21}$ and R$_{15}$, R$_{20}$ and R$_{21}$, R$_{22}$ and R$_{16}$, R$_{23}$ and R$_{17}$, or R$_{22}$ and R$_{23}$ combine to form a 5- or 6-membered ring; Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl; Z is H, a metal ion, an ammonium, an acyl, an acyoxymethyl or an alkyl having 1-10 carbons.

In some embodiments, Formula 6 has substituents wherein $R_1$-$R_8$ are H; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; $R_{20}$-$R_{23}$ are independently H, an alkyl, or a cycloalkyl, or a heterocycle wherein R$_{20}$ and R$_{14}$, R$_{21}$ and R$_{15}$, R$_{20}$ and R$_{21}$, R$_{22}$ and R$_{16}$, R$_{23}$ and R$_{17}$, or R$_{22}$ and R$_{23}$ combine to form a 5- or 6-membered ring; Y is O, O=P—R$_{25}$, R$_{25}$—C—R$_{26}$, or R$_{25}$—Si—R$_{26}$ wherein R$_{25}$ and R$_{26}$ are an alkyl; Z is acetoxymethyl.

In some embodiments, the subject compounds may be described by Formula 7:

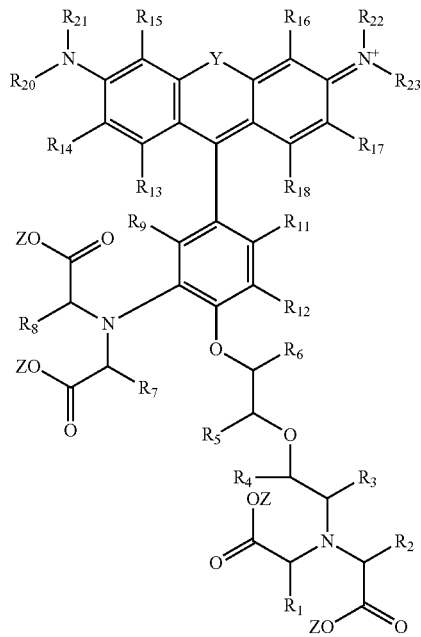

Formula 7

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 3-8 membered ring; Y is O, S, S—O, O=S=O, B—OH, B(OH)$_2$, B—OR$_{25}$, $R_{25}$O—B—OR$_{26}$, Si(OH)$_2$, $R_{25}$OSiOR$_{26}$, N—$R_{25}$, P—$R_{25}$, O=P—$R_{25}$, $R_{25}$—C—$R_{26}$, or $R_{25}$—Si—$R_{26}$ wherein $R_{25}$ and $R_{26}$ are independently H, an alkyl, an aryl or a heteroaryl; Z is H, a counter cation, an acyl, an acyloxymethyl, or an alkyl having 1-10 carbons. In certain cases. Z is an acyloxymethyl having 1-10 carbons. In certain cases, Z is acetoxymethyl.

In some embodiments, Formula 7 has substituents wherein $R_1$-$R_8$ are independently H or alkyl; $R_9$-$R_{18}$ are independently H, an alkyl, chloro, fluoro, carboxy, an acyloxymethylcarbonyl, an alkoxy, cyano, an amino or hydroxy; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring; Y is O, N—$R_{25}$, O=P—$R_{25}$, $R_{25}$—C—$R_{26}$, or $R_{25}$—Si—$R_{26}$ wherein $R_{25}$ and $R_{26}$ are independently H, an alkyl, an aryl or a heteroaryl; Z is H, a metal ion, an ammonium, an acyl, an acyloxymethyl, or an alkyl having 1-10 carbons.

In some embodiments, Formula 7 has substituents wherein $R_1$-$R_8$ are independently H or methyl; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring; Y is O, N—$R_{25}$, O=P—$R_{25}$, $R_{25}$—C—$R_{26}$, or $R_{25}$—Si—$R_{26}$ wherein $R_{25}$ and $R_{26}$ are independently H, an alkyl, an aryl or a heteroaryl; Z is H, a metal ion, an ammonium, an acyl, an acyoxymethyl or an alkyl having 1-10 carbons.

In some embodiments, Formula 7 has substituents wherein $R_1$-$R_8$ are H; $R_9$-$R_{12}$ are independently H, alkyl, chloro, fluoro, an acyloxymethylcarbonyl, an alkoxy or nitro; $R_{13}$-$R_{18}$ are independently H, chloro or fluoro; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring; Y is O, O=P—$R_{25}$. $R_{25}$—C—$R_{26}$, or $R_{25}$—Si—$R_{26}$ wherein $R_{25}$ and $R_{26}$ are an alkyl; Z is acetoxymethyl.

In some embodiments, the subject compounds may be described by Formula 8:

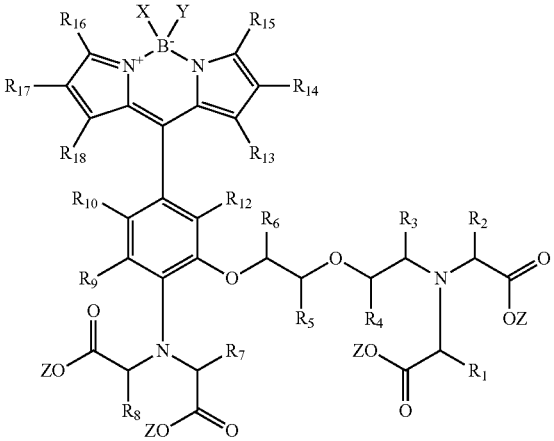

Formula 8

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; $R_{13}$ and $R_{14}$, $R_{14}$ and $R_{15}$, $R_{17}$ and $R_{18}$, or $R_{16}$ and $R_{17}$ may combine to form a 5- or 6-membered aromatic ring or a heteroaryl ring; X and Y are independently F, an alkynyl, an alkoxy or an aryloxy; Z is H, a counter cation, an acyl, an acyloxymethyl, or an alkyl having 1-10 carbons. In certain cases, Z is an acyloxymethyl having 1-10 carbons. In certain cases, Z is acetoxymethyl.

In some embodiments, Formula 8 has substituents wherein $R_1$-$R_8$ are independently H or alkyl; $R_9$-$R_{18}$ are independently H, an alkyl, chloro, fluoro, an acyloxymethylcarbonyl, an alkoxy, cyano, aryl or a heteroaryl; $R_{13}$ and $R_{14}$, $R_{14}$ and $R_{15}$, $R_{17}$ and $R_{18}$, or $R_{16}$ and $R_{17}$ may combine to form a 5- or 6-membered aromatic ring or a heteroaryl ring; X and Y are F or an alkoxy; Z is an acyloxymethyl having 1-10 carbons.

In some embodiments, Formula 8 has substituents wherein $R_1$-$R_8$ are H; $R_9$-$R_{18}$ are independently H, an alkyl, chloro, fluoro, an acyloxymethylcarbonyl, an alkoxy, cyano, aryl or a heteroaryl; $R_{13}$ and $R_{14}$, $R_{14}$ and $R_{13}$, $R_{17}$ and $R_{18}$, or $R_{16}$ and $R_{17}$ may combine to form a 5- or 6-membered aromatic ring or a heteroaryl ring; X and Y are F; Z is acetoxymethyl.

In some embodiments, the subject compounds may be described by Formula 9:

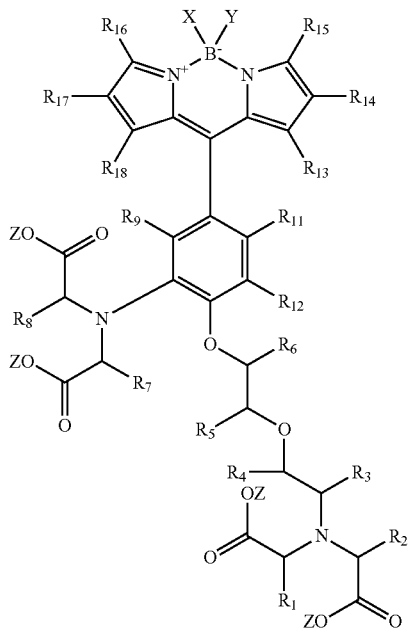

Formula 9

In this embodiment, substituents $R_1$-$R_8$ are independently H, an alkyl, an aryl or a heteroaryl; $R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; $R_{13}$ and $R_{14}$, $R_{14}$ and $R_{15}$, $R_{17}$ and $R_{18}$, or $R_{16}$ and $R_{17}$ may combine to form a 5- or 6-membered aromatic ring or a heteroaryl ring; X and Y are independently F, an alkynyl, an alkoxy or an aryloxy; Z is H, a counter cation, an acyl, an acyloxymethyl, or an alkyl having 1-10 carbons. In certain cases Z is an acyloxymethyl having 1-10 carbons. In certain cases, Z is acetoxymethyl.

In some embodiments. Formula 9 has substituents wherein $R_1$-$R_8$ are independently H or alkyl; $R_9$-$R_{18}$ are independently H, an alkyl, chloro, fluoro, an acyloxymethylcarbonyl, an alkoxy, cyano, aryl or a heteroaryl; $R_{13}$ and $R_{14}$, $R_{14}$ and $R_{15}$, $R_{17}$ and $R_{18}$, or $R_{16}$ and $R_{17}$ may combine to form a 5- or 6-membered aromatic ring or a heteroaryl ring; X and Y are F or an alkoxy; Z is an acyloxymethyl having 1-10 carbons.

In some embodiments, Formula 9 has substituents wherein $R_1$-$R_8$ are H; $R_9$-$R_{18}$ are independently H, an alkyl, chloro, fluoro, an acyloxymethylcarbonyl, an alkoxy, cyano, aryl or a heteroaryl; $R_1$ and $R_{14}$, $R_{14}$ and $R_{15}$, $R_{17}$ and $R_{18}$, or $R_{16}$ and $R_{17}$ may combine to form a 5- or 6-membered aromatic ring or a heteroaryl ring; X and Y are F; Z is acetoxymethyl.

In some embodiments of Formulae 1-9, the subject compound has the structure of a compound of Table 2. In some embodiments of Formulae 1-9, the subject compound has the structure of a compound of Table 2, or an ester thereof (e.g., an AM ester, such as a tetra or penta-AM ester, e.g., of compound 19), or a salt thereof. The structures of several exemplary compounds of interest are provided in Table 2.

TABLE 2

Exemplary compounds of the present disclosure:

| Compound# | Structure |
|---|---|
| 19 | 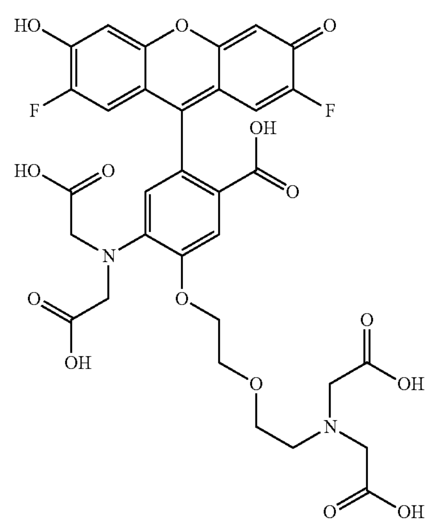 [SMILES: O=C(O)CN(CCOCCOc1cc(C(=O)O)c(-c2c3cc(F)c(=O)cc-3oc3cc(O)c(F)cc23)cc1N(CC(=O)O)CC(=O)O)CC(=O)O] |

TABLE 2-continued
Exemplary compounds of the present disclosure:
| Compound# | Structure |
|---|---|
| 20 | 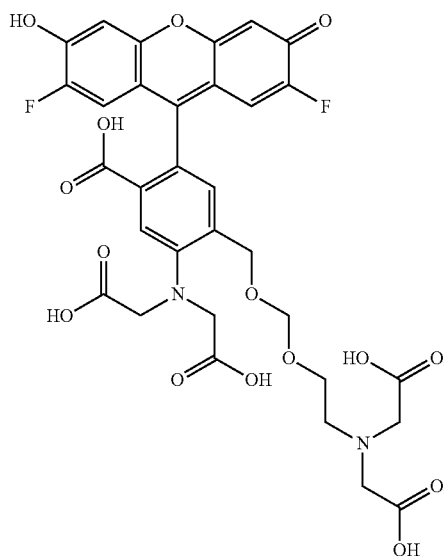 [SMILES: O=C(O)CN(CCOCOCc1cc(-c2c3cc(F)c(=O)cc-3oc3cc(O)c(F)cc23)c(C(=O)O)cc1N(CC(=O)O)CC(=O)O)CC(=O)O] |
| 21 | 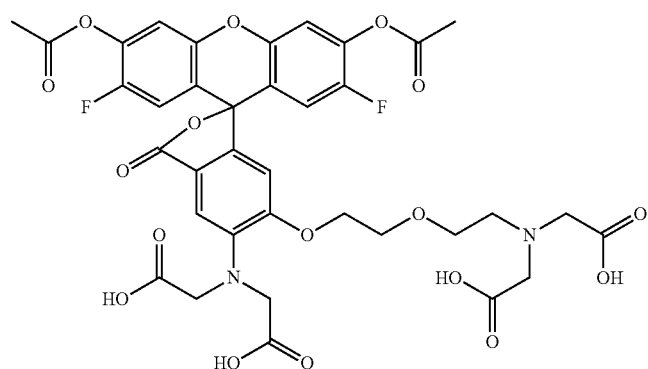 [SMILES: CC(=O)Oc1cc2c(cc1F)C1(OC(=O)c3cc(N(CC(=O)O)CC(=O)O)c(OCCOCCN(CC(=O)O)CC(=O)O)cc31)c1cc(F)c(OC(C)=O)cc1O2] |
| 22 | 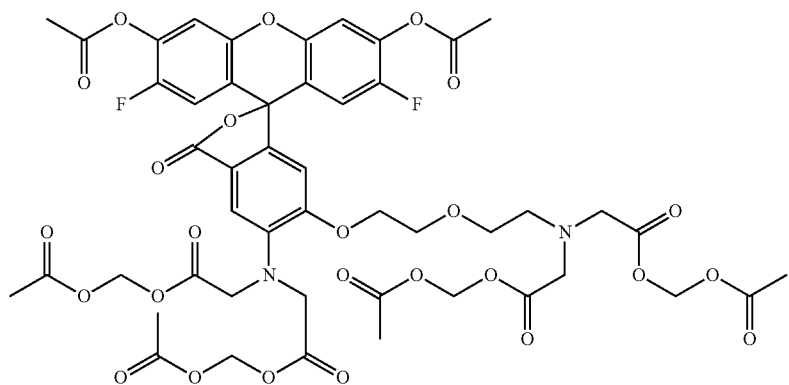 [SMILES: CC(=O)OCOC(=O)CN(CCOCCOc1cc2c(cc1N(CC(=O)OCOC(C)=O)CC(=O)OCOC(C)=O)C(=O)OC21c2cc(F)c(OC(C)=O)cc2Oc2cc(OC(C)=O)c(F)cc21)CC(=O)OCOC(C)=O] |

TABLE 2-continued
Exemplary compounds of the present disclosure:
| Compound# | Structure |
|---|---|
| 23 | 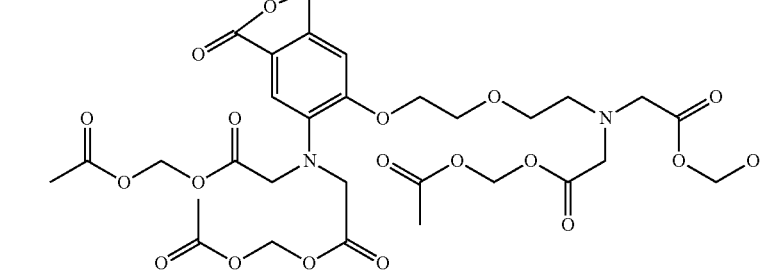 |
| 24 | 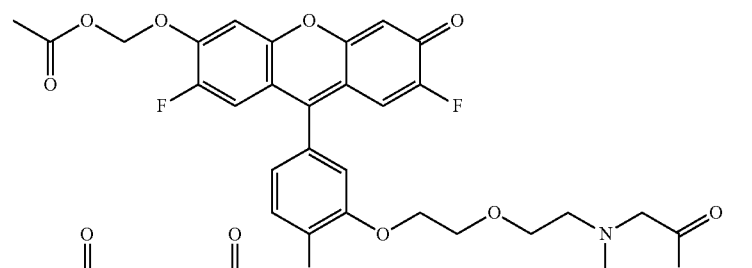 |
| 25 | 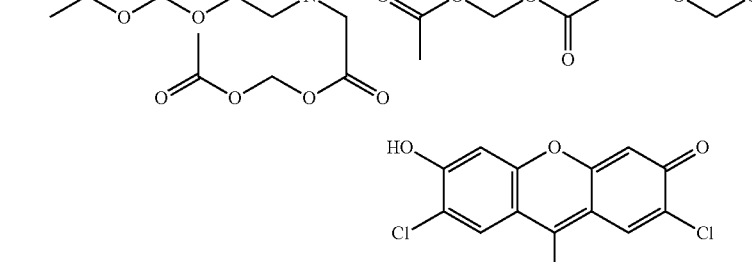 |
| 26 | 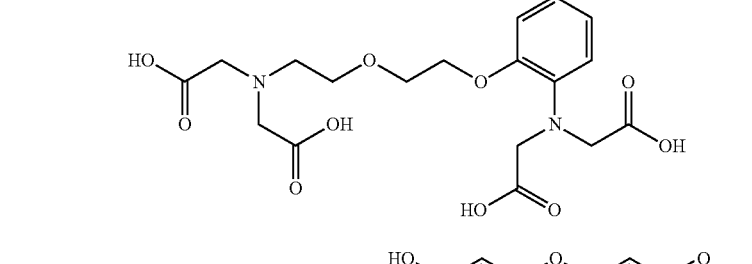 |

TABLE 2-continued
Exemplary compounds of the present disclosure:
| Compound# | Structure |
|---|---|
| 27 | 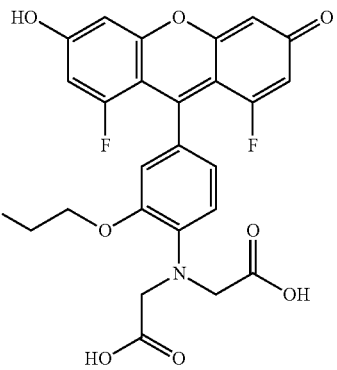 |
| 28 | 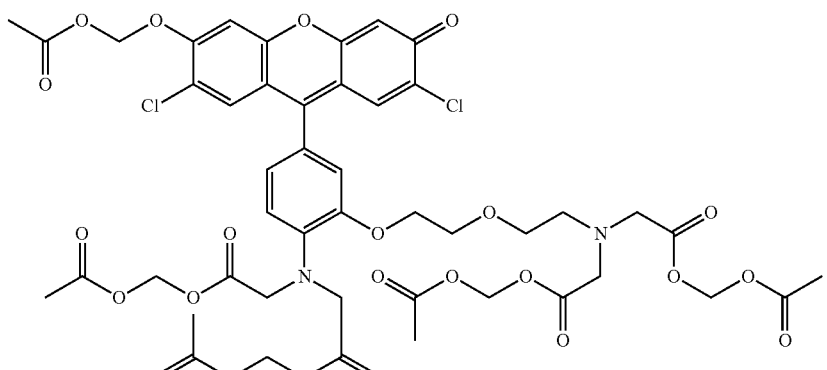 |
| 29 | 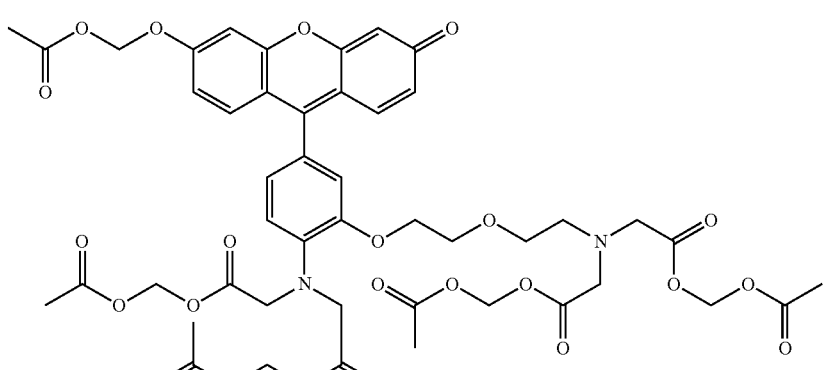 |

TABLE 2-continued
Exemplary compounds of the present disclosure:
| Compound# | Structure |
|---|---|
| 30 | 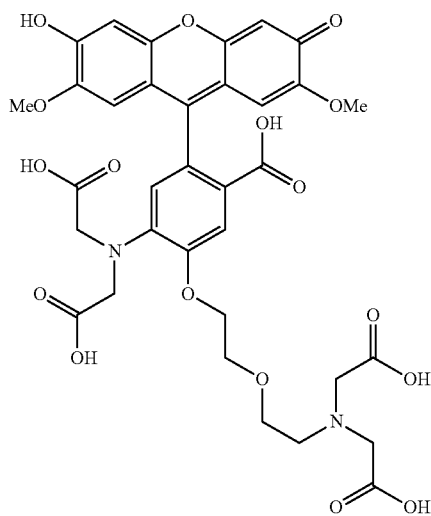 [SMILES: COc1cc2c(-c3cc(N(CC(=O)O)CC(=O)O)c(OCCOCCN(CC(=O)O)CC(=O)O)cc3C(=O)O)c3cc(OC)c(=O)cc-3oc2cc1O] |
| 31 | 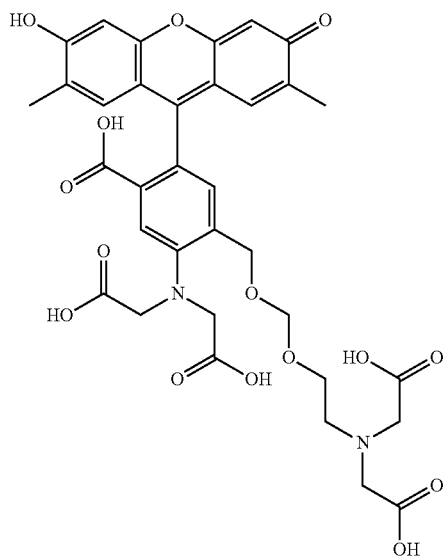 [SMILES: Cc1cc2c(-c3cc(COCOCCN(CC(=O)O)CC(=O)O)c(N(CC(=O)O)CC(=O)O)cc3C(=O)O)c3cc(C)c(=O)cc-3oc2cc1O] |
| 32 | 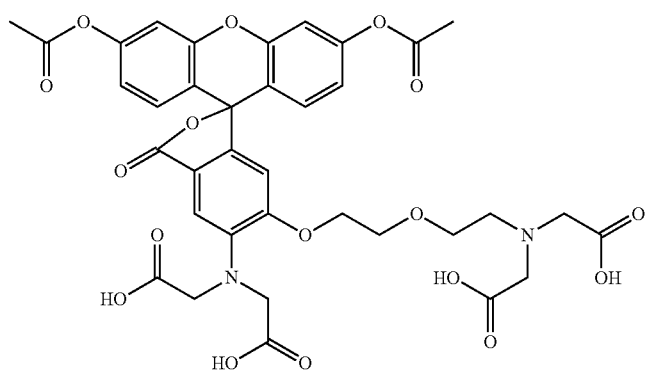 [SMILES: CC(=O)Oc1ccc2c(c1)Oc1cc(OC(C)=O)ccc1C21OC(=O)c2cc(N(CC(=O)O)CC(=O)O)c(OCCOCCN(CC(=O)O)CC(=O)O)cc21] |

TABLE 2-continued
Exemplary compounds of the present disclosure:
| Compound# | Structure |
|---|---|
| 33 | 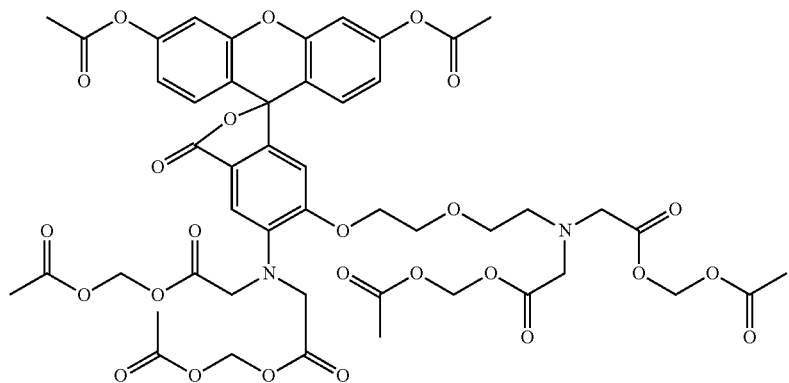 [SMILES: CC(=O)OCOC(=O)CN(CCOCCOc1cc2c(cc1N(CC(=O)OCOC(C)=O)CC(=O)OCOC(C)=O)C(=O)OC21c2ccc(OC(C)=O)cc2Oc2cc(OC(C)=O)ccc21)CC(=O)OCOC(C)=O] |
| 34 | 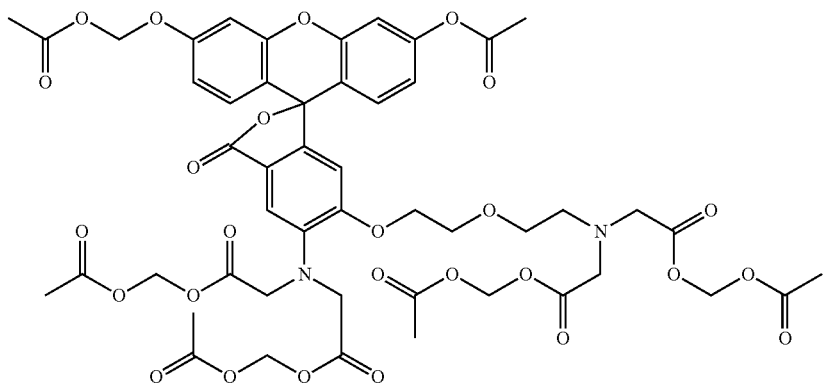 [SMILES: CC(=O)OCOC(=O)CN(CCOCCOc1cc2c(cc1N(CC(=O)OCOC(C)=O)CC(=O)OCOC(C)=O)C(=O)OC21c2ccc(OCOC(C)=O)cc2Oc2cc(OC(C)=O)ccc21)CC(=O)OCOC(C)=O] |
| 38 | 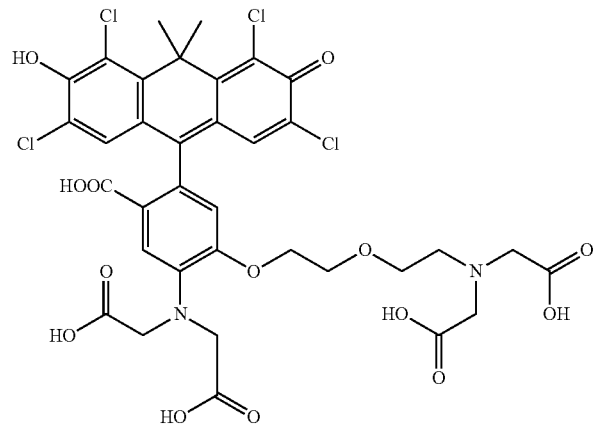 [SMILES: CC1(C)C2=C(Cl)C(=O)C(Cl)=CC2=C(c2cc(OCCOCCN(CC(=O)O)CC(=O)O)c(N(CC(=O)O)CC(=O)O)cc2C(=O)O)c2cc(Cl)c(O)c(Cl)c21] |

TABLE 2-continued
Exemplary compounds of the present disclosure:
| Compound# | Structure |
|---|---|
| 39 | 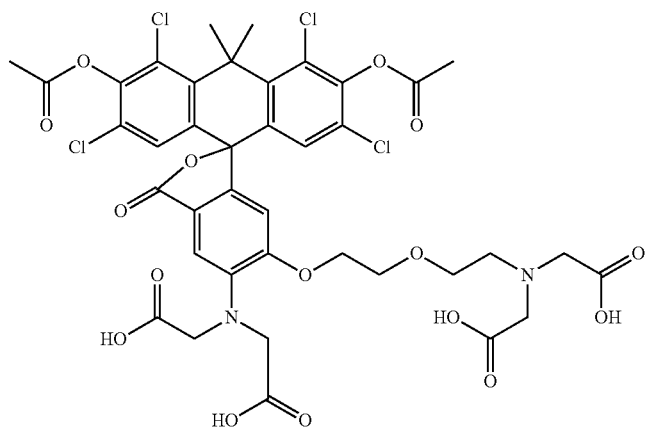 [SMILES: CC(=O)Oc1c(Cl)cc2c(c1Cl)C(C)(C)c1c(cc(Cl)c(OC(C)=O)c1Cl)C21OC(=O)c2cc(N(CC(=O)O)CC(=O)O)c(OCCOCCN(CC(=O)O)CC(=O)O)cc21] |
| 40 | 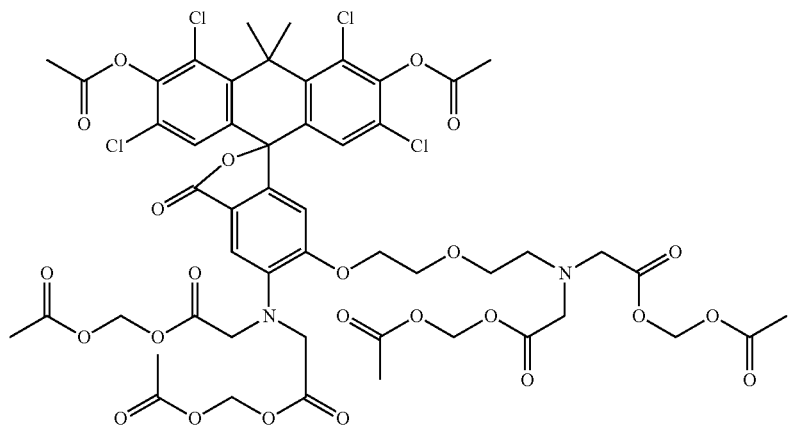 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OC(C)=O)c(Cl)c2C(C)(C)c2c1cc(Cl)c(OC(C)=O)c2Cl)CC(=O)OCOC(C)=O] |
| 41 | 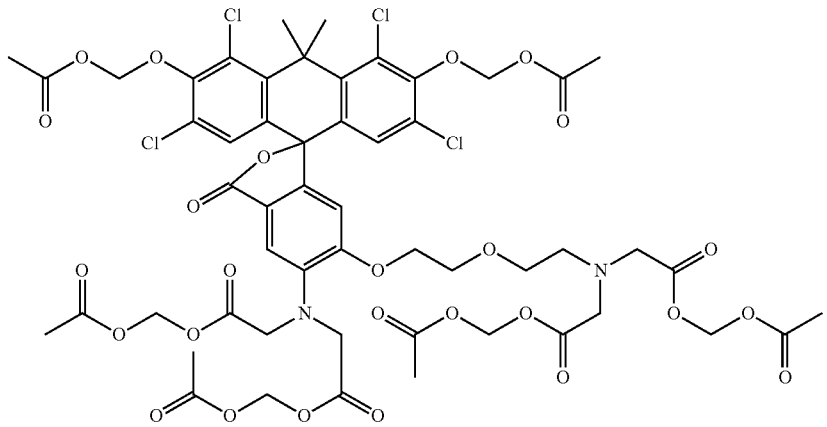 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OCOC(C)=O)c(Cl)c2C(C)(C)c2c1cc(Cl)c(OCOC(C)=O)c2Cl)CC(=O)OCOC(C)=O] |

TABLE 2-continued
Exemplary compounds of the present disclosure:
| Compound# | Structure |
|---|---|
| 68 | 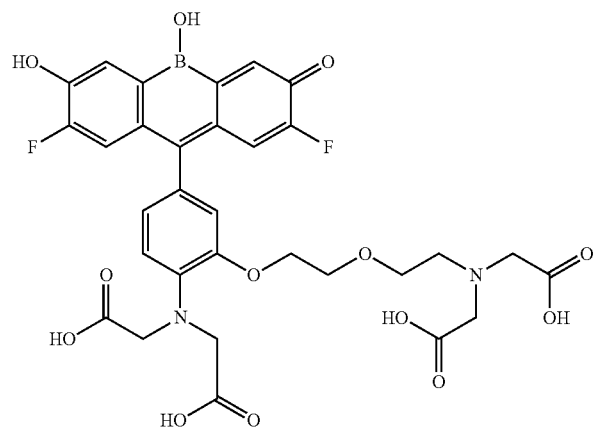 [SMILES: O=C(O)CN(CCOCCOc1cc(C2=C3C=C(F)C(=O)C=C3B(O)c3cc(O)c(F)cc32)ccc1N(CC(=O)O)CC(=O)O)CC(=O)O] |
| 69 | 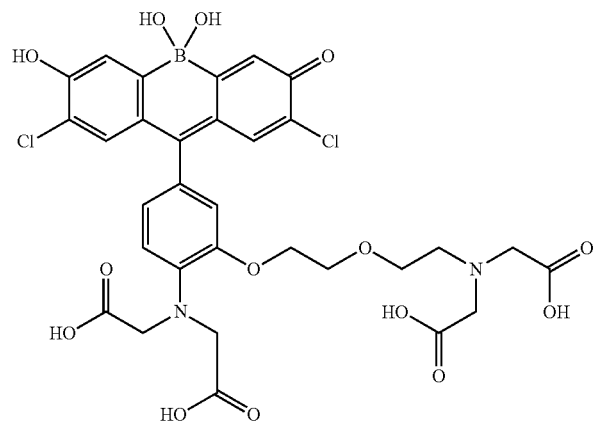 |
| 70 | 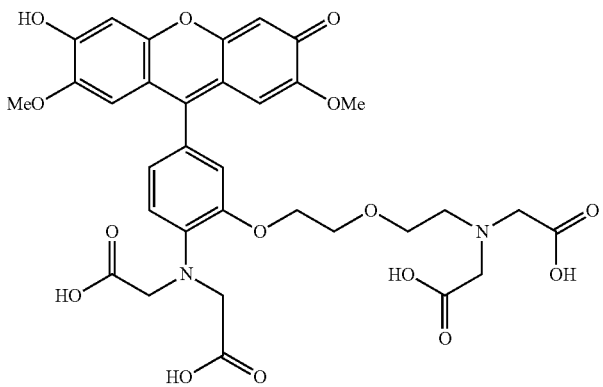 [SMILES: COc1cc2c(-c3ccc(N(CC(=O)O)CC(=O)O)c(OCCOCCN(CC(=O)O)CC(=O)O)c3)c3cc(OC)c(=O)cc-3oc2cc1O] |

TABLE 2-continued
Exemplary compounds of the present disclosure:
| Compound# | Structure |
|---|---|
| 71 | 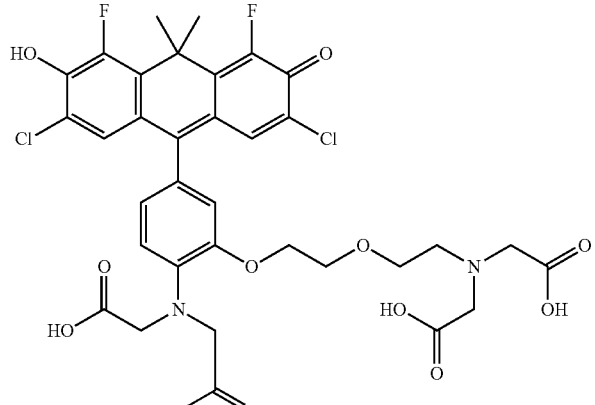 |
| 72 | 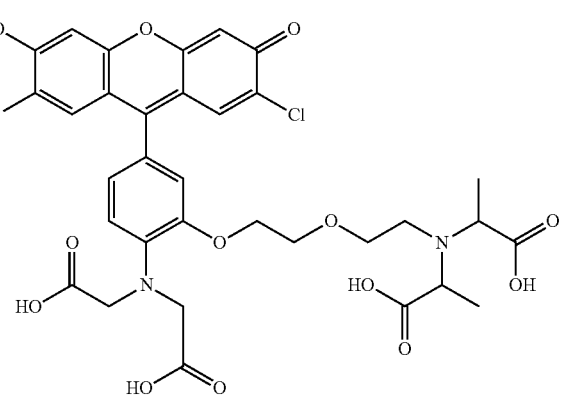 |
| 73 | 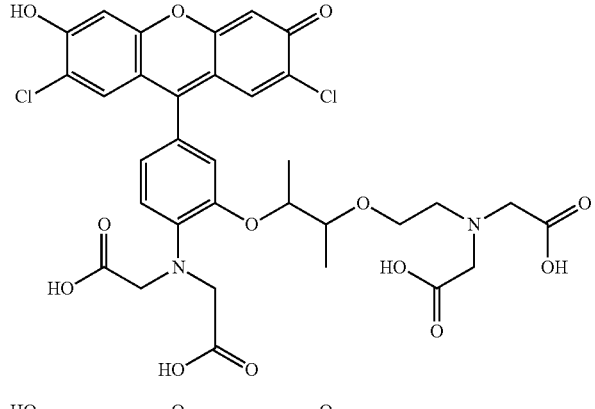 |
| 74 | 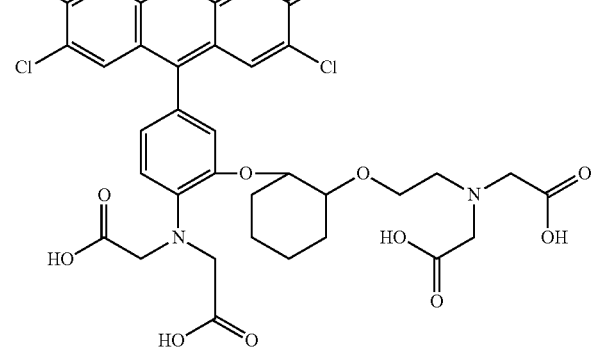 |

TABLE 2-continued
Exemplary compounds of the present disclosure:
| Compound# | Structure |
|---|---|
| 75 | 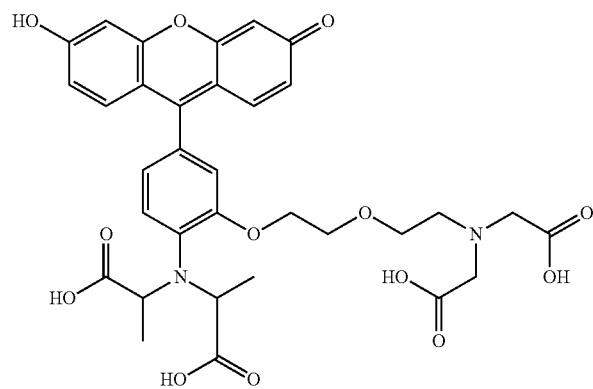 [SMILES: CC(C(=O)O)N(c1ccc(-c2c3ccc(=O)cc-3oc3cc(O)ccc23)cc1OCCOCCN(CC(=O)O)CC(=O)O)C(C)C(=O)O] |
| 76 | 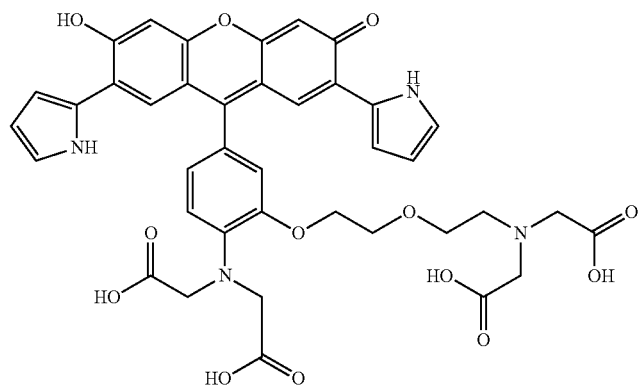 [SMILES: O=C(O)CN(CCOCCOc1cc(-c2c3cc(-c4ccc[nH]4)c(=O)cc-3oc3cc(O)c(-c4ccc[nH]4)cc23)ccc1N(CC(=O)O)CC(=O)O)CC(=O)O] |
| 77 | 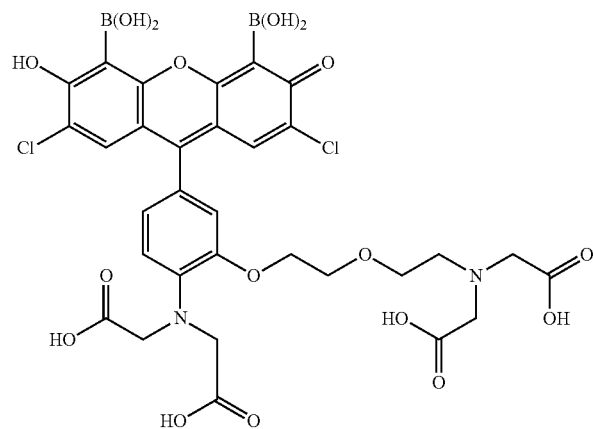 [SMILES: O=C(O)CN(CCOCCOc1cc(-c2c3cc(Cl)c(=O)c(B(O)O)c-3oc3c(B(O)O)c(O)c(Cl)cc23)ccc1N(CC(=O)O)CC(=O)O)CC(=O)O] |

TABLE 2-continued
Exemplary compounds of the present disclosure:
| Compound# | Structure |
|---|---|
| 78 | 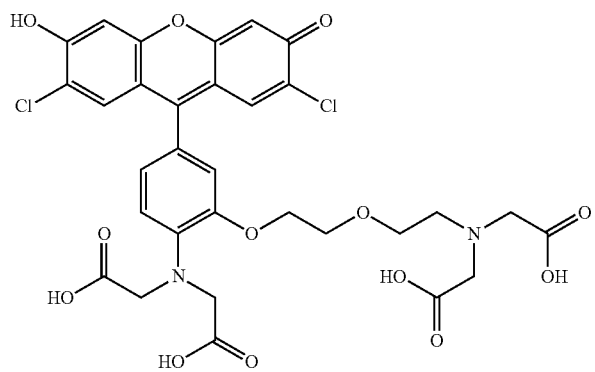 [SMILES: O=C(O)CN(CCOCCOc1cc(-c2c3cc(Cl)c(=O)cc-3oc3cc(O)c(Cl)cc23)ccc1N(CC(=O)O)CC(=O)O)CC(=O)O] |
| 79 | 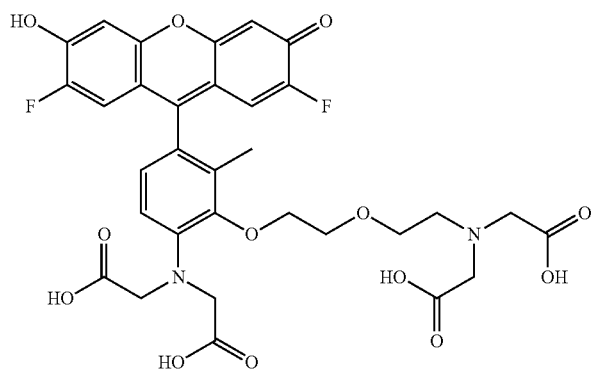 [SMILES: Cc1c(-c2c3cc(F)c(=O)cc-3oc3cc(O)c(F)cc23)ccc(N(CC(=O)O)CC(=O)O)c1OCCOCCN(CC(=O)O)CC(=O)O] |
| 80 | 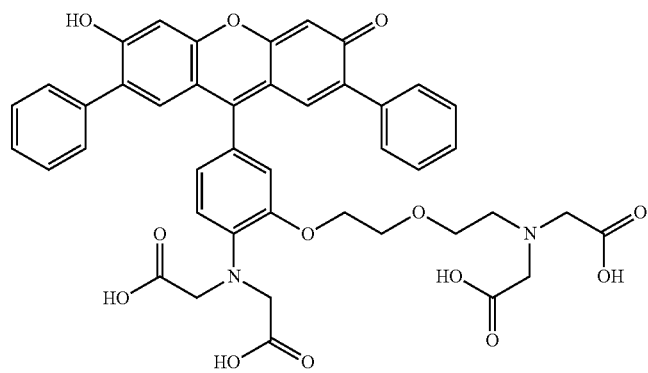 [SMILES: O=C(O)CN(CCOCCOc1cc(-c2c3cc(-c4ccccc4)c(=O)cc-3oc3cc(O)c(-c4ccccc4)cc23)ccc1N(CC(=O)O)CC(=O)O)CC(=O)O] |
| 81 | 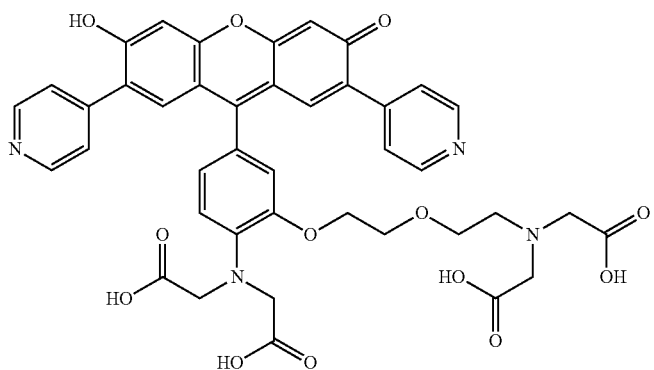 [SMILES: O=C(O)CN(CCOCCOc1cc(-c2c3cc(-c4ccncc4)c(=O)cc-3oc3cc(O)c(-c4ccncc4)cc23)ccc1N(CC(=O)O)CC(=O)O)CC(=O)O] |

TABLE 2-continued
Exemplary compounds of the present disclosure:
| Compound# | Structure |
|---|---|
| 82 | 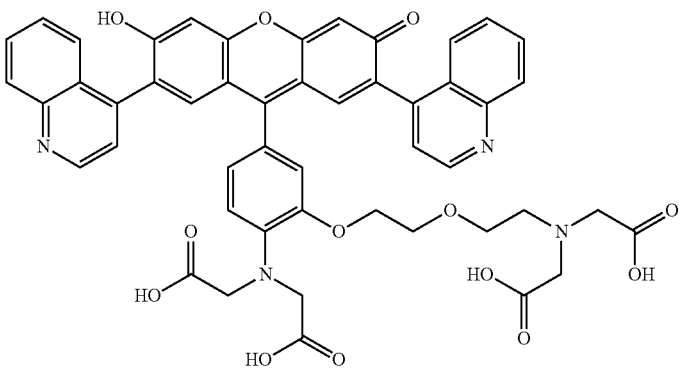 [SMILES: O=C(O)CN(CCOCCOc1cc(-c2c3cc(-c4ccnc5ccccc45)c(=O)cc-3oc3cc(O)c(-c4ccnc5ccccc45)cc23)ccc1N(CC(=O)O)CC(=O)O)CC(=O)O] |
| 83 | 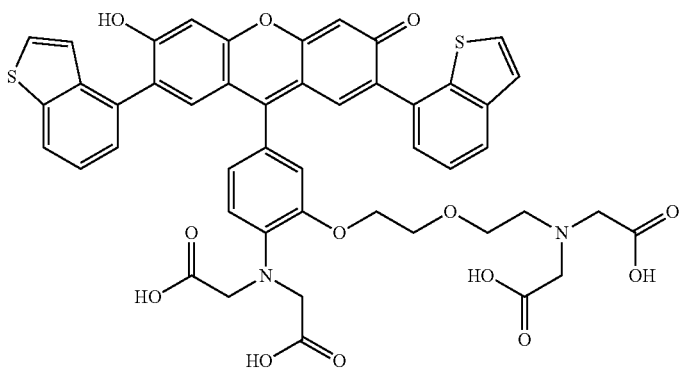 [SMILES: O=C(O)CN(CCOCCOc1cc(-c2c3cc(-c4cccc5ccsc45)c(=O)cc-3oc3cc(O)c(-c4cccc5sccc45)cc23)ccc1N(CC(=O)O)CC(=O)O)CC(=O)O] |
| 84 | 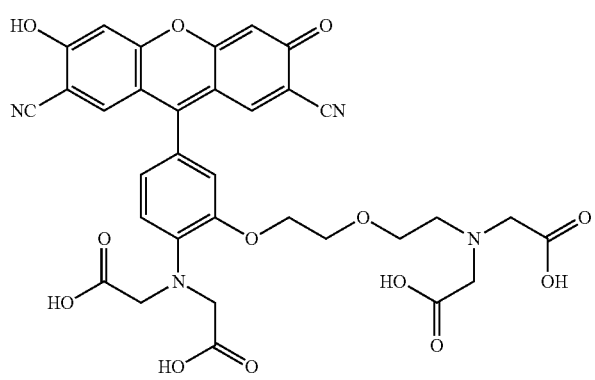 [SMILES: N#Cc1cc2c(-c3ccc(N(CC(=O)O)CC(=O)O)c(OCCOCCN(CC(=O)O)CC(=O)O)c3)c3cc(C#N)c(=O)cc-3oc2cc1O] |
| 85 | 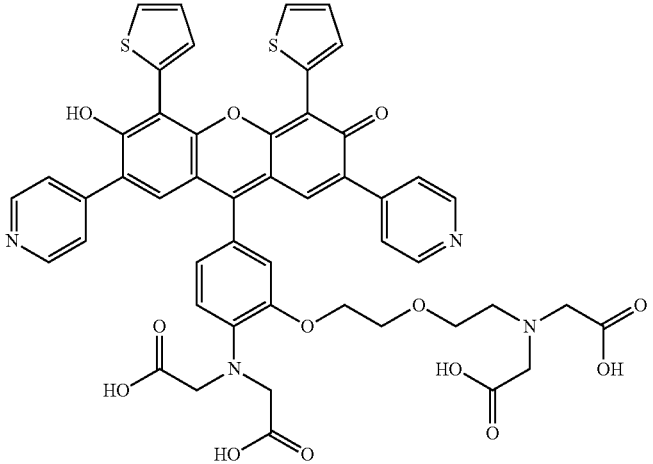 [SMILES: O=C(O)CN(CCOCCOc1cc(-c2c3cc(-c4ccncc4)c(=O)c(-c4cccs4)c-3oc3c(-c4cccs4)c(O)c(-c4ccncc4)cc23)ccc1N(CC(=O)O)CC(=O)O)CC(=O)O] |

TABLE 2-continued
Exemplary compounds of the present disclosure:
| Compound# | Structure |
|---|---|
| 86 | 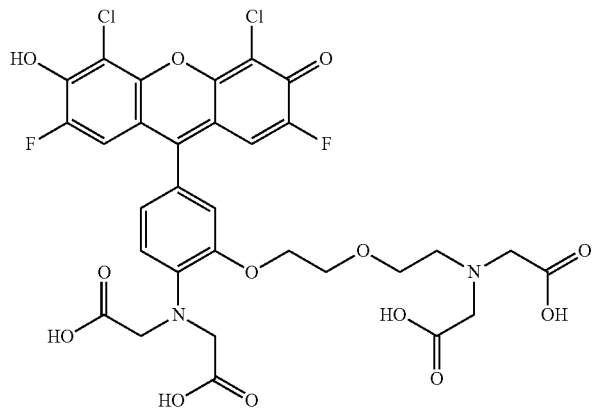 [SMILES: O=C(O)CN(CCOCCOc1cc(-c2c3cc(F)c(=O)c(Cl)c-3oc3c(Cl)c(O)c(F)cc23)ccc1N(CC(=O)O)CC(=O)O)CC(=O)O] |
| 87 | 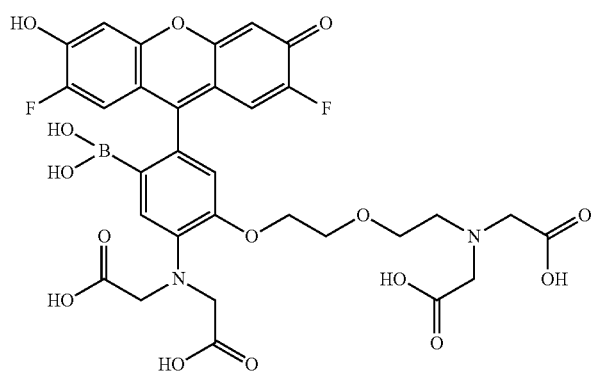 [SMILES: O=C(O)CN(CCOCCOc1cc(-c2c3cc(F)c(=O)cc-3oc3cc(O)c(F)cc23)c(B(O)O)cc1N(CC(=O)O)CC(=O)O)CC(=O)O] |
| 88 | 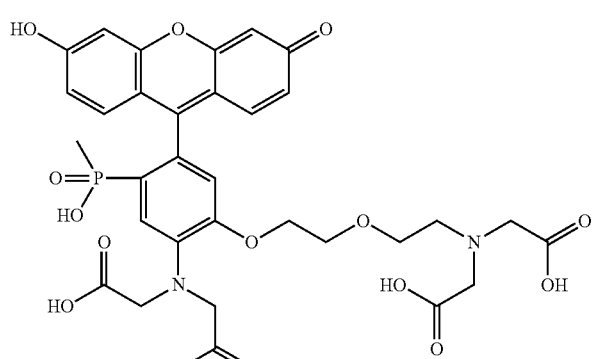 |
| 89 | 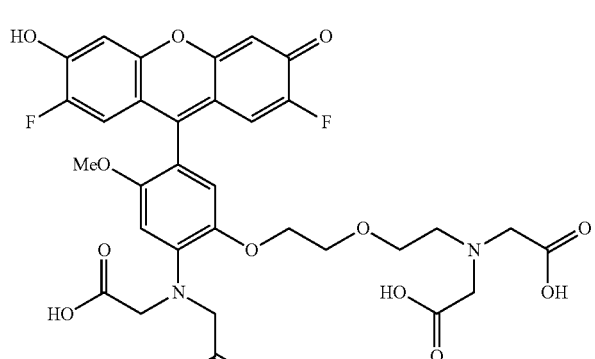 |

TABLE 2-continued
Exemplary compounds of the present disclosure:
| Compound# | Structure |
|---|---|
| 90 | 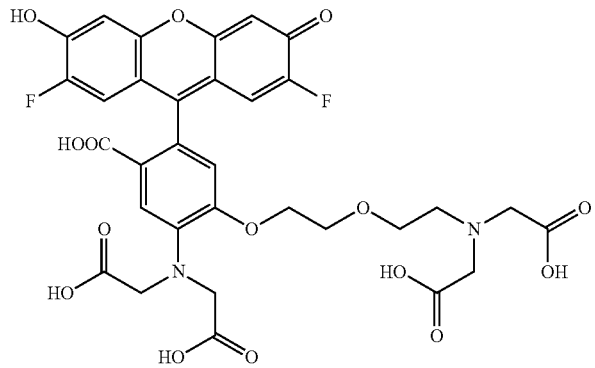 [SMILES: O=C(O)CN(CCOCCOc1cc(-c2c3cc(F)c(=O)cc-3oc3cc(O)c(F)cc23)c(C(=O)O)cc1N(CC(=O)O)CC(=O)O)CC(=O)O] |
| 91 | 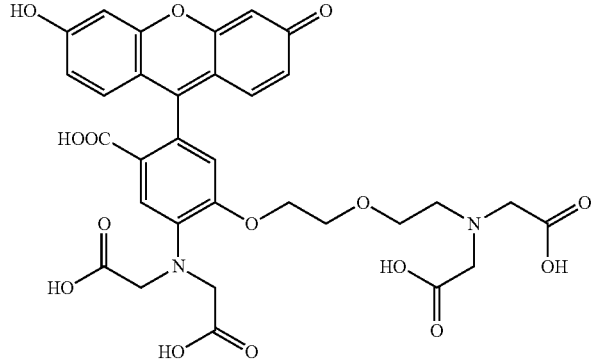 [SMILES: O=C(O)CN(CCOCCOc1cc(-c2c3ccc(=O)cc-3oc3cc(O)ccc23)c(C(=O)O)cc1N(CC(=O)O)CC(=O)O)CC(=O)O] |
| 92 | 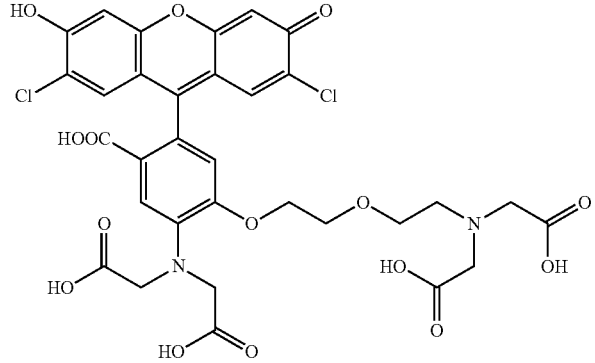 [SMILES: O=C(O)CN(CCOCCOc1cc(-c2c3cc(Cl)c(=O)cc-3oc3cc(O)c(Cl)cc23)c(C(=O)O)cc1N(CC(=O)O)CC(=O)O)CC(=O)O] |
| 93 | 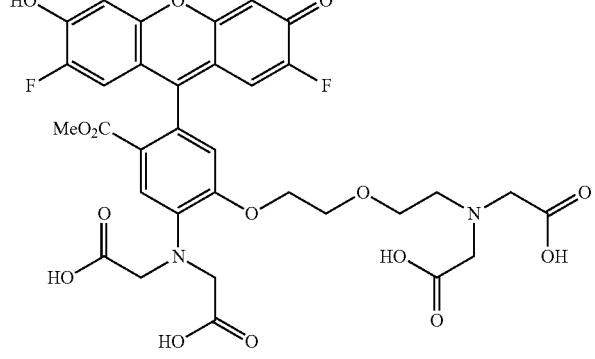 |

TABLE 2-continued
Exemplary compounds of the present disclosure:
| Compound# | Structure |
|---|---|
| 94 | 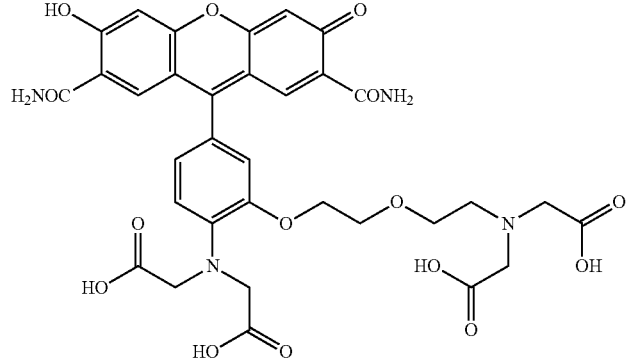 [SMILES: NC(=O)c1cc2c(-c3ccc(N(CC(=O)O)CC(=O)O)c(OCCOCCN(CC(=O)O)CC(=O)O)c3)c3cc(C(N)=O)c(=O)cc-3oc2cc1O] |
| 95 | 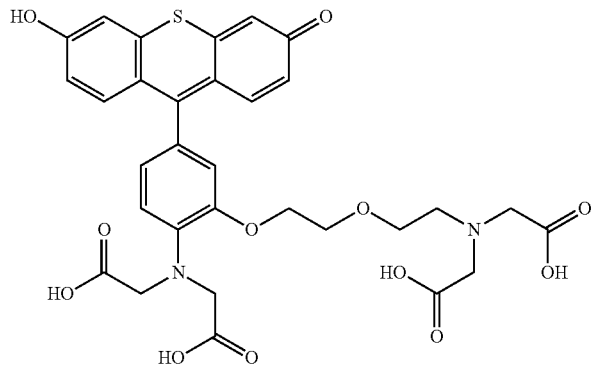 [SMILES: O=C(O)CN(CCOCCOc1cc(-c2c3ccc(=O)cc-3sc3cc(O)ccc23)ccc1N(CC(=O)O)CC(=O)O)CC(=O)O] |
| 96 | 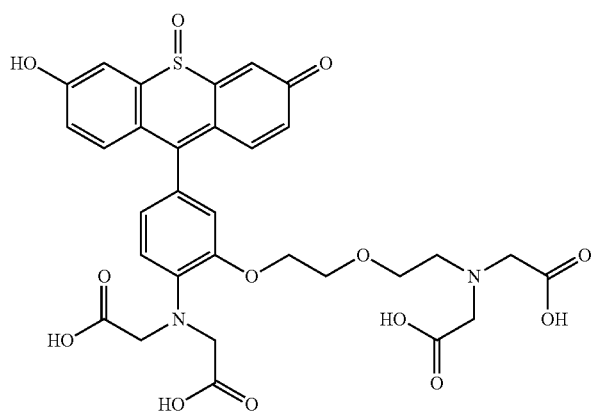 [SMILES: O=C1C=CC2=C(c3ccc(N(CC(=O)O)CC(=O)O)c(OCCOCCN(CC(=O)O)CC(=O)O)c3)c3ccc(O)cc3S(=O)C2=C1] |
| 97 | 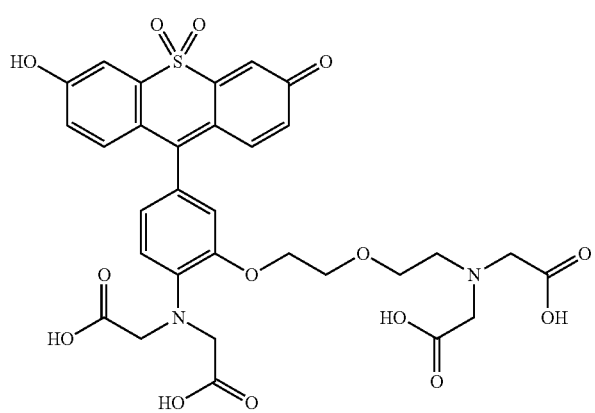 [SMILES: O=C1C=CC2=C(c3ccc(N(CC(=O)O)CC(=O)O)c(OCCOCCN(CC(=O)O)CC(=O)O)c3)c3ccc(O)cc3S(=O)(=O)C2=C1] |

TABLE 2-continued
Exemplary compounds of the present disclosure:
| Compound# | Structure |
|---|---|
| 98 | 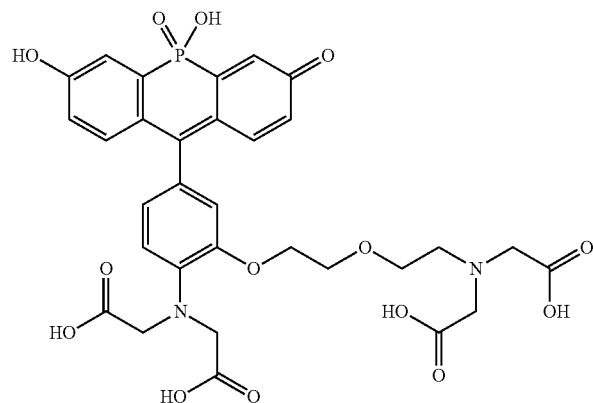 [SMILES: O=C1C=CC2=C(c3ccc(N(CC(=O)O)CC(=O)O)c(OCCOCCN(CC(=O)O)CC(=O)O)c3)c3ccc(O)cc3P(=O)(O)C2=C1] |
| 99 | 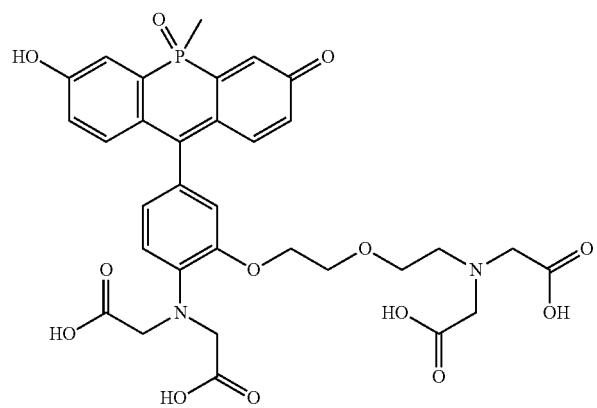 [SMILES: CP1(=O)C2=CC(=O)C=CC2=C(c2ccc(N(CC(=O)O)CC(=O)O)c(OCCOCCN(CC(=O)O)CC(=O)O)c2)c2ccc(O)cc21] |
| 100 | 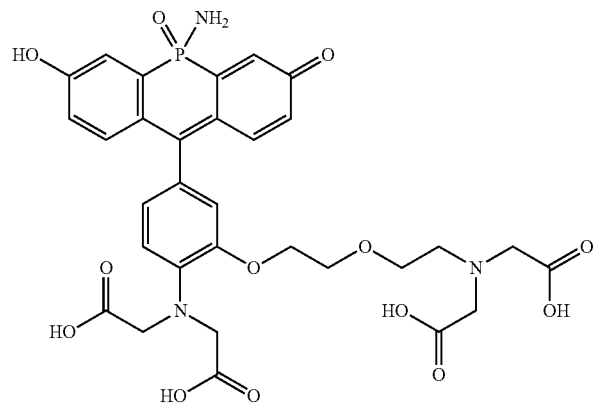 [SMILES: NP1(=O)C2=CC(=O)C=CC2=C(c2ccc(N(CC(=O)O)CC(=O)O)c(OCCOCCN(CC(=O)O)CC(=O)O)c2)c2ccc(O)cc21] |

TABLE 2-continued
Exemplary compounds of the present disclosure:
| Compound# | Structure |
|---|---|
| 101 | 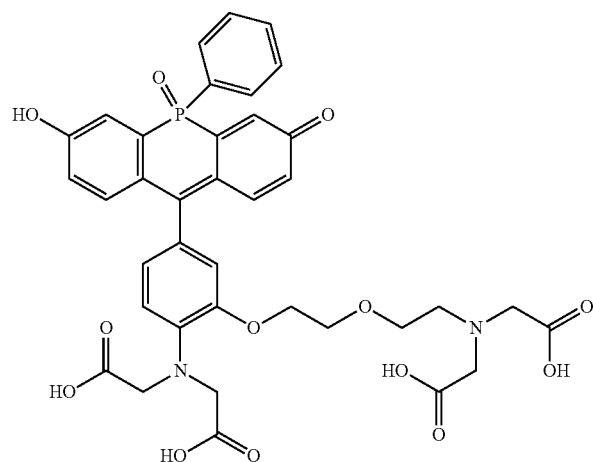 [SMILES: O=C1C=CC2=C(c3ccc(N(CC(=O)O)CC(=O)O)c(OCCOCCN(CC(=O)O)CC(=O)O)c3)c3ccc(O)cc3P(=O)(c3ccccc3)C2=C1] |
| 102 | 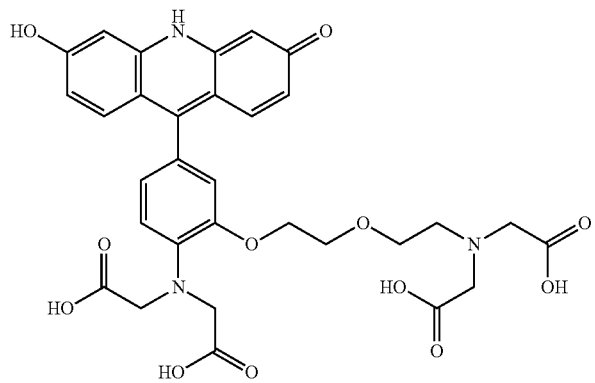 [SMILES: O=C(O)CN(CCOCCOc1cc(-c2c3ccc(=O)cc-3[nH]c3cc(O)ccc23)ccc1N(CC(=O)O)CC(=O)O)CC(=O)O] |
| 103 | 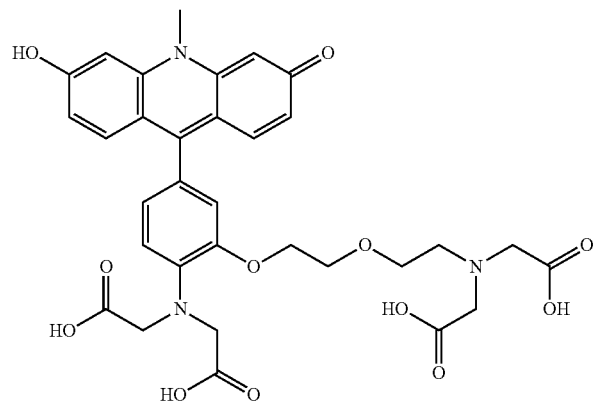 [SMILES: Cn1c2cc(=O)ccc-2c(-c2ccc(N(CC(=O)O)CC(=O)O)c(OCCOCCN(CC(=O)O)CC(=O)O)c2)c2ccc(O)cc21] |

TABLE 2-continued
Exemplary compounds of the present disclosure:
| Compound# | Structure |
|---|---|
| 104 | 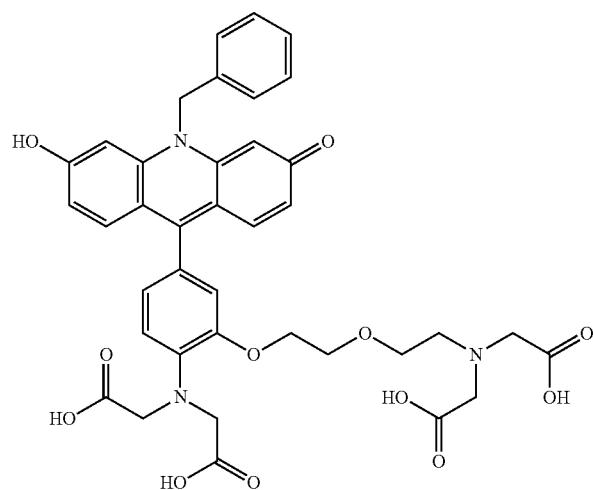 [SMILES: O=C(O)CN(CCOCCOc1cc(-c2c3ccc(=O)cc-3n(Cc3ccccc3)c3cc(O)ccc23)ccc1N(CC(=O)O)CC(=O)O)CC(=O)O] |
| 105 | 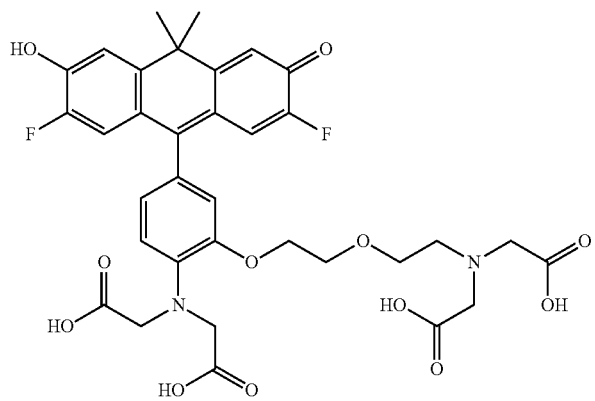 [SMILES: CC1(C)C2=CC(=O)C(F)=CC2=C(c2ccc(N(CC(=O)O)CC(=O)O)c(OCCOCCN(CC(=O)O)CC(=O)O)c2)c2cc(F)c(O)cc21] |
| 106 | 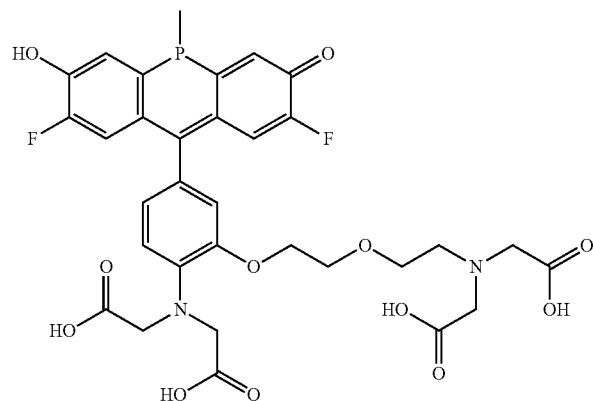 [SMILES: Cp1c2cc(=O)c(F)cc-2c(-c2ccc(N(CC(=O)O)CC(=O)O)c(OCCOCCN(CC(=O)O)CC(=O)O)c2)c2cc(F)c(O)cc21] |

TABLE 2-continued
Exemplary compounds of the present disclosure:
| Compound# | Structure |
|---|---|
| 107 | 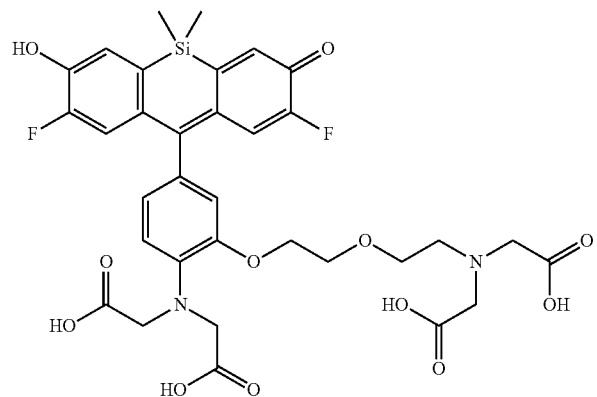 [SMILES: C[Si]1(C)C2=CC(=O)C(F)=CC2=C(c2ccc(N(CC(=O)O)CC(=O)O)c(OCCOCCN(CC(=O)O)CC(=O)O)c2)c2cc(F)c(O)cc21] |
| 108 | 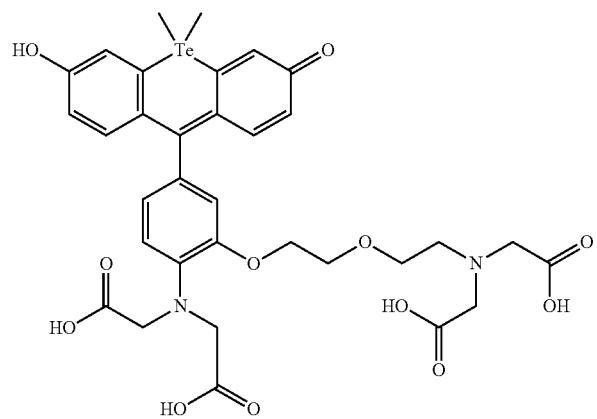 |
| 109 | 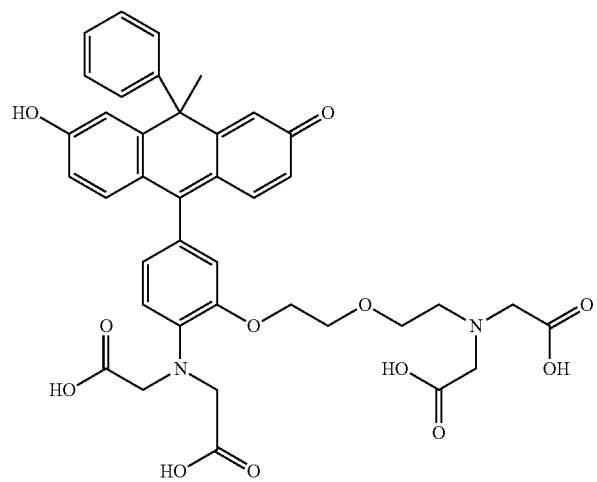 [SMILES: CC1(c2ccccc2)C2=CC(=O)C=CC2=C(c2ccc(N(CC(=O)O)CC(=O)O)c(OCCOCCN(CC(=O)O)CC(=O)O)c2)c2ccc(O)cc21] |

TABLE 2-continued
Exemplary compounds of the present disclosure:
| Compound# | Structure |
|---|---|
| 110 | 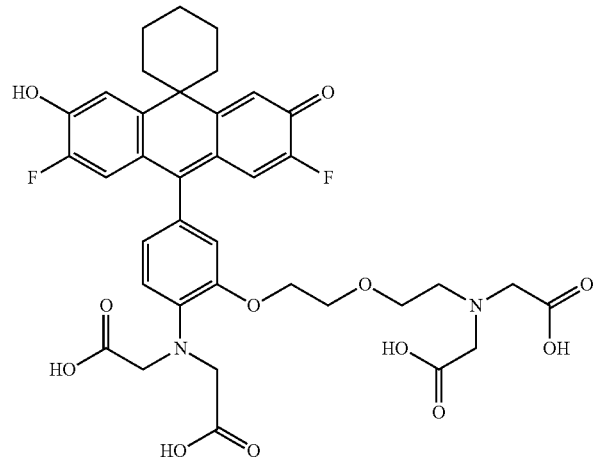 [SMILES: O=C(O)CN(CCOCCOc1cc(C2=C3C=C(F)C(=O)C=C3C3(CCCCC3)c3cc(O)c(F)cc32)ccc1N(CC(=O)O)CC(=O)O)CC(=O)O] |
| 111 | 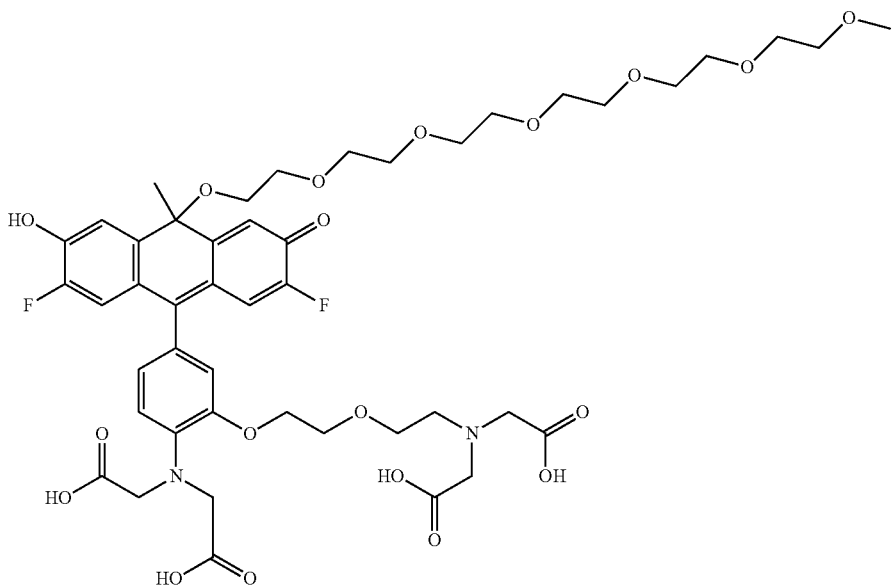 [SMILES: COCCOCCOCCOCCOCCOCCOC1(C)C2=CC(=O)C(F)=CC2=C(c2ccc(N(CC(=O)O)CC(=O)O)c(OCCOCCN(CC(=O)O)CC(=O)O)c2)c2cc(F)c(O)cc21] |

TABLE 2-continued

Exemplary compounds of the present disclosure:

| Compound# | Structure |
|---|---|
| 112 | 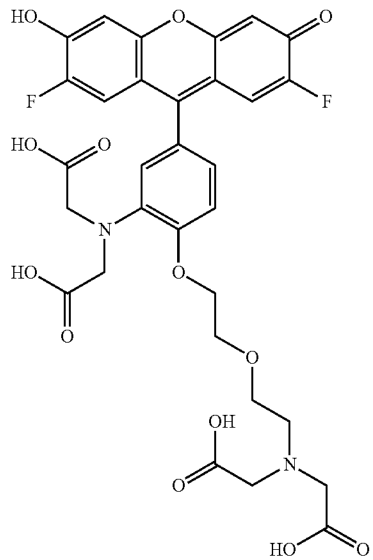 [SMILES: O=C(O)CN(CCOCCOc1ccc(-c2c3cc(F)c(=O)cc-3oc3cc(O)c(F)cc23)cc1N(CC(=O)O)CC(=O)O)CC(=O)O] |
| 113 | 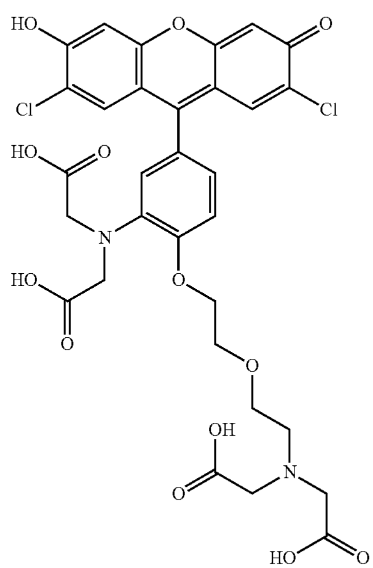 [SMILES: O=C(O)CN(CCOCCOc1ccc(-c2c3cc(Cl)c(=O)cc-3oc3cc(O)c(Cl)cc23)cc1N(CC(=O)O)CC(=O)O)CC(=O)O] |

TABLE 2-continued
Exemplary compounds of the present disclosure:
| Compound# | Structure |
|---|---|
| 114 | 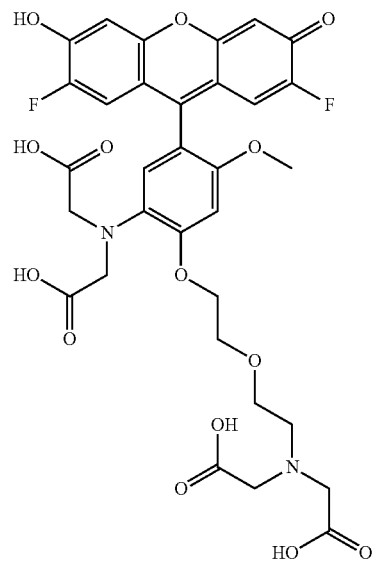 [SMILES: COc1cc(OCCOCCN(CC(=O)O)CC(=O)O)c(N(CC(=O)O)CC(=O)O)cc1-c1c2cc(F)c(=O)cc-2oc2cc(O)c(F)cc12] |
| 115 | 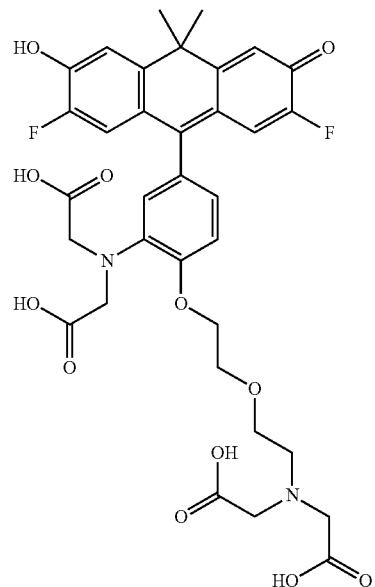 [SMILES: CC1(C)C2=CC(=O)C(F)=CC2=C(c2ccc(OCCOCCN(CC(=O)O)CC(=O)O)c(N(CC(=O)O)CC(=O)O)c2)c2cc(F)c(O)cc21] |

TABLE 2-continued
Exemplary compounds of the present disclosure:
| Compound# | Structure |
|---|---|
| 116 | 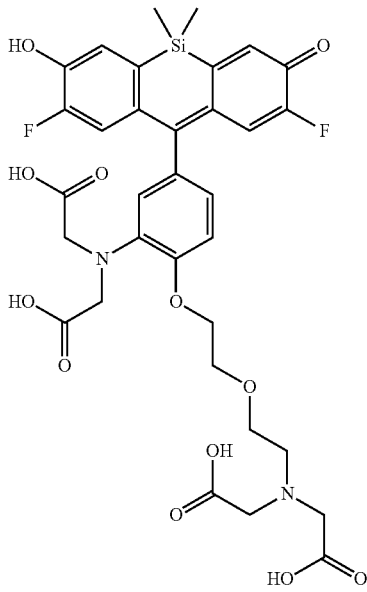 [SMILES: C[Si]1(C)C2=CC(=O)C(F)=CC2=C(c2ccc(OCCOCCN(CC(=O)O)CC(=O)O)c(N(CC(=O)O)CC(=O)O)c2)c2cc(F)c(O)cc21] |
| 117 | 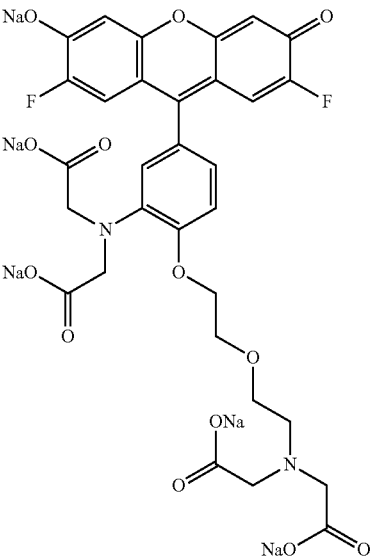 |

TABLE 2-continued

Exemplary compounds of the present disclosure:

| Compound# | Structure |
|---|---|
| 118 | (structure) |
| 119 | (structure) |

TABLE 2-continued
Exemplary compounds of the present disclosure:
| Compound# | Structure |
|---|---|
| 120 | 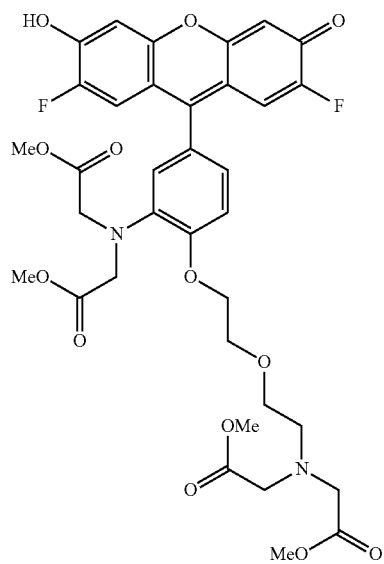 |
| 121 | 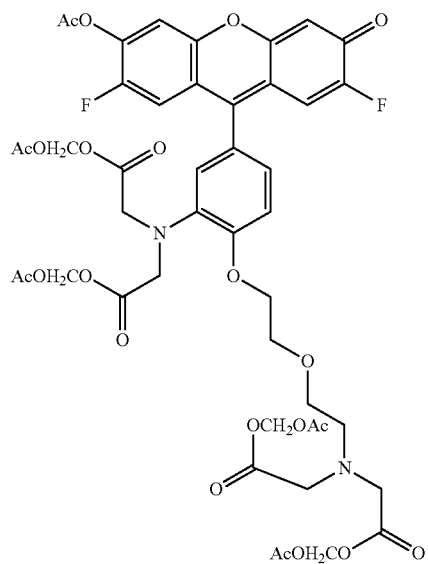 |

TABLE 2-continued
Exemplary compounds of the present disclosure:
| Compound# | Structure |
|---|---|
| 123 | 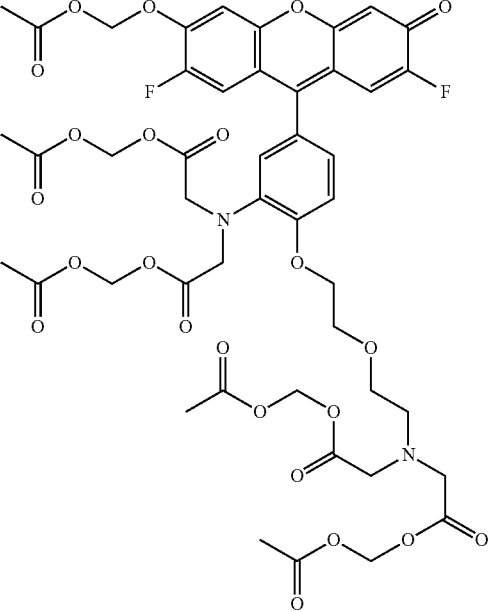 [SMILES: CC(=O)OCOC(=O)CN(CCOCCOc1ccc(-c2c3cc(F)c(=O)cc-3oc3cc(OCOC(C)=O)c(F)cc23)cc1N(CC(=O)OCOC(C)=O)CC(=O)OCOC(C)=O)CC(=O)OCOC(C)=O] |
| 124 | 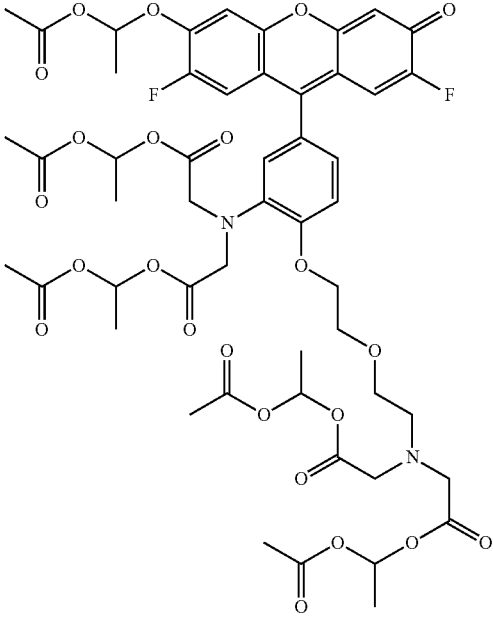 [SMILES: CC(=O)OC(C)OC(=O)CN(CCOCCOc1ccc(-c2c3cc(F)c(=O)cc-3oc3cc(OC(C)OC(C)=O)c(F)cc23)cc1N(CC(=O)OC(C)OC(C)=O)CC(=O)OC(C)OC(C)=O)CC(=O)OC(C)OC(C)=O] |

TABLE 2-continued
Exemplary compounds of the present disclosure:
| Compound# | Structure |
|---|---|
| 125 | 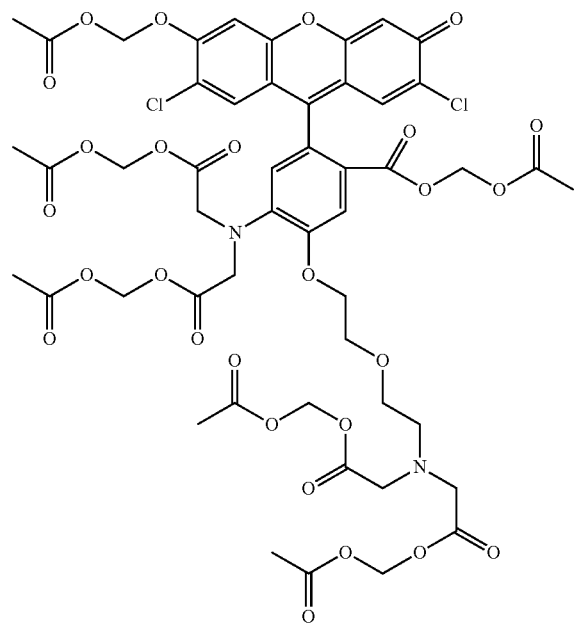 [SMILES: CC(=O)OCOC(=O)CN(CCOCCOc1cc(C(=O)OCOC(C)=O)c(-c2c3cc(Cl)c(=O)cc-3oc3cc(OCOC(C)=O)c(Cl)cc23)cc1N(CC(=O)OCOC(C)=O)CC(=O)OCOC(C)=O)CC(=O)OCOC(C)=O] |
| 126 | 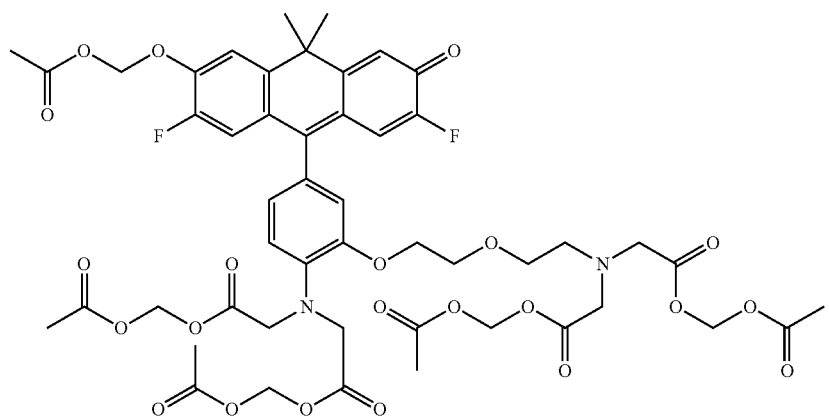 [SMILES: CC(=O)OCOC(=O)CN(CCOCCOc1cc(C2=C3C=C(F)C(=O)C=C3C(C)(C)c3cc(OCOC(C)=O)c(F)cc32)ccc1N(CC(=O)OCOC(C)=O)CC(=O)OCOC(C)=O)CC(=O)OCOC(C)=O] |
| 127 | 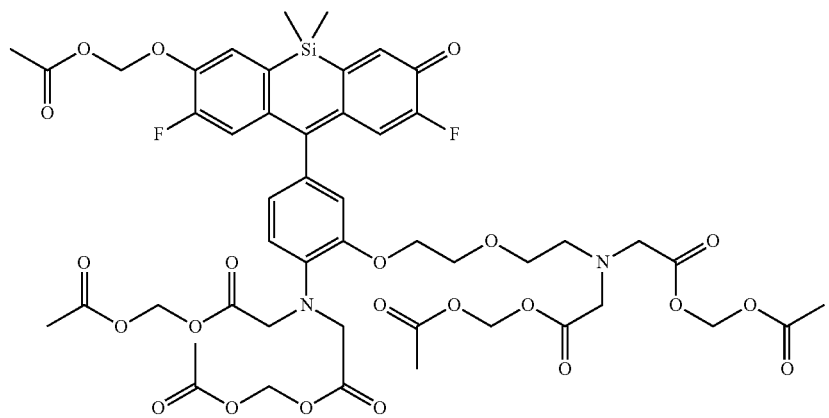 [SMILES: CC(=O)OCOC(=O)CN(CCOCCOc1cc(C2=C3C=C(F)C(=O)C=C3[Si](C)(C)c3cc(OCOC(C)=O)c(F)cc32)ccc1N(CC(=O)OCOC(C)=O)CC(=O)OCOC(C)=O)CC(=O)OCOC(C)=O] |

TABLE 2-continued

Exemplary compounds of the present disclosure:

| Compound# | Structure |
|---|---|
| 128 | 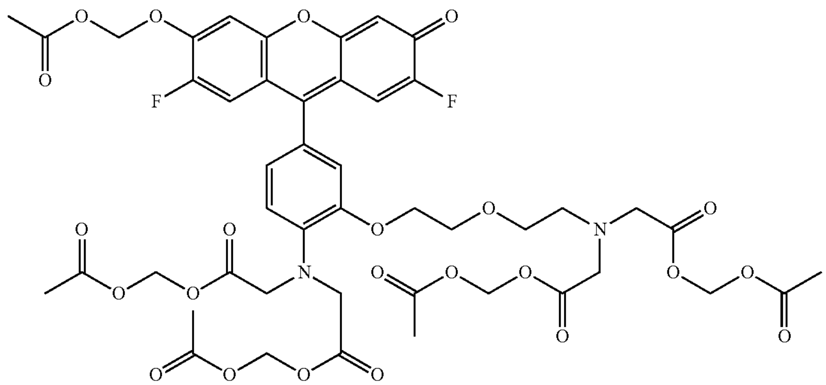 |
| 129 | 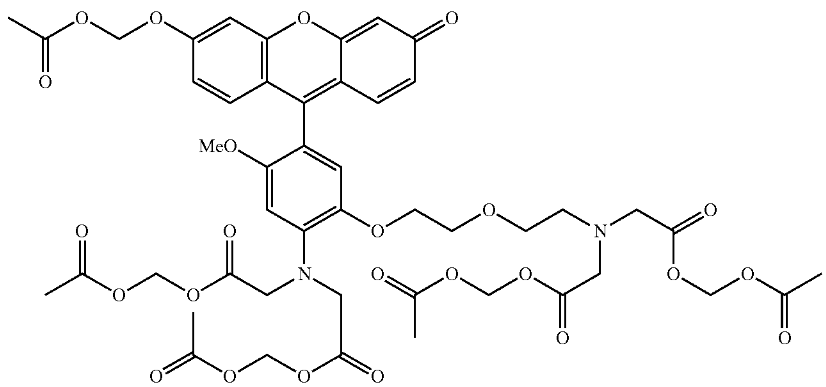 [SMILES: COc1cc(N(CC(=O)OCOC(C)=O)CC(=O)OCOC(C)=O)c(OCCOCCN(CC(=O)OCOC(C)=O)CC(=O)OCOC(C)=O)cc1-c1c2ccc(=O)cc-2oc2cc(OCOC(C)=O)ccc12] |
| 130 | 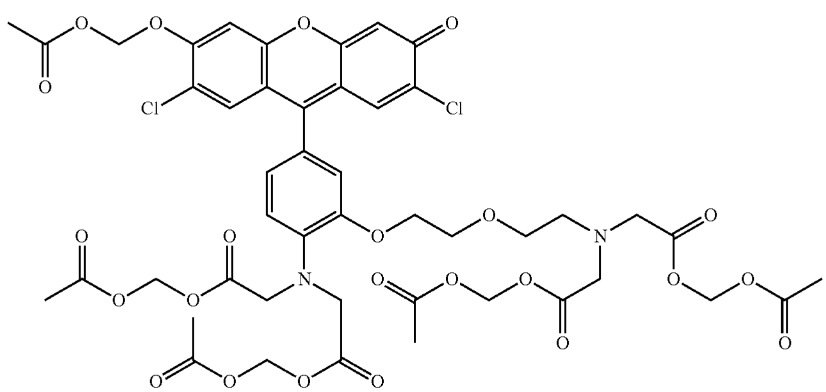 [SMILES: CC(=O)OCOC(=O)CN(CCOCCOc1cc(-c2c3cc(Cl)c(=O)cc-3oc3cc(OCOC(C)=O)c(Cl)cc23)ccc1N(CC(=O)OCOC(C)=O)CC(=O)OCOC(C)=O)CC(=O)OCOC(C)=O] |
| 131 | 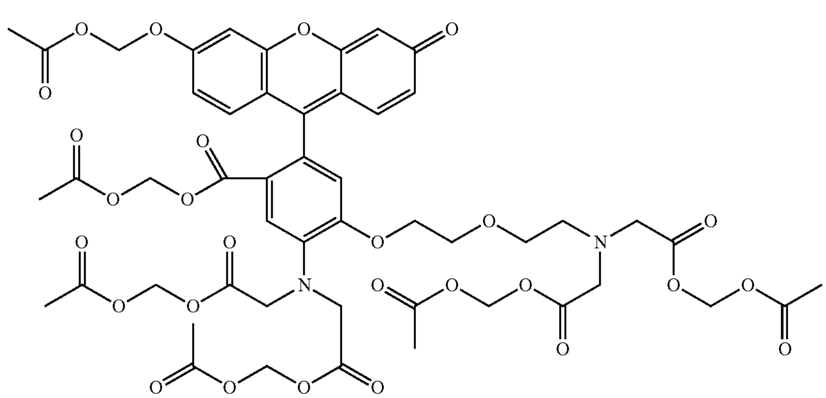 [SMILES: CC(=O)OCOC(=O)CN(CCOCCOc1cc(-c2c3ccc(=O)cc-3oc3cc(OCOC(C)=O)ccc23)c(C(=O)OCOC(C)=O)cc1N(CC(=O)OCOC(C)=O)CC(=O)OCOC(C)=O)CC(=O)OCOC(C)=O] |

77
78
TABLE 2-continued
Exemplary compounds of the present disclosure:
| Compound# | Structure |
|---|---|
| 132 | 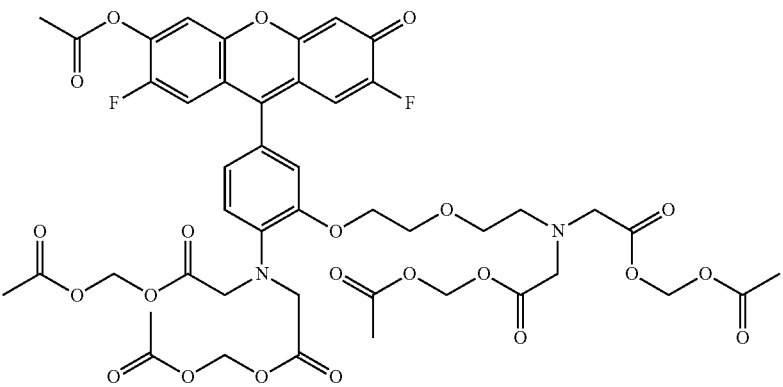 [SMILES: CC(=O)OCOC(=O)CN(CCOCCOc1cc(-c2c3cc(F)c(=O)cc-3oc3cc(OC(C)=O)c(F)cc23)ccc1N(CC(=O)OCOC(C)=O)CC(=O)OCOC(C)=O)CC(=O)OCOC(C)=O] |
| 133 | 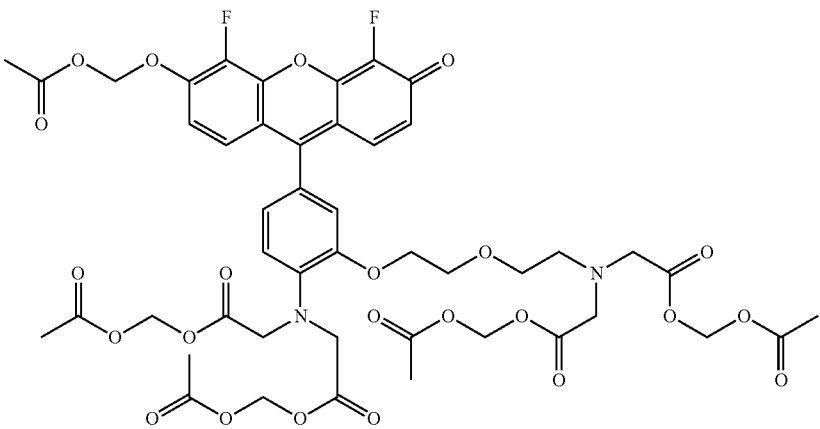 [SMILES: CC(=O)OCOC(=O)CN(CCOCCOc1cc(-c2c3ccc(=O)c(F)c-3oc3c(F)c(OCOC(C)=O)ccc23)ccc1N(CC(=O)OCOC(C)=O)CC(=O)OCOC(C)=O)CC(=O)OCOC(C)=O] |
| 134 | 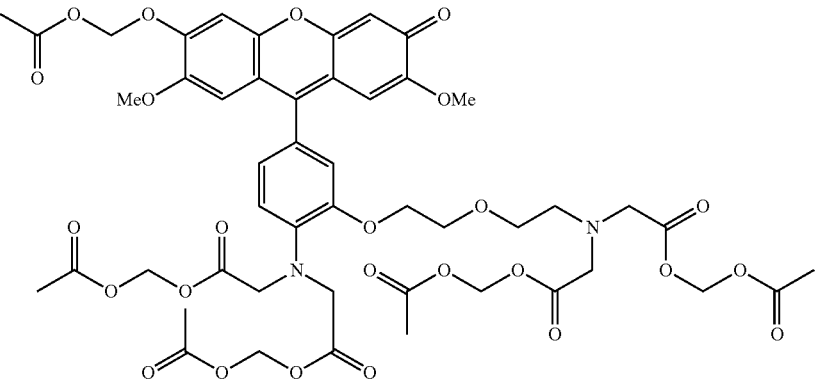 [SMILES: COc1cc2c(-c3ccc(N(CC(=O)OCOC(C)=O)CC(=O)OCOC(C)=O)c(OCCOCCN(CC(=O)OCOC(C)=O)CC(=O)OCOC(C)=O)c3)c3cc(OC)c(=O)cc-3oc2cc1OCOC(C)=O] |
| 135 | 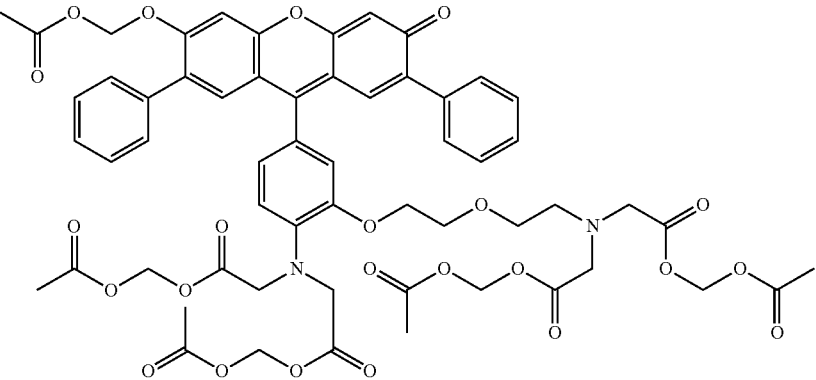 [SMILES: CC(=O)OCOC(=O)CN(CCOCCOc1cc(-c2c3cc(-c4ccccc4)c(=O)cc-3oc3cc(OCOC(C)=O)c(-c4ccccc4)cc23)ccc1N(CC(=O)OCOC(C)=O)CC(=O)OCOC(C)=O)CC(=O)OCOC(C)=O] |

TABLE 2-continued

Exemplary compounds of the present disclosure:

| Compound# | Structure |
|---|---|
| 136 | 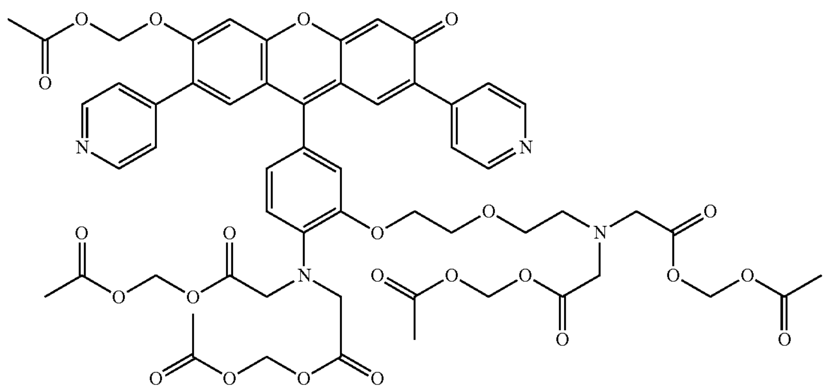 [SMILES: CC(=O)OCOC(=O)CN(CCOCCOc1cc(-c2c3cc(-c4ccncc4)c(=O)cc-3oc3cc(OCOC(C)=O)c(-c4ccncc4)cc23)ccc1N(CC(=O)OCOC(C)=O)CC(=O)OCOC(C)=O)CC(=O)OCOC(C)=O] |
| 137 | 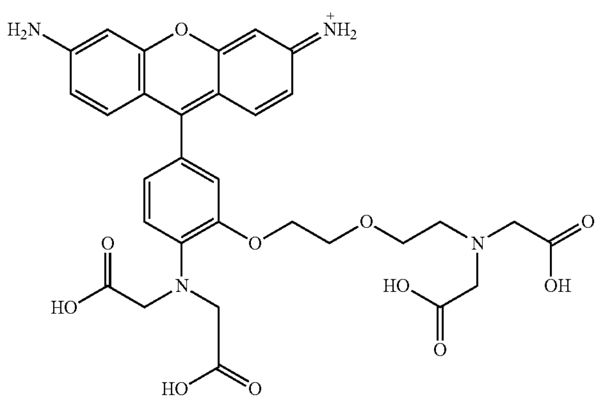 [SMILES: N=c1ccc2c(-c3ccc(N(CC(=O)O)CC(=O)O)c(OCCOCCN(CC(=O)O)CC(=O)O)c3)c3ccc(N)cc3oc-2c1] |
| 138 | 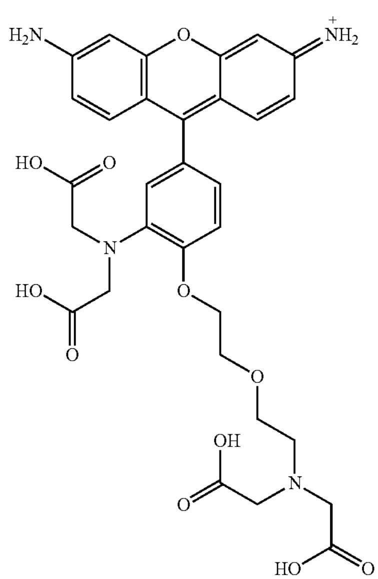 [SMILES: N=c1ccc2c(-c3ccc(OCCOCCN(CC(=O)O)CC(=O)O)c(N(CC(=O)O)CC(=O)O)c3)c3ccc(N)cc3oc-2c1] |

TABLE 2-continued
Exemplary compounds of the present disclosure:
| Compound# | Structure |
|---|---|
| 139 | 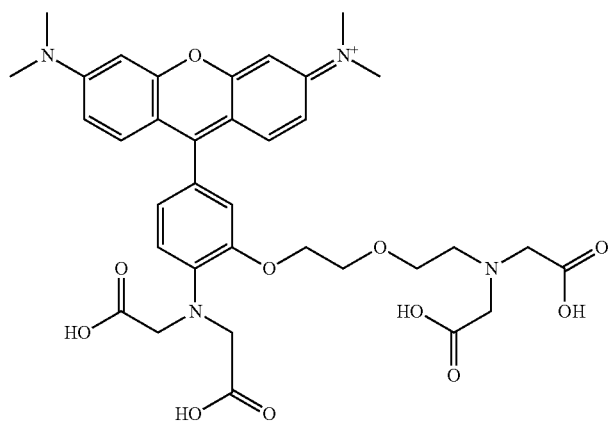 [SMILES: CN(C)c1ccc2c(-c3ccc(N(CC(=O)O)CC(=O)O)c(OCCOCCN(CC(=O)O)CC(=O)O)c3)c3ccc(=[N+](C)C)cc-3oc2c1] |
| 140 | 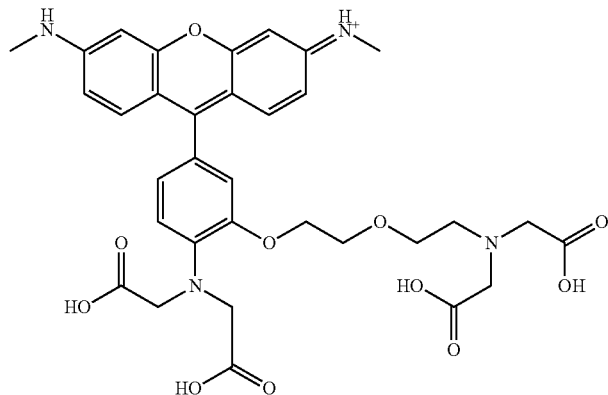 |
| 141 | 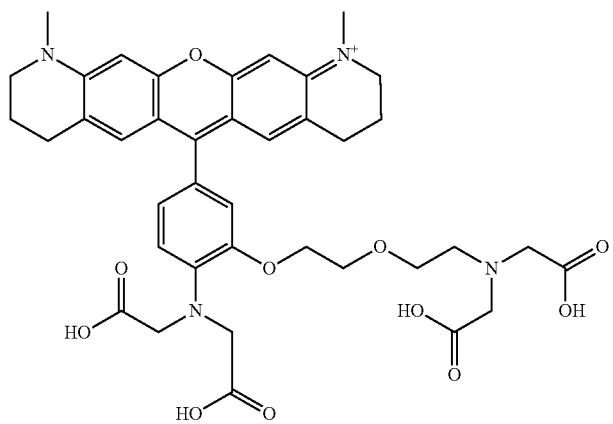 [SMILES: CN1CCCc2cc3c(cc21)Oc1cc2c(cc1=C3c1ccc(N(CC(=O)O)CC(=O)O)c(OCCOCCN(CC(=O)O)CC(=O)O)c1)CCC[N+]=2C] |

TABLE 2-continued
Exemplary compounds of the present disclosure:
| Compound# | Structure |
|---|---|
| 142 | 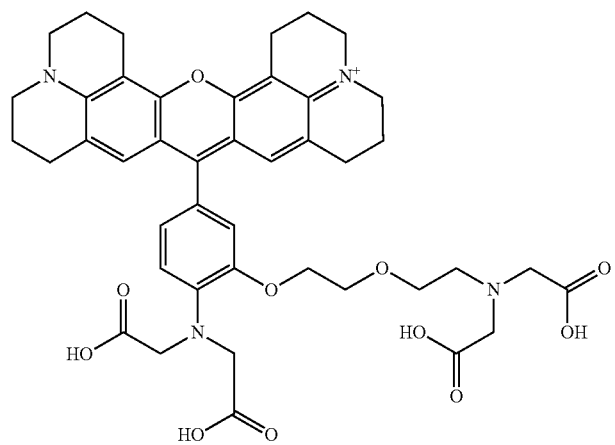 [SMILES: O=C(O)CN(CCOCCOc1cc(C2=c3cc4c5c(c3Oc3c2cc2c6c3CCCN6CCC2)CCC[N+]=5CCC4)ccc1N(CC(=O)O)CC(=O)O)CC(=O)O] |
| 143 | 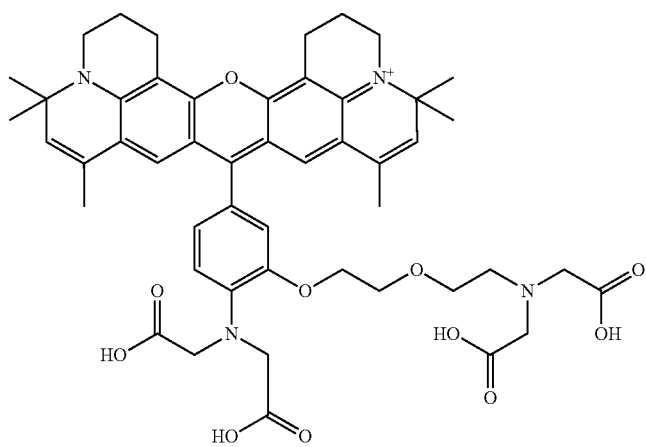 [SMILES: CC1=CC(C)(C)N2CCCc3c4c(cc1c32)C(c1ccc(N(CC(=O)O)CC(=O)O)c(OCCOCCN(CC(=O)O)CC(=O)O)c1)=c1cc2c3c(c1O4)CCC[N+]=3C(C)(C)C=C2C] |
| 145 | 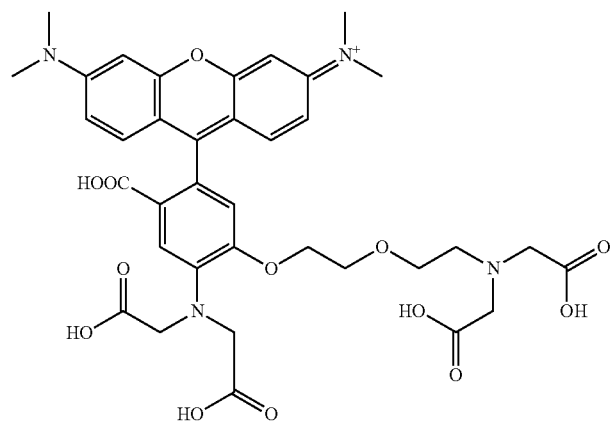 [SMILES: CN(C)c1ccc2c(-c3cc(OCCOCCN(CC(=O)O)CC(=O)O)c(N(CC(=O)O)CC(=O)O)cc3C(=O)O)c3ccc(=[N+](C)C)cc-3oc2c1] |

85 86
TABLE 2-continued
Exemplary compounds of the present disclosure:
| Compound# | Structure |
|---|---|
| 146 | 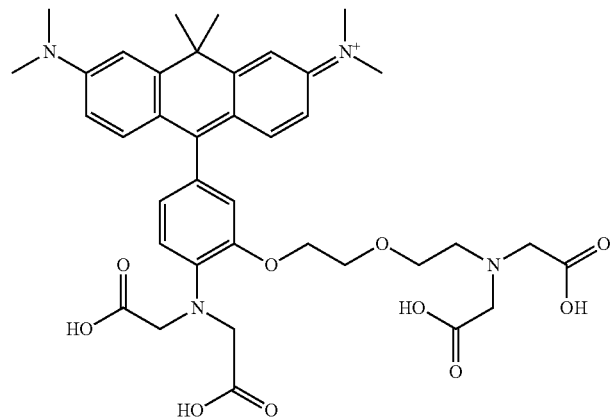 [SMILES: CN(C)c1ccc2c(c1)C(C)(C)C1=CC(=[N+](C)C)C=CC1=C2c1ccc(N(CC(=O)O)CC(=O)O)c(OCCOCCN(CC(=O)O)CC(=O)O)c1] |
| 147 | 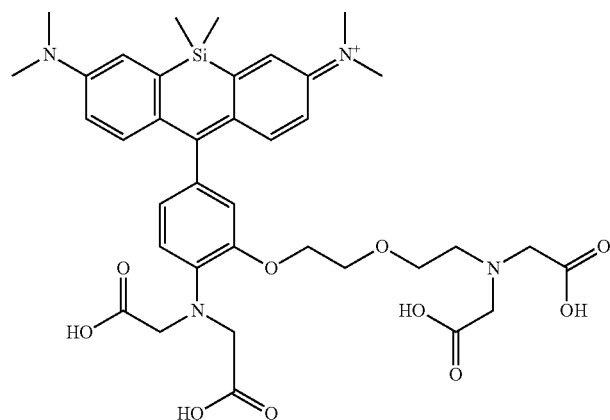 |
| 148 | 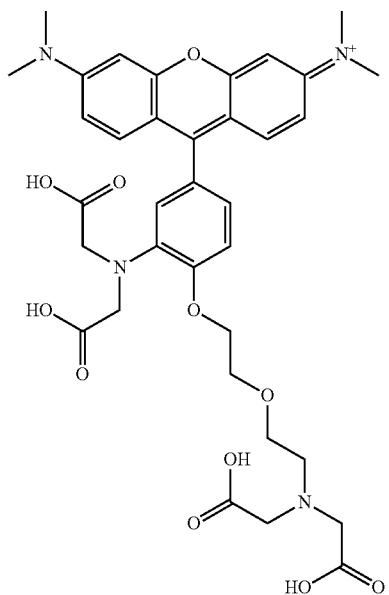 [SMILES: CN(C)c1ccc2c(-c3ccc(OCCOCCN(CC(=O)O)CC(=O)O)c(N(CC(=O)O)CC(=O)O)c3)c3ccc(=[N+](C)C)cc-3oc2c1] |

TABLE 2-continued
Exemplary compounds of the present disclosure:
| Compound# | Structure |
|---|---|
| 149 | 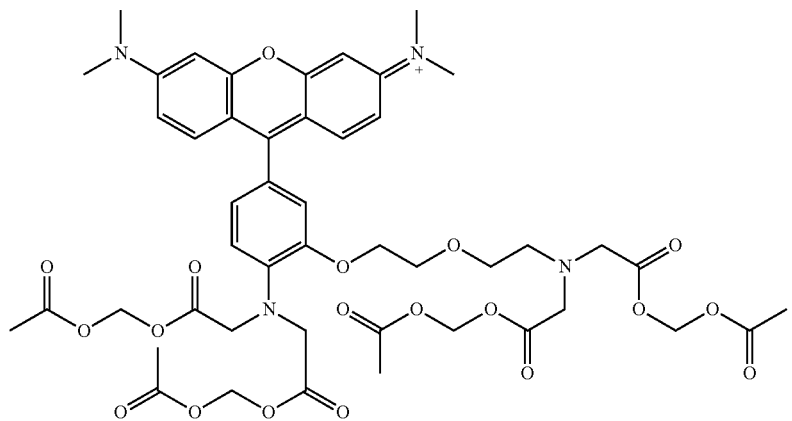 |
| 150 | 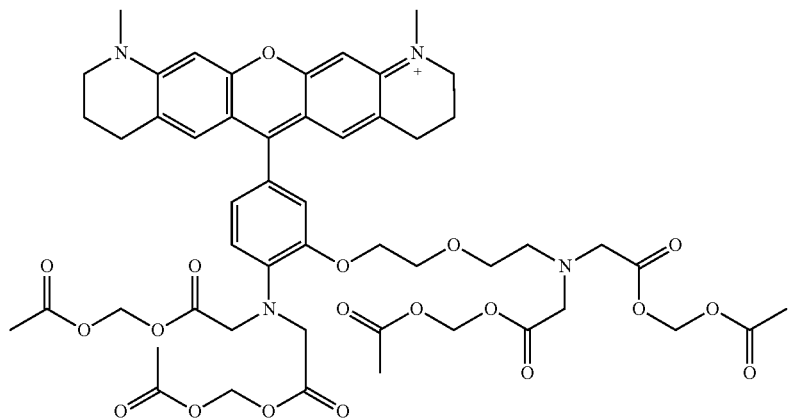 |
| 151 | 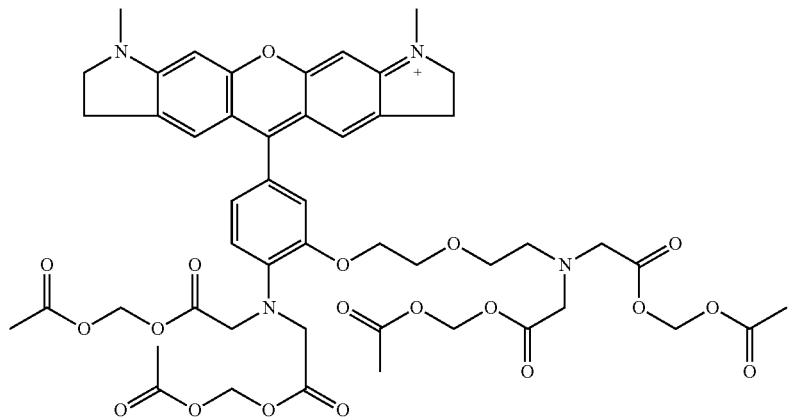 |

TABLE 2-continued
Exemplary compounds of the present disclosure:
| Compound# | Structure |
| --- | --- |
| 152 | 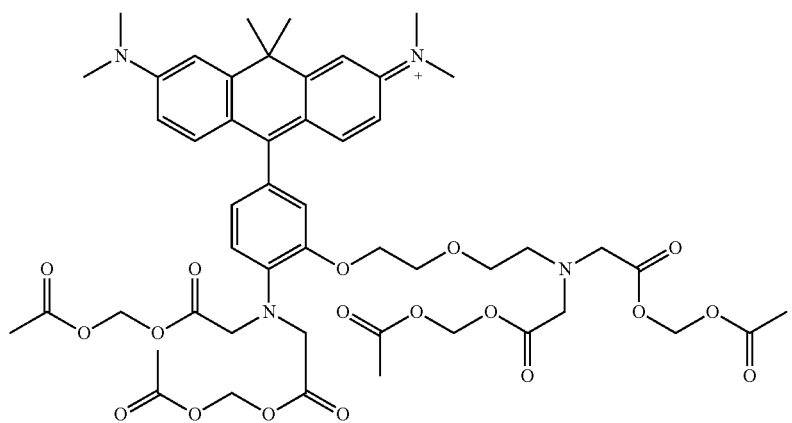 |
| 153 | 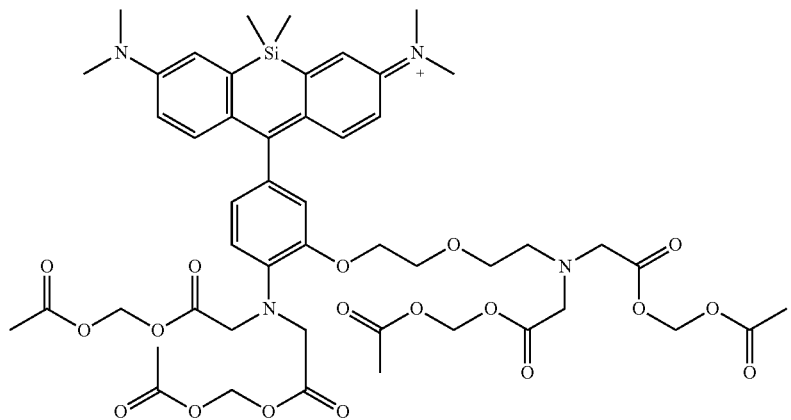 |
| 154 | 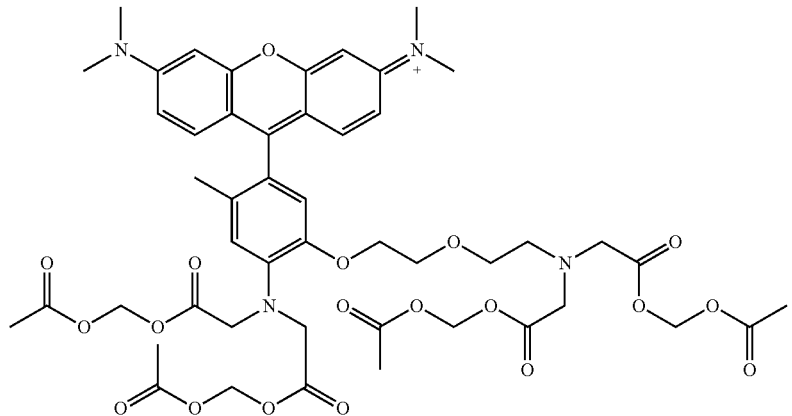 |

TABLE 2-continued
Exemplary compounds of the present disclosure:
| Compound# | Structure |
|---|---|
| 155 | 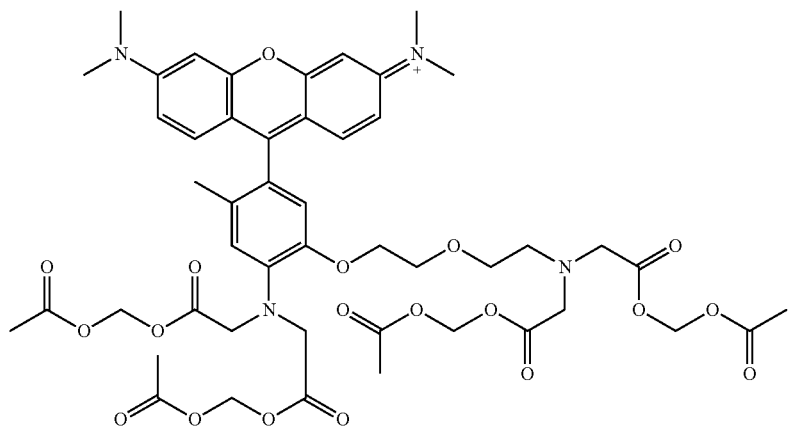 |
| 156 | 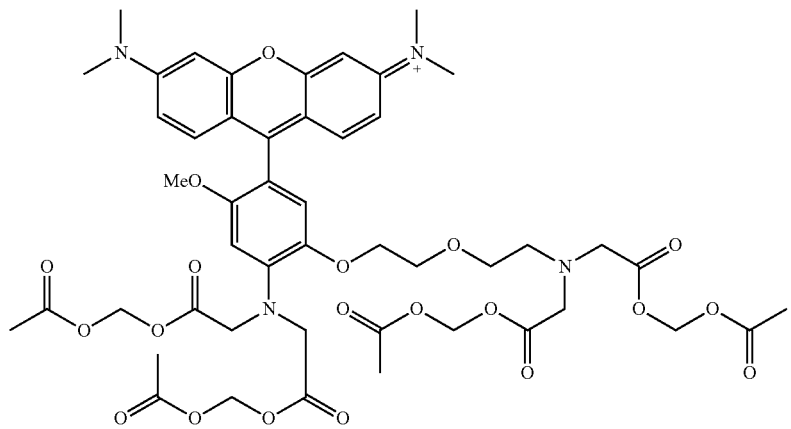 |
| 157 | 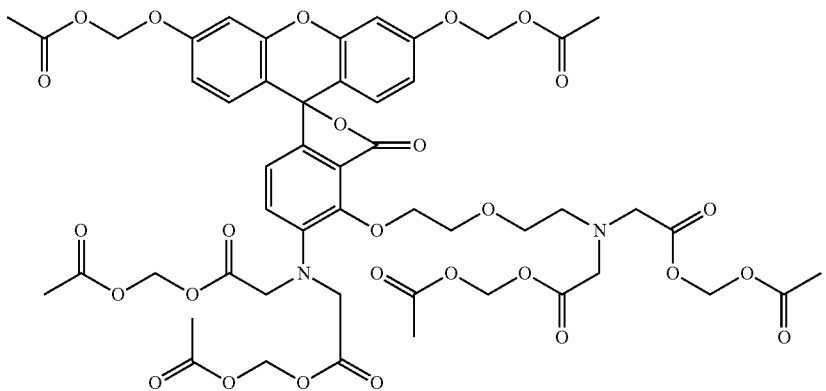 [SMILES: CC(=O)OCOC(=O)CN(CCOCCOc1c(N(CC(=O)OCOC(C)=O)CC(=O)OCOC(C)=O)ccc2c1C(=O)OC21c2ccc(OCOC(C)=O)cc2Oc2cc(OCOC(C)=O)ccc21)CC(=O)OCOC(C)=O] |

TABLE 2-continued

Exemplary compounds of the present disclosure:

| Compound# | Structure |
|---|---|
| 158 | 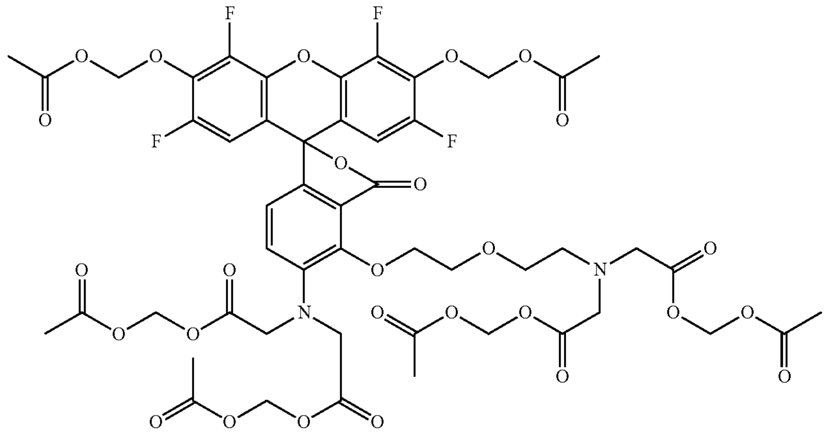 [SMILES: CC(=O)OCOC(=O)CN(CCOCCOc1c(N(CC(=O)OCOC(C)=O)CC(=O)OCOC(C)=O)ccc2c1C(=O)OC21c2cc(F)c(OCOC(C)=O)c(F)c2Oc2c1cc(F)c(OCOC(C)=O)c2F)CC(=O)OCOC(C)=O] |
| 159 | 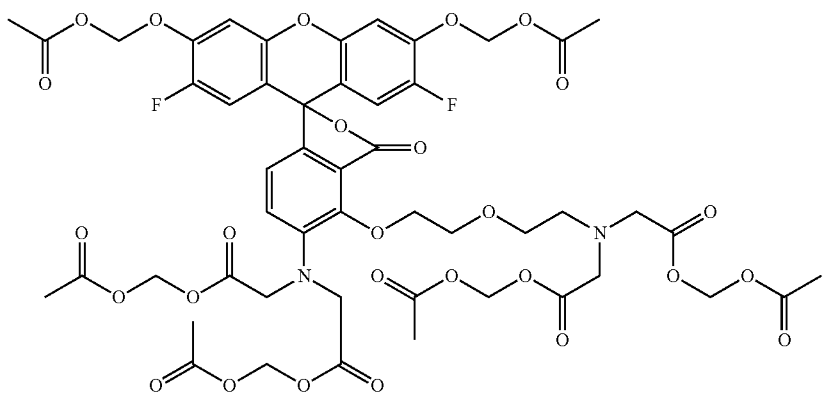 [SMILES: CC(=O)OCOC(=O)CN(CCOCCOc1c(N(CC(=O)OCOC(C)=O)CC(=O)OCOC(C)=O)ccc2c1C(=O)OC21c2cc(F)c(OCOC(C)=O)cc2Oc2cc(OCOC(C)=O)c(F)cc21)CC(=O)OCOC(C)=O] |
| 160 | 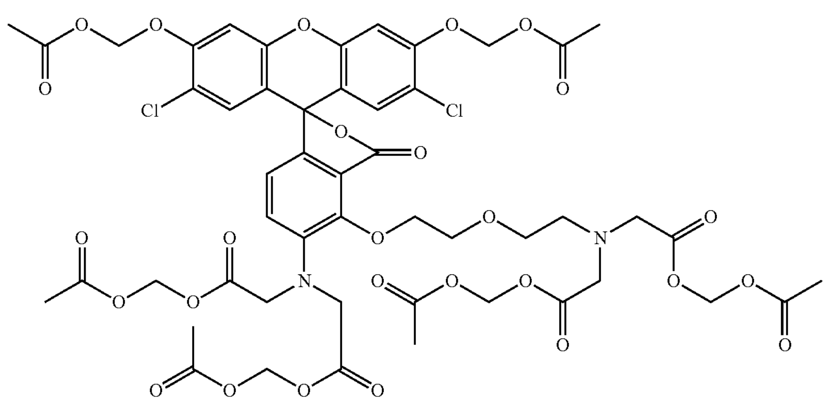 |

TABLE 2-continued
Exemplary compounds of the present disclosure:
| Compound# | Structure |
|---|---|
| 161 | 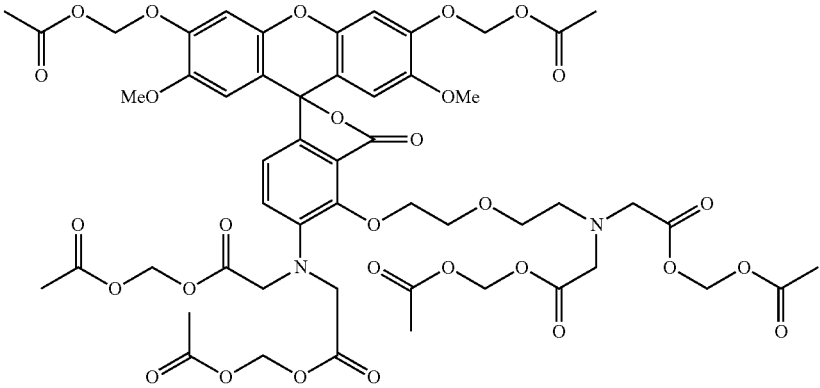 [SMILES: COc1cc2c(cc1OCOC(C)=O)Oc1cc(OCOC(C)=O)c(OC)cc1C21OC(=O)c2c1ccc(N(CC(=O)OCOC(C)=O)CC(=O)OCOC(C)=O)c2OCCOCCN(CC(=O)OCOC(C)=O)CC(=O)OCOC(C)=O] |
| 162 | 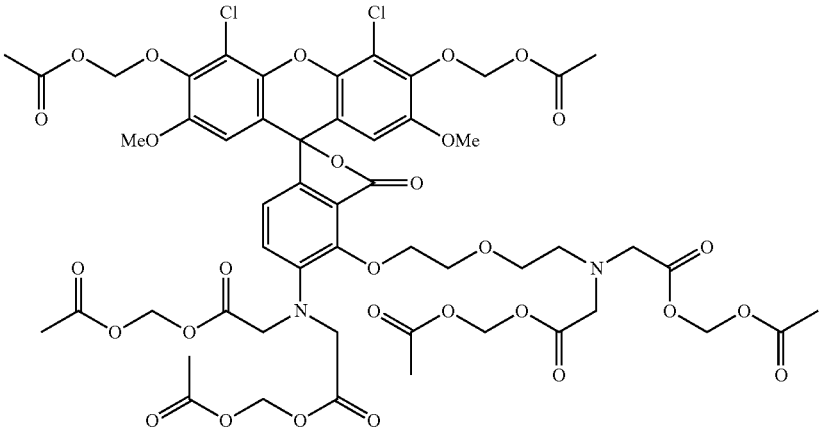 [SMILES: COc1cc2c(c(Cl)c1OCOC(C)=O)Oc1c(cc(OC)c(OCOC(C)=O)c1Cl)C21OC(=O)c2c1ccc(N(CC(=O)OCOC(C)=O)CC(=O)OCOC(C)=O)c2OCCOCCN(CC(=O)OCOC(C)=O)CC(=O)OCOC(C)=O] |
| 163 | 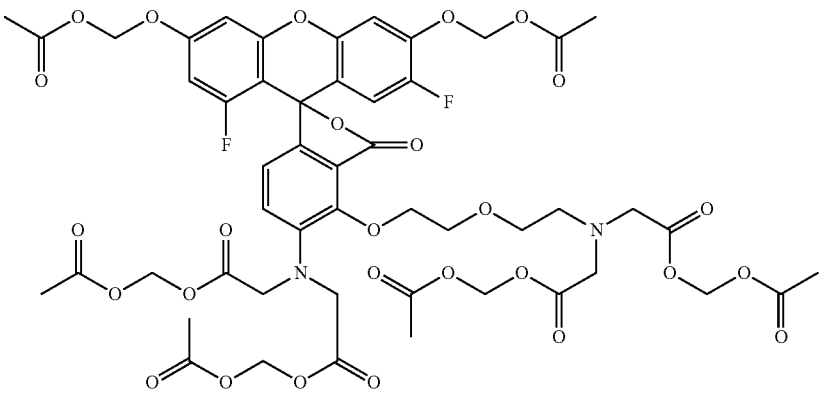 [SMILES: CC(=O)OCOC(=O)CN(CCOCCOc1c(N(CC(=O)OCOC(C)=O)CC(=O)OCOC(C)=O)ccc2c1C(=O)OC21c2cc(F)c(OCOC(C)=O)cc2Oc2cc(OCOC(C)=O)cc(F)c21)CC(=O)OCOC(C)=O] |

TABLE 2-continued
Exemplary compounds of the present disclosure:
| Compound# | Structure |
|---|---|
| 164 | 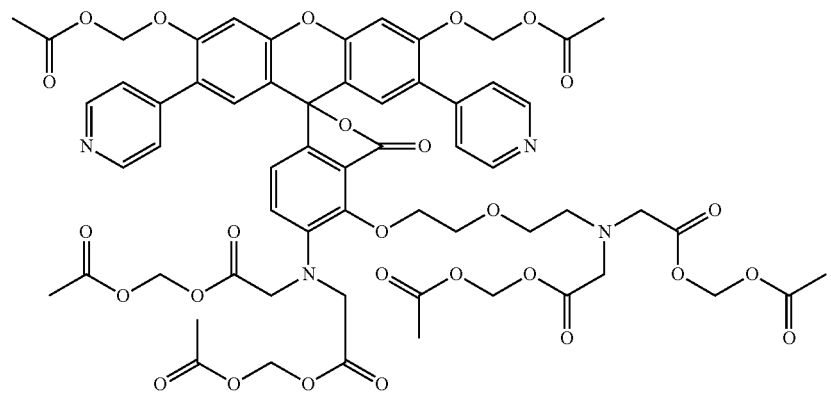 [SMILES: CC(=O)OCOC(=O)CN(CCOCCOc1c(N(CC(=O)OCOC(C)=O)CC(=O)OCOC(C)=O)ccc2c1C(=O)OC21c2cc(-c3ccncc3)c(OCOC(C)=O)cc2Oc2cc(OCOC(C)=O)c(-c3ccncc3)cc21)CC(=O)OCOC(C)=O] |
| 165 | 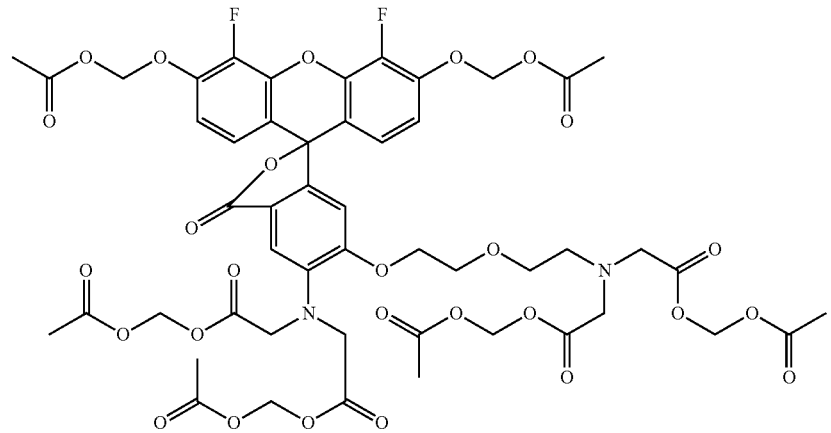 [SMILES: CC(=O)OCOC(=O)CN(CCOCCOc1cc2c(cc1N(CC(=O)OCOC(C)=O)CC(=O)OCOC(C)=O)C(=O)OC21c2ccc(OCOC(C)=O)c(F)c2Oc2c1ccc(OCOC(C)=O)c2F)CC(=O)OCOC(C)=O] |
| 166 | 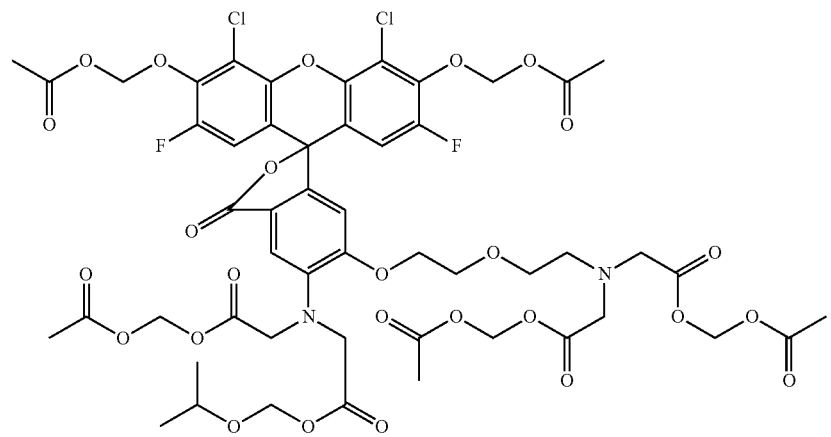 [SMILES: CC(=O)OCOC(=O)CN(CCOCCOc1cc2c(cc1N(CC(=O)OCOC(C)=O)CC(=O)OCOC(C)C)C(=O)OC21c2cc(F)c(OCOC(C)=O)c(Cl)c2Oc2c1cc(F)c(OCOC(C)=O)c2Cl)CC(=O)OCOC(C)=O] |

TABLE 2-continued
Exemplary compounds of the present disclosure:
| Compound# | Structure |
|---|---|
| 167 | 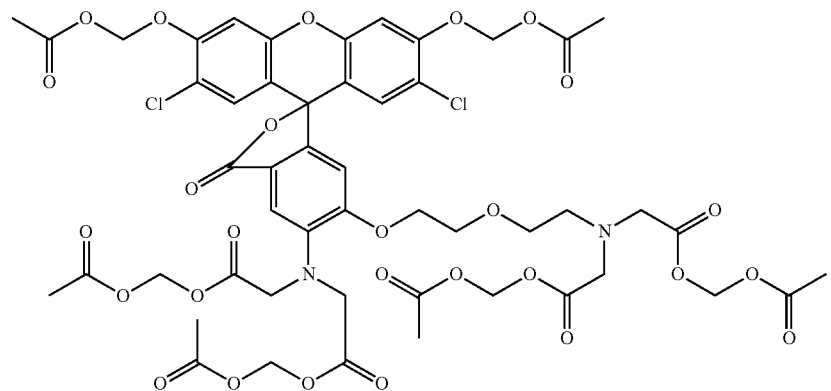 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OCOC(C)=O)cc2Oc2cc(OCOC(C)=O)c(Cl)cc21)CC(=O)OCOC(C)=O] |
| 168 | 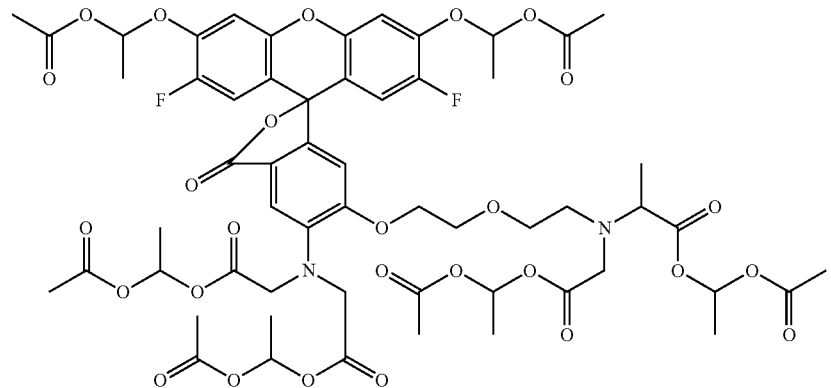 [SMILES: CC(=O)OC(C)OC(=O)CN(CC(=O)OC(C)OC(C)=O)c1cc2c(cc1OCCOCCN(CC(=O)OC(C)OC(C)=O)C(C)C(=O)OC(C)OC(C)=O)C1(OC2=O)c2cc(F)c(OC(C)OC(C)=O)cc2Oc2cc(OC(C)OC(C)=O)c(F)cc21] |
| 169 | 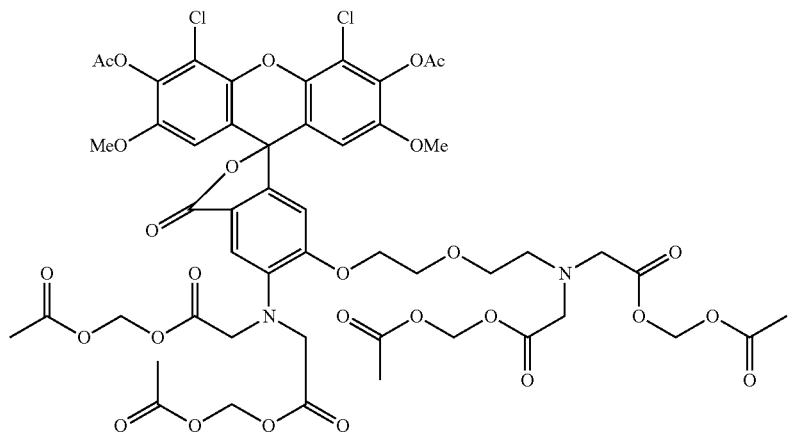 [SMILES: COc1cc2c(c(Cl)c1OC(C)=O)Oc1c(cc(OC)c(OC(C)=O)c1Cl)C21OC(=O)c2cc(N(CC(=O)OCOC(C)=O)CC(=O)OCOC(C)=O)c(OCCOCCN(CC(=O)OCOC(C)=O)CC(=O)OCOC(C)=O)cc21] |

TABLE 2-continued
Exemplary compounds of the present disclosure:
| Compound# | Structure |
|---|---|
| 170 | 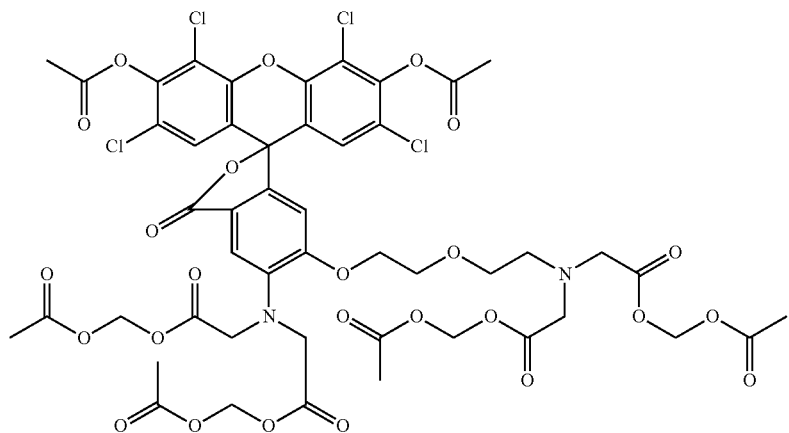 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OC(C)=O)c(Cl)c2Oc2c1cc(Cl)c(OC(C)=O)c2Cl)CC(=O)OCOC(C)=O] |
| 171 | 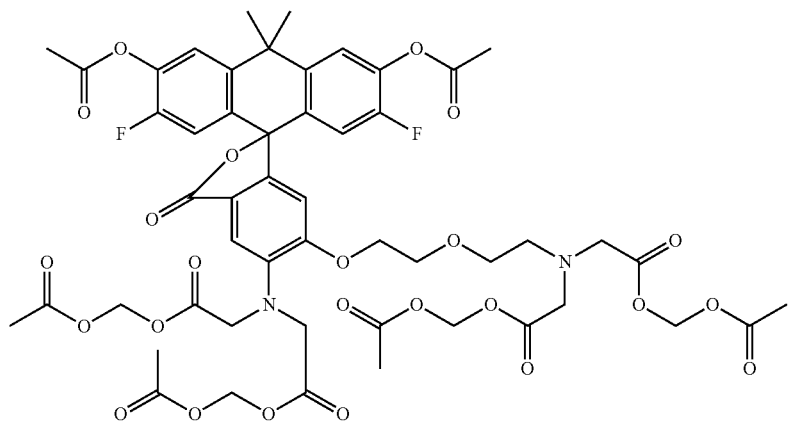 [SMILES: CC(=O)OCOC(=O)CN(CCOCCOc1cc2c(cc1N(CC(=O)OCOC(C)=O)CC(=O)OCOC(C)=O)C(=O)OC21c2cc(F)c(OC(C)=O)cc2C(C)(C)c2cc(OC(C)=O)c(F)cc21)CC(=O)OCOC(C)=O] |
| 172 | 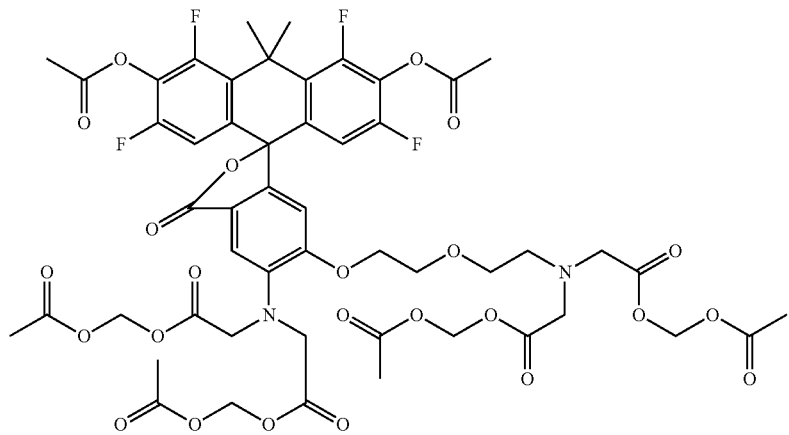 [SMILES: CC(=O)OCOC(=O)CN(CCOCCOc1cc2c(cc1N(CC(=O)OCOC(C)=O)CC(=O)OCOC(C)=O)C(=O)OC21c2cc(F)c(OC(C)=O)c(F)c2C(C)(C)c2c1cc(F)c(OC(C)=O)c2F)CC(=O)OCOC(C)=O] |

103
104
TABLE 2-continued
Exemplary compounds of the present disclosure:
| Compound# | Structure |
|---|---|
| 173 | 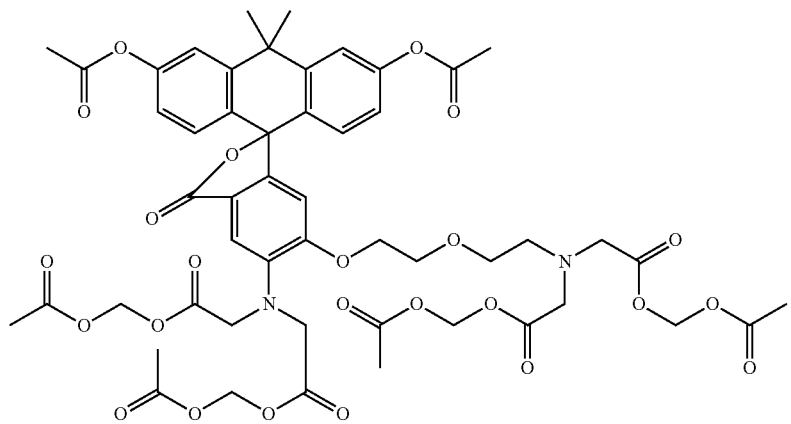 [SMILES: CC(=O)OCOC(=O)CN(CCOCCOc1cc2c(cc1N(CC(=O)OCOC(C)=O)CC(=O)OCOC(C)=O)C(=O)OC21c2ccc(OC(C)=O)cc2C(C)(C)c2cc(OC(C)=O)ccc21)CC(=O)OCOC(C)=O] |
| 174 | 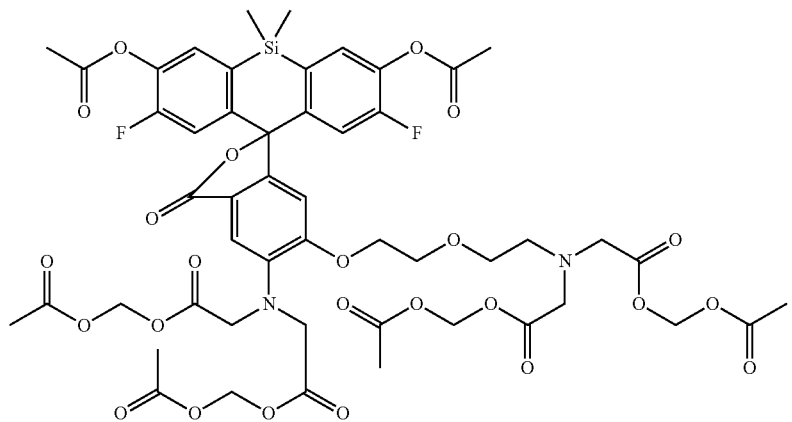 [SMILES: CC(=O)OCOC(=O)CN(CCOCCOc1cc2c(cc1N(CC(=O)OCOC(C)=O)CC(=O)OCOC(C)=O)C(=O)OC21c2cc(F)c(OC(C)=O)cc2[Si](C)(C)c2cc(OC(C)=O)c(F)cc21)CC(=O)OCOC(C)=O] |
| 175 | 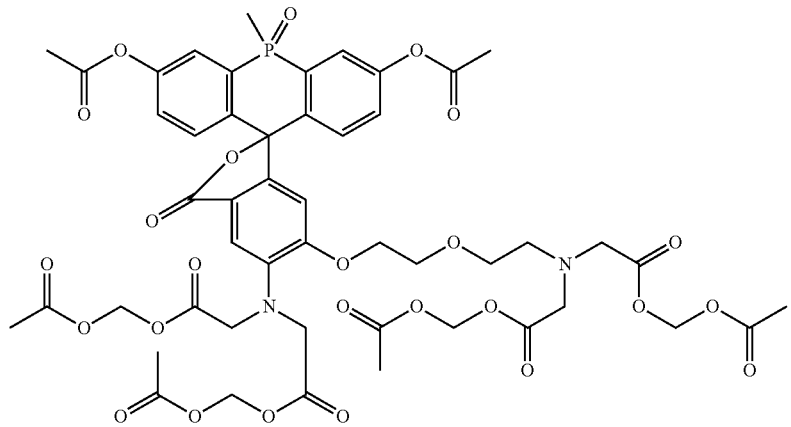 [SMILES: CC(=O)OCOC(=O)CN(CCOCCOc1cc2c(cc1N(CC(=O)OCOC(C)=O)CC(=O)OCOC(C)=O)C(=O)OC21c2ccc(OC(C)=O)cc2P(C)(=O)c2cc(OC(C)=O)ccc21)CC(=O)OCOC(C)=O] |

TABLE 2-continued
Exemplary compounds of the present disclosure:
| Compound# | Structure |
|---|---|
| 176 | 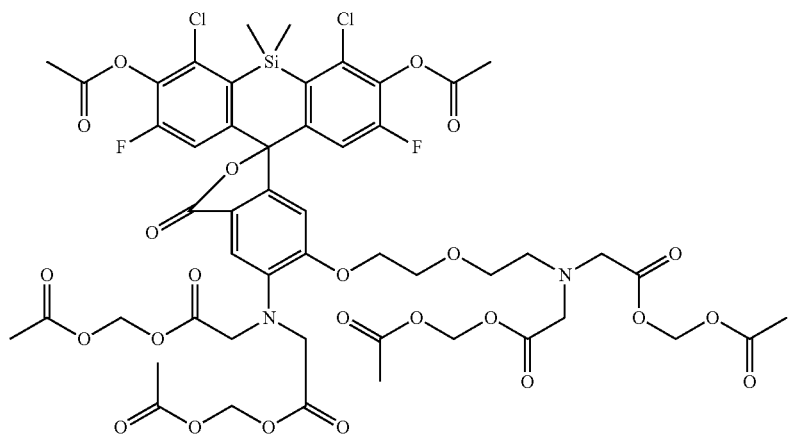 [SMILES: CC(=O)OCOC(=O)CN(CCOCCOc1cc2c(cc1N(CC(=O)OCOC(C)=O)CC(=O)OCOC(C)=O)C(=O)OC21c2cc(F)c(OC(C)=O)c(Cl)c2[Si](C)(C)c2c1cc(F)c(OC(C)=O)c2Cl)CC(=O)OCOC(C)=O] |
| 177 | 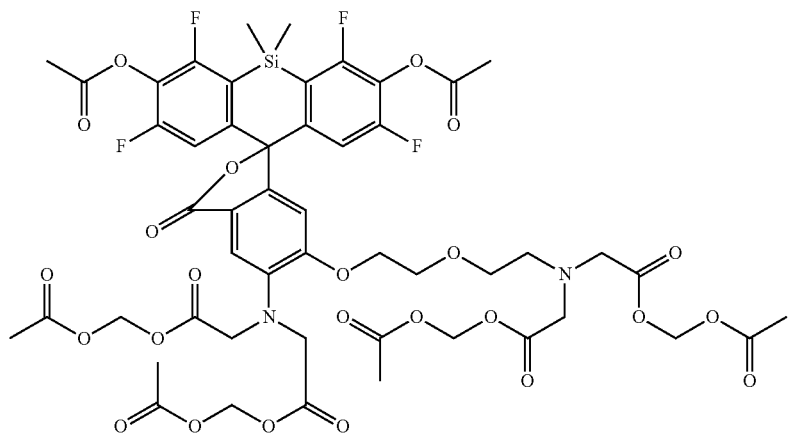 |
| 178 | 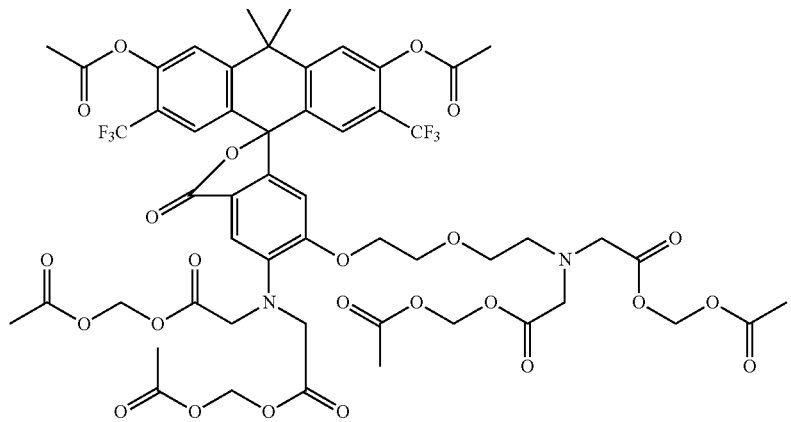 [SMILES: CC(=O)OCOC(=O)CN(CCOCCOc1cc2c(cc1N(CC(=O)OCOC(C)=O)CC(=O)OCOC(C)=O)C(=O)OC21c2cc(C(F)(F)F)c(OC(C)=O)cc2C(C)(C)c2cc(OC(C)=O)c(C(F)(F)F)cc21)CC(=O)OCOC(C)=O] |

TABLE 2-continued
Exemplary compounds of the present disclosure:
| Compound# | Structure |
|---|---|
| 179 | 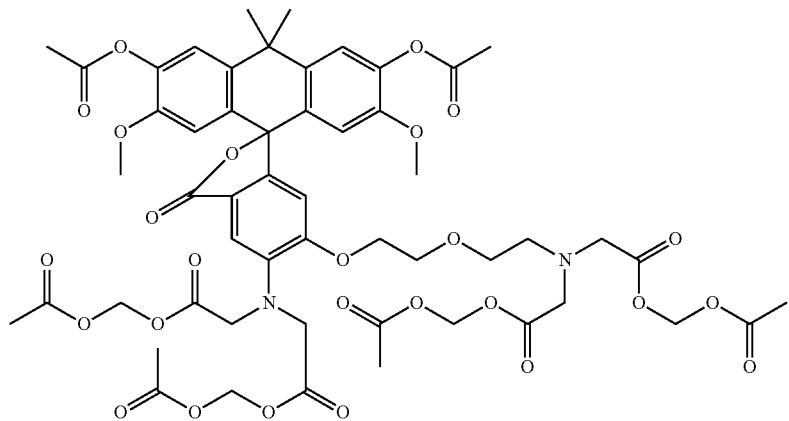 [SMILES: COc1cc2c(cc1OC(C)=O)C(C)(C)c1cc(OC(C)=O)c(OC)cc1C21OC(=O)c2cc(N(CC(=O)OCOC(C)=O)CC(=O)OCOC(C)=O)c(OCCOCCN(CC(=O)OCOC(C)=O)CC(=O)OCOC(C)=O)cc21] |
| 180 | 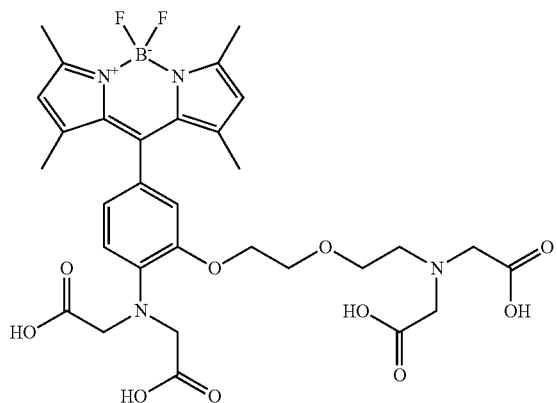 [SMILES: CC1=CC(C)=[N+]2C1=C(c1ccc(N(CC(=O)O)CC(=O)O)c(OCCOCCN(CC(=O)O)CC(=O)O)c1)c1c(C)cc(C)n1[B-]2(F)F] |
| 181 | 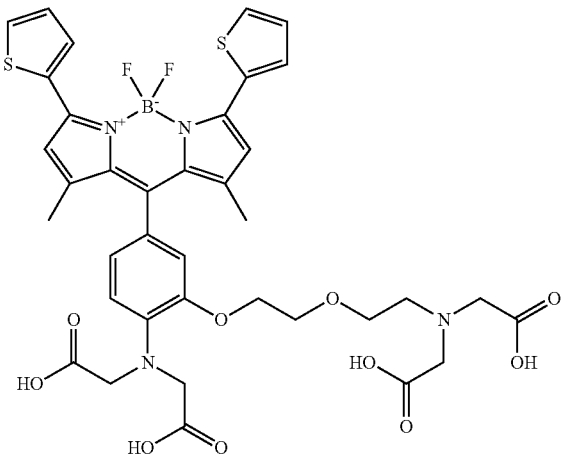 [SMILES: CC1=CC(c2cccs2)=[N+]2C1=C(c1ccc(N(CC(=O)O)CC(=O)O)c(OCCOCCN(CC(=O)O)CC(=O)O)c1)c1c(C)cc(-c3cccs3)n1[B-]2(F)F] |

TABLE 2-continued

Exemplary compounds of the present disclosure:

| Compound# | Structure |
|---|---|
| 182 | 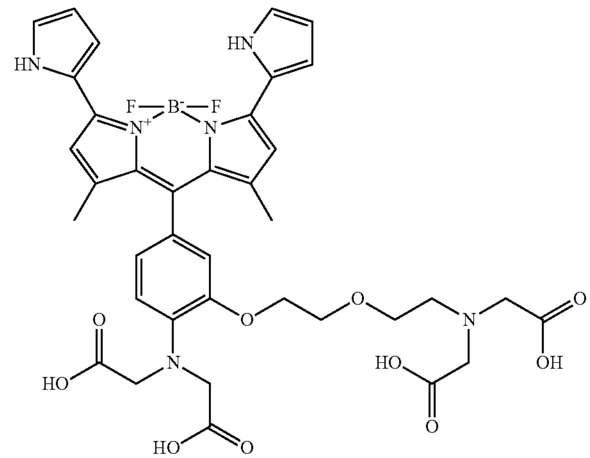 [SMILES: CC1=CC(c2ccc[nH]2)=[N+]2C1=C(c1ccc(N(CC(=O)O)CC(=O)O)c(OCCOCCN(CC(=O)O)CC(=O)O)c1)c1c(C)cc(-c3ccc[nH]3)n1[B-]2(F)F] |
| 183 | 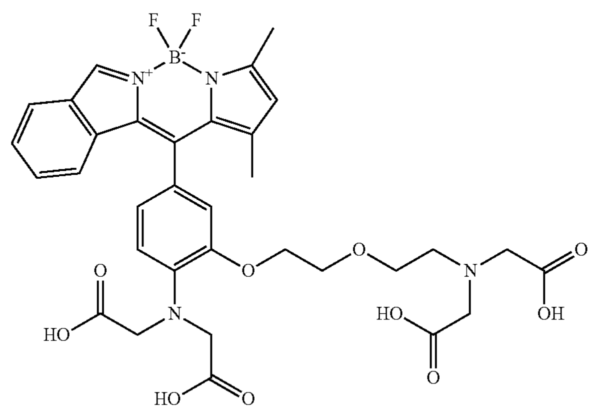 [SMILES: Cc1cc(C)n2c1C(c1ccc(N(CC(=O)O)CC(=O)O)c(OCCOCCN(CC(=O)O)CC(=O)O)c1)=C1c3ccccc3C=[N+]1[B-]2(F)F] |
| 184 | 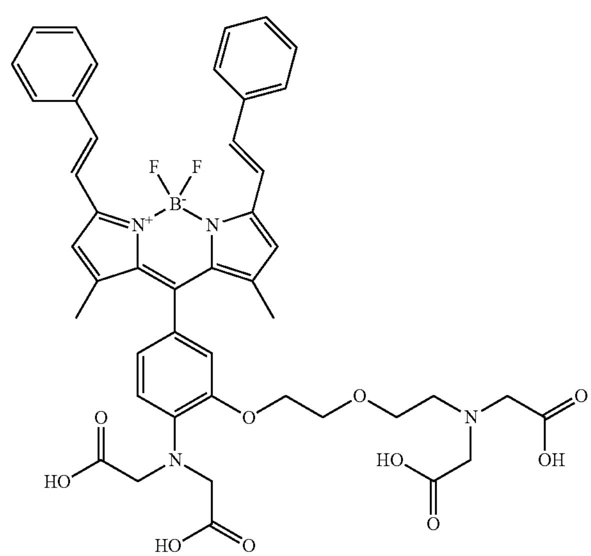 [SMILES: CC1=CC(/C=C/c2ccccc2)=[N+]2C1=C(c1ccc(N(CC(=O)O)CC(=O)O)c(OCCOCCN(CC(=O)O)CC(=O)O)c1)c1c(C)cc(/C=C/c3ccccc3)n1[B-]2(F)F] |

TABLE 2-continued
Exemplary compounds of the present disclosure:
| Compound# | Structure |
|---|---|
| 185 | 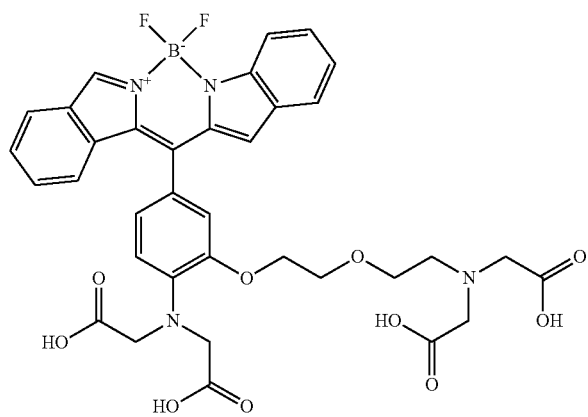 [SMILES: O=C(O)CN(CCOCCOc1cc(C2=C3c4ccccc4C=[N+]3[B-](F)(F)n3c2cc2ccccc23)ccc1N(CC(=O)O)CC(=O)O)CC(=O)O] |
| 186 | 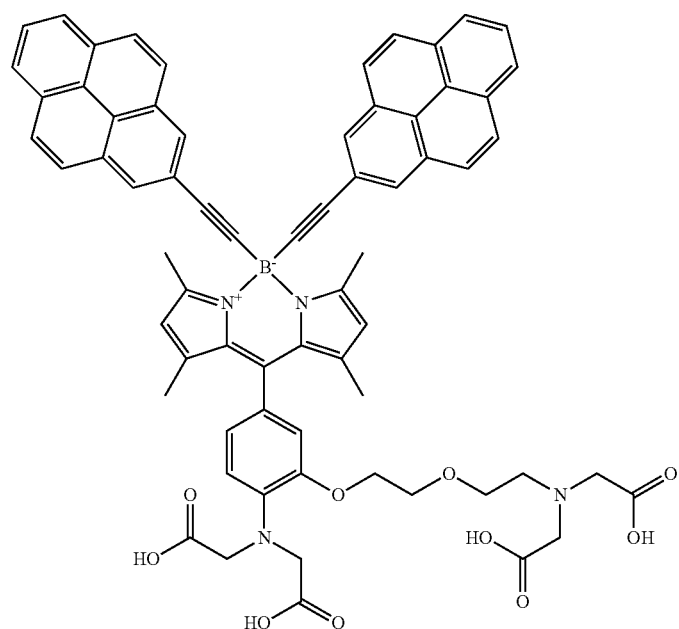 [SMILES: CC1=CC(C)=[N+]2C1=C(c1ccc(N(CC(=O)O)CC(=O)O)c(OCCOCCN(CC(=O)O)CC(=O)O)c1)c1c(C)cc(C)n1[B-]2(C#Cc1cc2ccc3cccc4ccc(c1)c2c34)C#Cc1cc2ccc3cccc4ccc(c1)c2c34] |
| 187 | 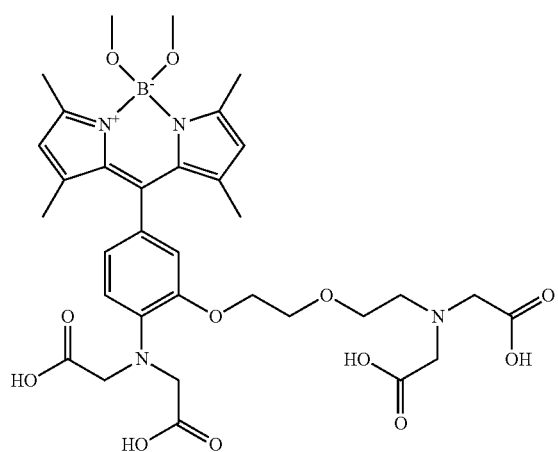 [SMILES: CO[B-]1(OC)n2c(C)cc(C)c2C(c2ccc(N(CC(=O)O)CC(=O)O)c(OCCOCCN(CC(=O)O)CC(=O)O)c2)=C2C(C)=CC(C)=[N+]21] |

TABLE 2-continued
Exemplary compounds of the present disclosure:
| Compound# | Structure |
| --- | --- |
| 188 | 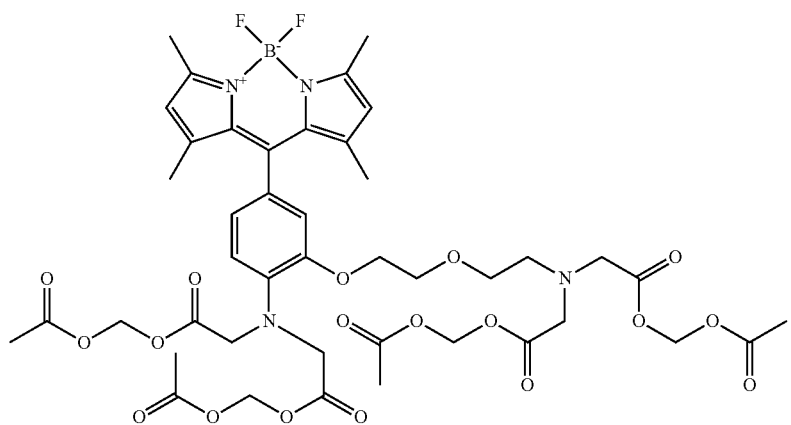 [SMILES: CC(=O)OCOC(=O)CN(CCOCCOc1cc(C2=C3C(C)=CC(C)=[N+]3[B-](F)(F)n3c(C)cc(C)c32)ccc1N(CC(=O)OCOC(C)=O)CC(=O)OCOC(C)=O)CC(=O)OCOC(C)=O] |
| 189 | 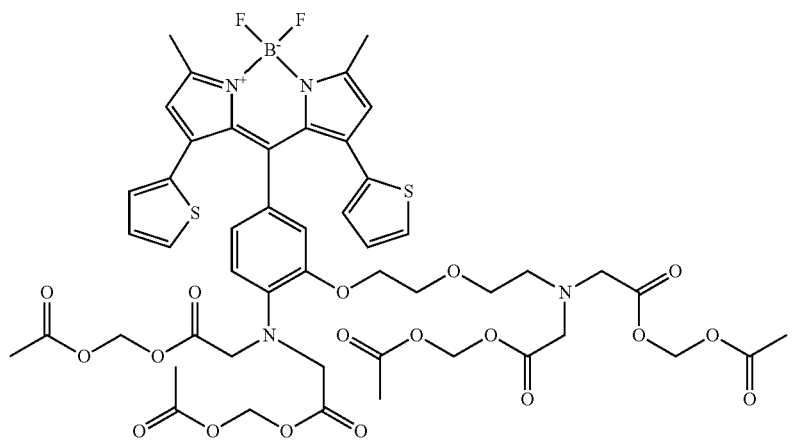 [SMILES: CC(=O)OCOC(=O)CN(CCOCCOc1cc(C2=C3C(c4cccs4)=CC(C)=[N+]3[B-](F)(F)n3c(C)cc(-c4cccs4)c32)ccc1N(CC(=O)OCOC(C)=O)CC(=O)OCOC(C)=O)CC(=O)OCOC(C)=O] |
| 190 | 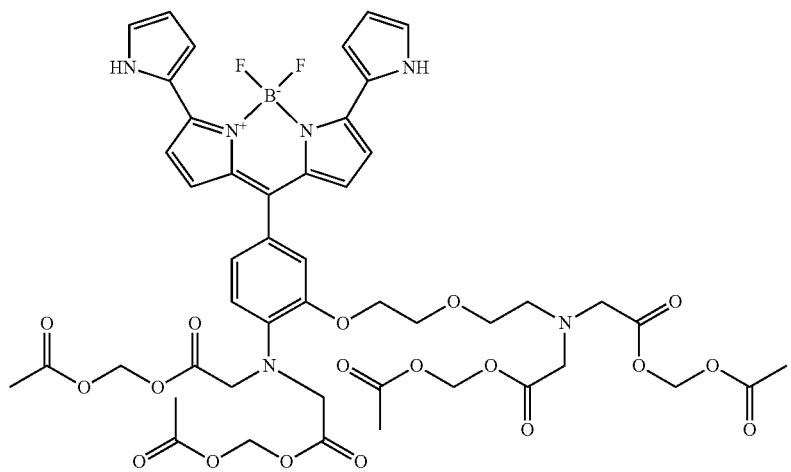 [SMILES: CC(=O)OCOC(=O)CN(CCOCCOc1cc(C2=C3C=CC(c4ccc[nH]4)=[N+]3[B-](F)(F)n3c2ccc3-c2ccc[nH]2)ccc1N(CC(=O)OCOC(C)=O)CC(=O)OCOC(C)=O)CC(=O)OCOC(C)=O] |

TABLE 2-continued
Exemplary compounds of the present disclosure:
| Compound# | Structure |
|---|---|
| 191 | 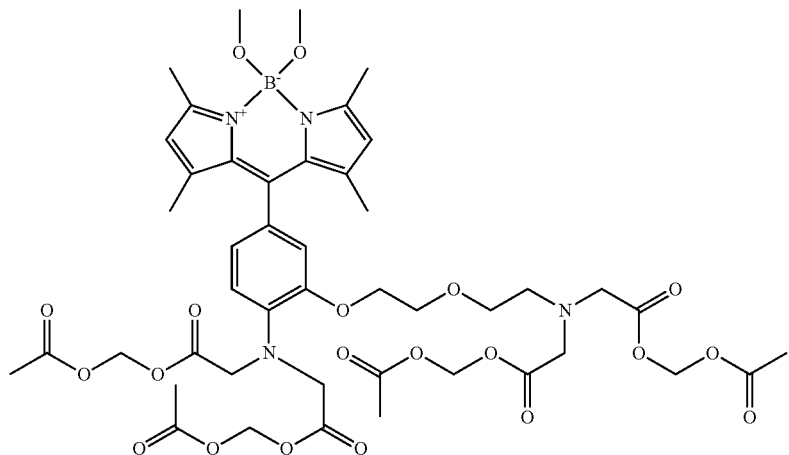 [SMILES: CO[B-]1(OC)n2c(C)cc(C)c2C(c2ccc(N(CC(=O)OCOC(C)=O)CC(=O)OCOC(C)=O)c(OCCOCCN(CC(=O)OCOC(C)=O)CC(=O)OCOC(C)=O)c2)=C2C(C)=CC(C)=[N+]21] |
| 192 | 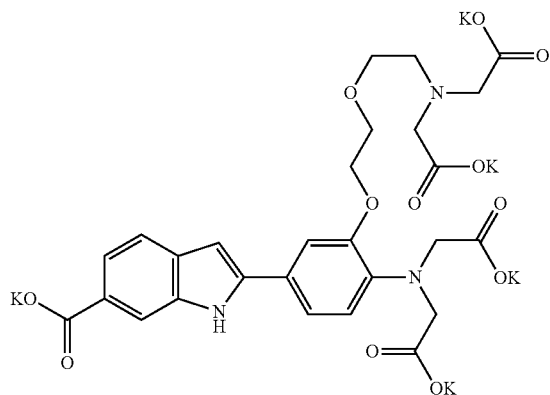 |
| 193 | 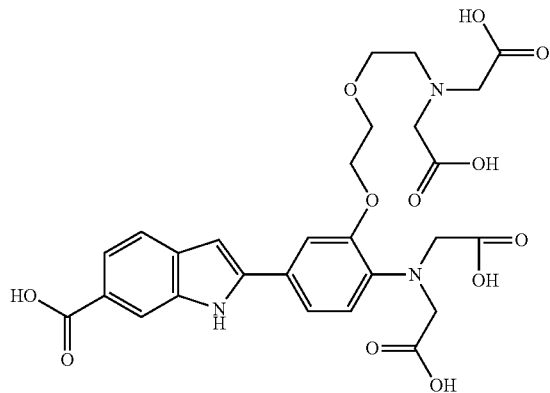 [SMILES: O=C(O)CN(CCOCCOc1cc(-c2cc3ccc(C(=O)O)cc3[nH]2)ccc1N(CC(=O)O)CC(=O)O)CC(=O)O] |

TABLE 2-continued
Exemplary compounds of the present disclosure:
| Compound# | Structure |
|---|---|
| 194 | 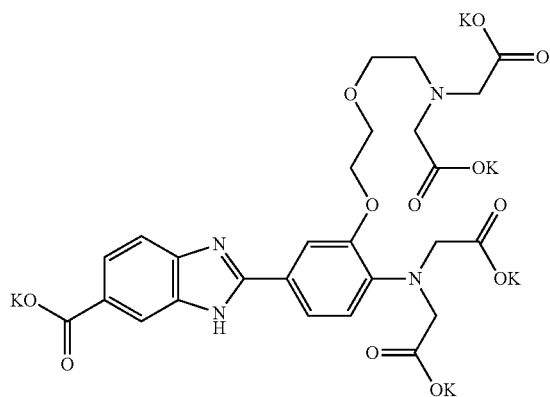 |
| 195 | 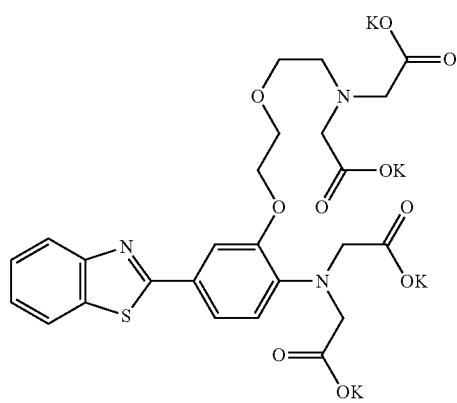 |
| 196 | 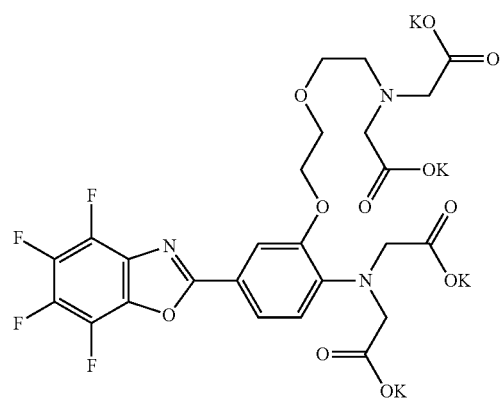 |

TABLE 2-continued
Exemplary compounds of the present disclosure:
| Compound# | Structure |
|---|---|
| 197 | 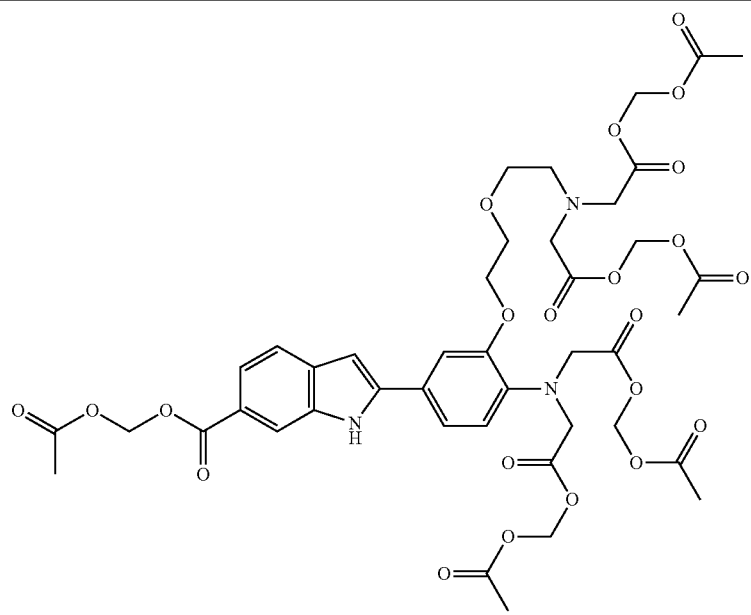 |
| 198 | 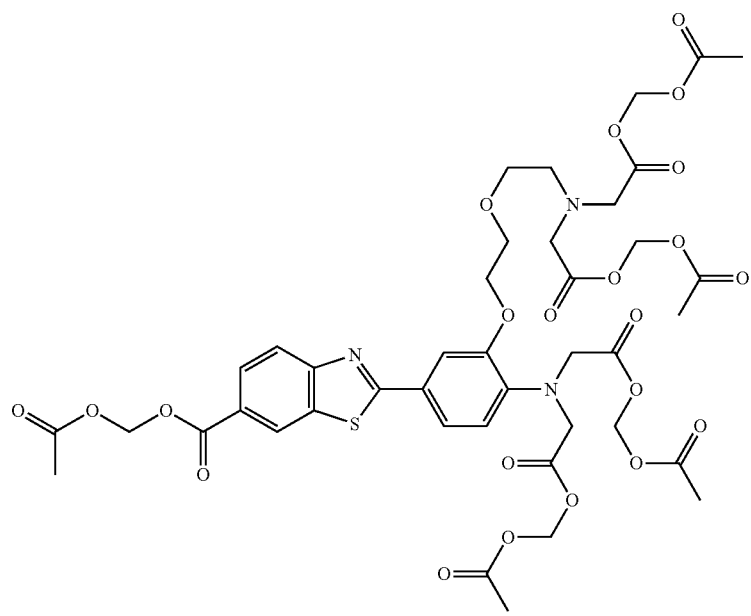 [SMILES: CC(=O)OCOC(=O)CN(CCOCCOc1cc(-c2nc3ccc(C(=O)OCOC(C)=O)cc3s2)ccc1N(CC(=O)OCOC(C)=O)CC(=O)OCOC(C)=O)CC(=O)OCOC(C)=O] |
| 199 | 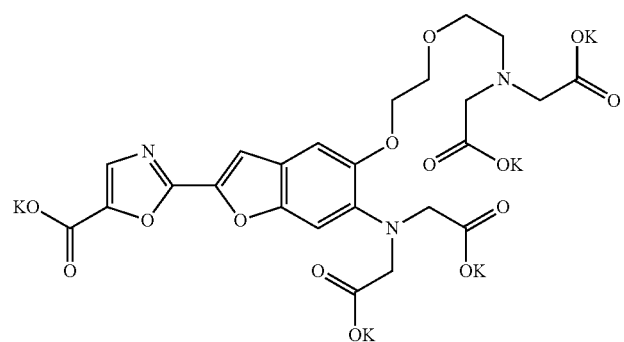 |

TABLE 2-continued

Exemplary compounds of the present disclosure:

| Compound# | Structure |
|---|---|
| 200 | (structure) |
| 201 | (structure) |
| 202 | (structure) |
| 203 | (structure) |

TABLE 2-continued
Exemplary compounds of the present disclosure:
| Compound# | Structure |
|---|---|
| 204 | 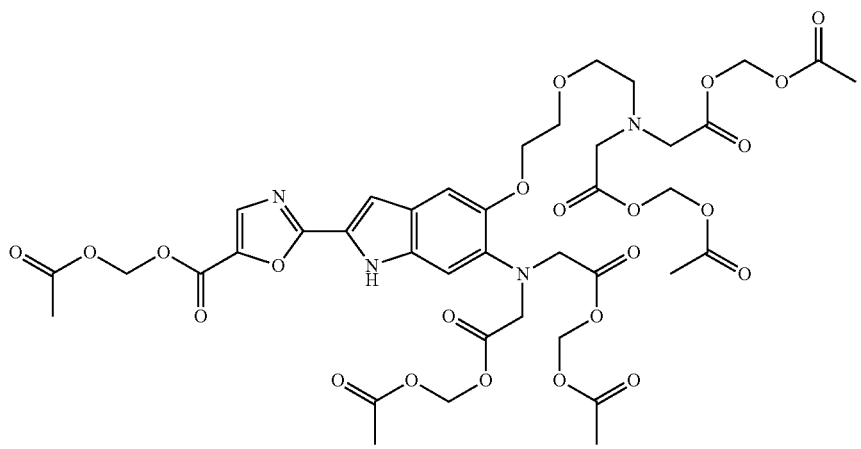 [SMILES: CC(=O)OCOC(=O)CN(CCOCCOc1cc2cc(-c3ncc(C(=O)OCOC(C)=O)o3)[nH]c2cc1N(CC(=O)OCOC(C)=O)CC(=O)OCOC(C)=O)CC(=O)OCOC(C)=O] |
| 205 | 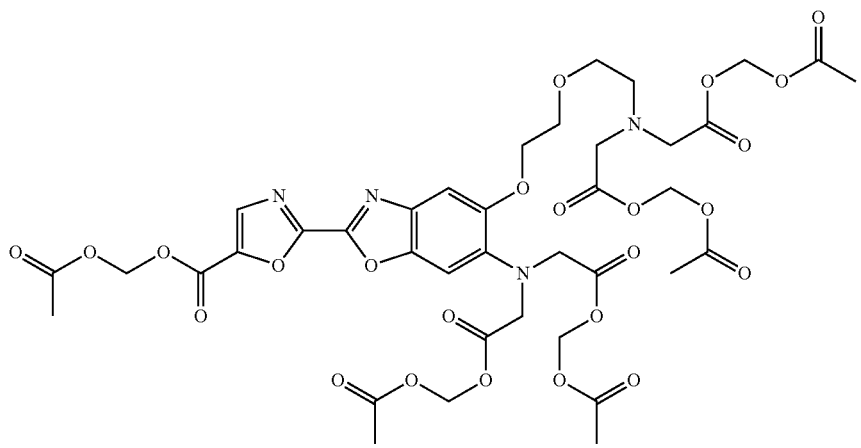 [SMILES: CC(=O)OCOC(=O)CN(CCOCCOc1cc2nc(-c3ncc(C(=O)OCOC(C)=O)o3)oc2cc1N(CC(=O)OCOC(C)=O)CC(=O)OCOC(C)=O)CC(=O)OCOC(C)=O] |
| 206 | 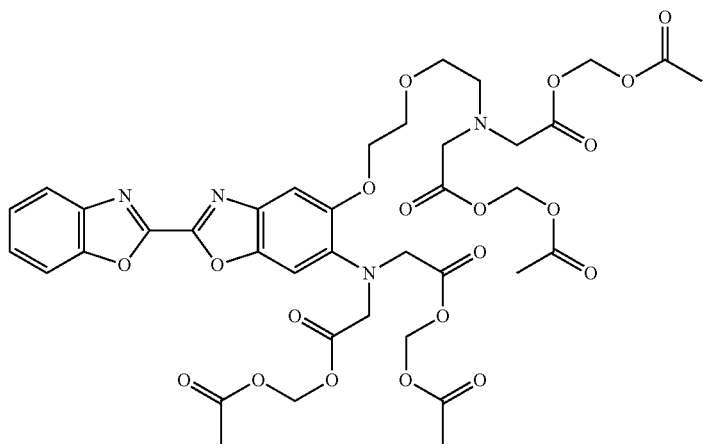 [SMILES: CC(=O)OCOC(=O)CN(CCOCCOc1cc2nc(-c3nc4ccccc4o3)oc2cc1N(CC(=O)OCOC(C)=O)CC(=O)OCOC(C)=O)CC(=O)OCOC(C)=O] |

TABLE 2-continued
Exemplary compounds of the present disclosure:
| Compound# | Structure |
|---|---|
| 207 | 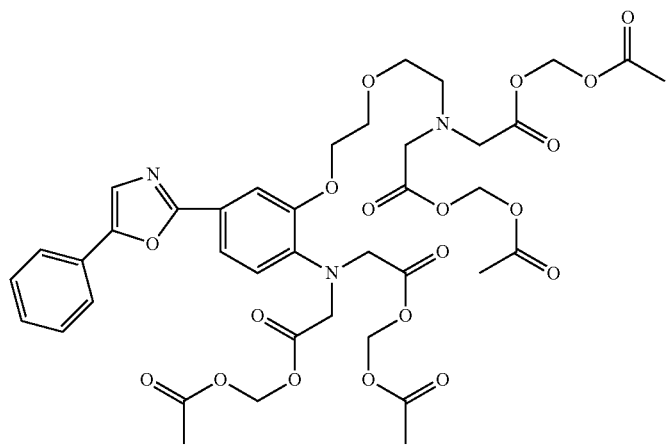 [SMILES: CC(=O)OCOC(=O)CN(CCOCCOc1cc(-c2ncc(-c3ccccc3)o2)ccc1N(CC(=O)OCOC(C)=O)CC(=O)OCOC(C)=O)CC(=O)OCOC(C)=O] |
| 208 | 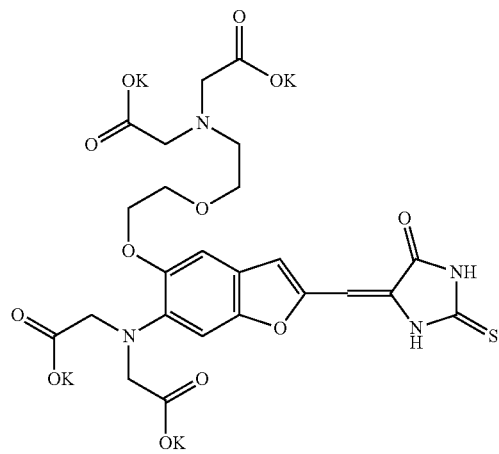 |
| 209 | 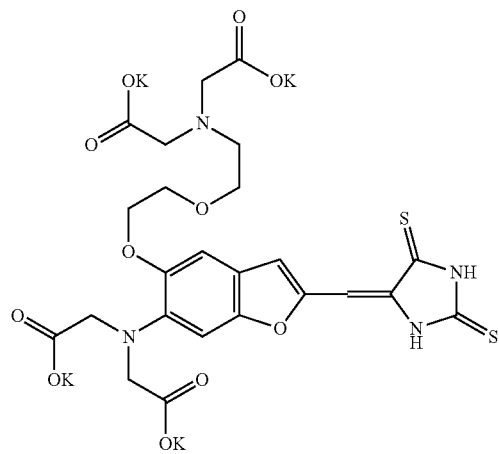 |

TABLE 2-continued
Exemplary compounds of the present disclosure:
| Compound# | Structure |
|---|---|
| 210 | 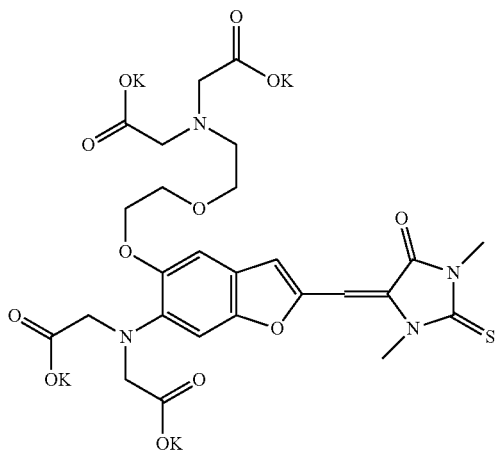 |
| 211 | 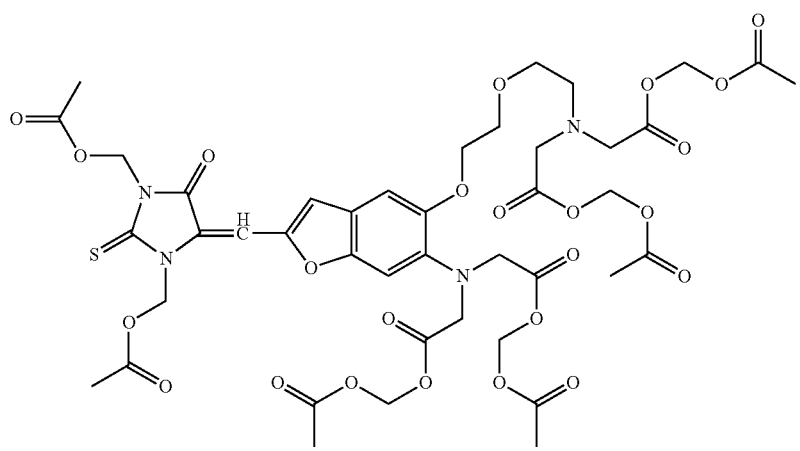 [SMILES: CC(=O)OCOC(=O)CN(CCOCCOc1cc2cc(C=C3C(=O)N(COC(C)=O)C(=S)N3COC(C)=O)oc2cc1N(CC(=O)OCOC(C)=O)CC(=O)OCOC(C)=O)CC(=O)OCOC(C)=O] |
| 212 | 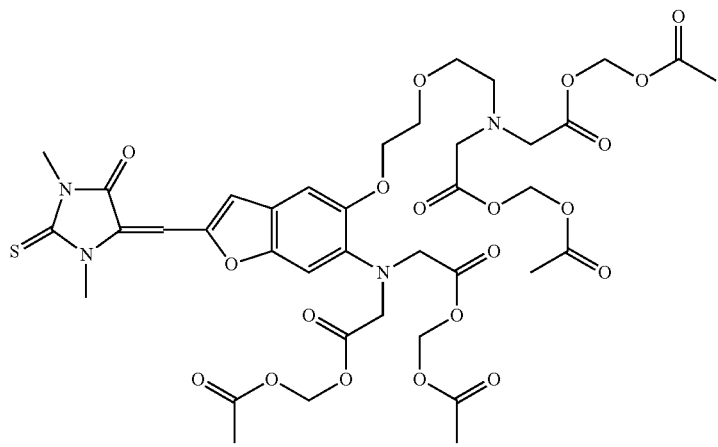 [SMILES: CC(=O)OCOC(=O)CN(CCOCCOc1cc2cc(C=C3C(=O)N(C)C(=S)N3C)oc2cc1N(CC(=O)OCOC(C)=O)CC(=O)OCOC(C)=O)CC(=O)OCOC(C)=O] |

TABLE 2-continued

Exemplary compounds of the present disclosure:

| Compound# | Structure |
|---|---|
| 213 | 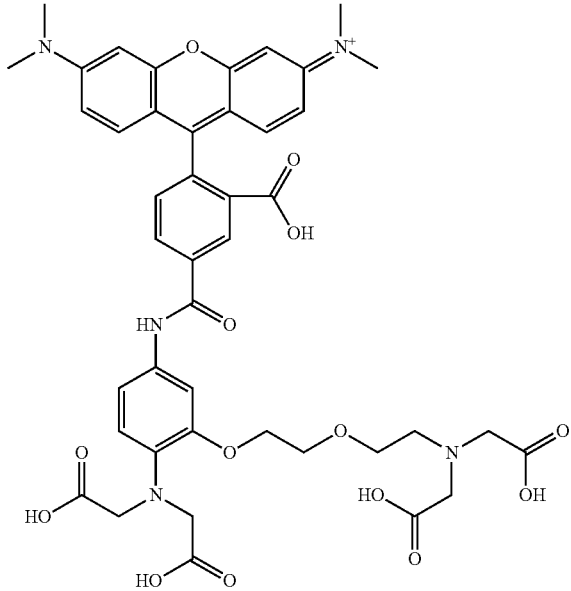 [SMILES: CN(C)c1ccc2c(-c3ccc(C(=O)Nc4ccc(N(CC(=O)O)CC(=O)O)c(OCCOCCN(CC(=O)O)CC(=O)O)c4)cc3C(=O)O)c3ccc(=[N+](C)C)cc-3oc2c1] |
| 214 | 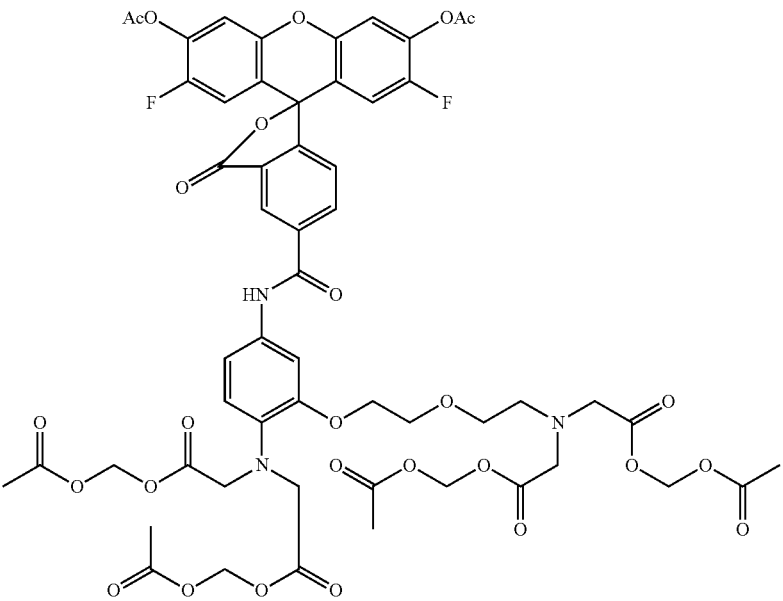 [SMILES: CC(=O)OCOC(=O)CN(CCOCCOc1cc(NC(=O)c2ccc3c(c2)C(=O)OC32c3cc(F)c(OC(C)=O)cc3Oc3cc(OC(C)=O)c(F)cc32)ccc1N(CC(=O)OCOC(C)=O)CC(=O)OCOC(C)=O)CC(=O)OCOC(C)=O] |

The subject compounds may contain one or more asymmetric centers and may thus give rise to enantiomers, diastereomers, and other stereoisomeric forms that may be defined, in terms of absolute stereochemistry, as (R)- or (S)-. The present disclosure is meant to include all such possible isomers, as well as, their racemic and optically pure forms. When the compounds described herein contain olefinic double bonds or other centers of geometric asymmetry, and unless specified otherwise, it is intended that the compounds include both E and Z geometric isomers. Likewise, all tautomeric forms are also intended to be included.

The fluorophore moiety can be any compound described by any of Formulas 1-9 that exhibits an absorption maximum beyond 300 nm, that is bound to a chelator by a covalent linkage L, or that is fused to a chelator. The covalent linkage L may be none, a covalent bond, or a suitable combination of multiple single bonds, double bonds and/or triple bonds as described in greater detail below. In some cases, the covalent linkage binding the fluorophore moiety to the chelator optionally incorporates 1-20 nonhydrogen atoms selected from the group consisting of C, N, O, P, B, Si and S.

As described herein, where the fluorophore moiety is a xanthene, the resulting compound may be a fluorescein, a rhodol, or a rhodamine. As used herein, fluorescein includes, but is not limited to, benzo- or dibenzofluoresceins, semi-naphthofluoresceins, and naphthofluoresceins. Similarly, as used herein, rhodol includes, but is not limited to, seminaphthorhodafluors (e.g., as described in U.S. Pat. No. 4,945,171). Any convenient fluorinated xanthene dyes, or portions thereof, can be adapted for use as a fluorophore moiety in the subject compounds, including but not limited to, those fluorinated xanthene dyes described as possessing particularly useful fluorescence properties (e.g., U.S. Pat. No. 6,162,931).

In one aspect of the present disclosure, the fluorophore moiety has an absorption maximum beyond 480 nm, e.g., greater than 480 nm. In a particularly useful embodiment, the fluorophore moiety absorbs at or near 488 nm to 514 nm, and so is particularly suitable for excitation by the output of an argon-ion laser excitation source, or near 546 nm, and so is particularly suitable for excitation by a mercury arc lamp.

Any convenient fluorophore moiety can be selected to confer desirable fluorescence properties on the resulting indicator compound it is incorporated into. In some cases, the resulting indicator compound exhibits a detectable optical response when excited by energy having a wavelength at which that fluorophore absorbs as used herein, where a detectable optical response means a change in, or occurrence of, an optical property that is detectable either by observation or instrumentally, such as a change in absorption (excitation) wavelength, fluorescence emission wavelength, fluorescence emission intensity, fluorescence polarization, or fluorescence lifetime, among others.

In general terms, the compounds of the present disclosure exhibit a detectable change in an optical response upon binding a target metal ion. Where the detectable response is a fluorescence response, the detectable change can be a change in fluorescence, such as a change in the intensity, excitation or emission wavelength distribution of fluorescence, fluorescence lifetime, fluorescence polarization, or a combination thereof. In some cases, the change in optical response upon binding the target metal ion is a change in fluorescence intensity that is greater than approximately 50-fold, such as a change that is greater than 100-fold.

Synthesis

The compounds of the present disclosure may be prepared using any suitable synthetic scheme. The methodology used to prepare the compounds of the present disclosure may involve two components. The first component may involve the formation of the chelator, while the second may involve the modification of the chelator by forming a reactive functional group, covalently attaching a conjugate, or covalently attaching a fluorophore moiety to form the desired indicator compound. Although these synthetic components are typically performed in the order given, they may be carried out in any other suitable sequence. For example, a portion of the chelator may be derivatized with a fluorescent dye prior to formation of the complete chelator ring. The appropriate methods may be used to synthesize the desired compounds of the present disclosure.

As the metal binding ability of the resulting chelators may be significantly influenced by the nature of the amine substituents, careful selection of the alkylating agent may be necessary to prepare a reporter for a particular target ion. PEGTA chelators are generally selective for calcium ion. Selection of an alkylating agent that incorporates a precursor to a reactive functional group is useful for producing chemically reactive compounds of the present disclosure, as well as acting as a useful intermediate for preparing conjugates, as described above.

The syntheses of chelating groups selective for different metal ions has been well described in Examples 1-31. Synthetic methods that can be readily adapted to prepare chelator intermediates useful for the synthesis of the subject compounds include, e.g., those method described by U.S. Pat. No. 4,603,209; U.S. Pat. No. 5,049,673; U.S. Pat. No. 4,849,362; U.S. Pat. No. 5,453,517; U.S. Pat. No. 5,501,980; U.S. Pat. No. 5,459,276; U.S. Pat. No. 5,501,980; U.S. Pat. No. 5,459,276; U.S. Pat. No. 5,516,911; and U.S. Application No. 2002/0164616.

Synthesis of conventional xanthene dyes such as fluoresceins, rhodamines and rhodols typically involves the condensation of two equivalents of resorcinol (for fluoresceins), aminophenol (for rhodamines) or a mixture of a resorcinol and an aminophenol (for rhodols) with a carbonyl-containing moiety such as a phthalic acid derivative or benzaldehyde derivatives. However, in the synthesis of the xanthene indicators of the present disclosure, the desired resorcinol or aminophenol is condensed with a chelator intermediate that contains a carboxylic acid, anhydride or acyl halide bound directly to the chelating moiety.

Alternatively the fluorescent xanthene indicators of the present disclosure can be prepared via the condensation of properly protected xanthones with a chelator anion, typically prepared from the corresponding chelator bromide or iodide. This organometallic chemistry is also well described in the literature (U.S. Pat. No. 5,049,673; U.S. Pat. No. 5,453,517; U.S. Pat. No. 5,501,980; U.S. Pat. No. 5,459,276; U.S. Pat. No. 5,501,980; U.S. Pat. No. 5,459,276; and U.S. Pat. No. 5,516,911; U.S. Pat. No. 8,779,165; U.S. Pat. No. 8,927,224; U.S. Pat. No. 9,097,730; U.S. Pat. No. 9,279,817. C. Chen, R. Yeh and D. S. Lawrence, J. Am. Chem. Soc. 2002, 124, 3840; U.S. Pat. No. 5,049,673); Y. Urano, M. Kamiya, K. Kanda, T. Ueno, K. Hirose and T. Nagano, J. Am. Chem. Soc. 2005, 127, 4888) and can be readily adapted to synthesize the compounds of the present disclosure (X. Zhou et al., Angew. Chem. Int. Ed., 2017, 56, 4197; M. Sednev et al., Bioconjugate Chem., 2013, 24, 690; K. Kolmakov et. al., Eur. J Chem. 2010, 3593; Y. Koide et. al., ACS Chem. Biol., 2011, 6, 600).

Other fluorescent indicators of the present disclosure can be readily prepared by adapting the published methods using the intermediates described in Examples 4, 5, 10 and 27. The syntheses of a variety of fluorophores are well described in the literature, e.g., bodipy dyes (N. Boens et. al., Chem. Soc. Rev., 2012, 41, 1130; C. Thivierge et. al., J. Org. Chem., 2011, 76, 5219; U.S. Pat. No. 6,340,750), quinolines (U.S. Pat. No. 4,603,209), coumarins (U.S. Pat. No. 4,146,712; U.S. Pat. No. 4,200,753; U.S. Pat. No. 4,921,827; U.S. Pat. No. 5,696,157; U.S. Pat. No. 6,566,508), cyanines (A. Mishra et. al., Chem Rev., 2000, 100, 1973), fura and indo analogs (U.S. Pat. No. 4,849,362; U.S. Pat. No. 5,453,517), any of which can be adapted for use in preparing the subject compounds.

Post-condensation modifications of both the chelator and the fluorophore moiety are typically analogous to known methods of indicator modification and can be adapted for use in preparation of the subject compounds. For example, the reduction of nitro substituents to amino groups, the conversion of carboxy substituents to cyano groups, and the preparation of esters of carboxylic acids, including acetoxymethyl esters. Additionally, a given salt or counterion of the indicators of the present disclosure may be readily converted to other salts by treatment with e.g., ion-exchange resins, selective precipitation, and basification.

Post-condensation modifications of xanthylium dyes are conventional to one of ordinary skill in the art and can be adapted for use in preparation of the subject compounds. For instance, the xanthenone portion of the dye can be halogenated by treatment with an appropriate halogenating agent, such as liquid bromine. Xanthenes containing unsaturated fused rings can also be hydrogenated to the saturated derivatives.

The reduced and oxidized versions of the xanthene indicators are freely interconvertible by well-known oxidation or reduction reagents, including borohydrides, aluminum hydrides, hydrogen/catalyst, and dithionites and can be adapted for use in preparation of the subject compounds. Care must be exercised to select an oxidation or reducing agent that is compatible with the chelator used. A variety of oxidizing agents mediate the oxidation of dihydroxanthenes, including molecular oxygen in the presence or absence of a catalyst, nitric oxide, peroxynitrite, dichromate, triphenylcarbenium and chloranil. The dihydroxanthenes may also be oxidized electrochemically, or by enzyme action, including the use of horseradish peroxidase in combination with peroxides or by nitric oxide.

Applications of the Fluorescent Indicators of the Present Disclosure

The indicators disclosed herein possess particular utility for the detection and/or quantification of metal ions in a sample of interest. Such indicators may be useful for measuring ions in a variety of samples, including but not limited to, extracellular spaces; in vesicles; in vascular tissue of plants and animals; biological fluids such as blood and urine; in fermentation media; in environmental samples such as water, soil, waste water and seawater; and in chemical reactors. Optical indicators for ions are important for qualitative and quantitative determination of ions, particularly in living cells. Fluorescent indicators for metal cations also permit the continuous or intermittent optical determination of these ions in living cells, and in solutions containing the ions.

In effecting such determination, the substance to be determined, or analyte, which contains the ion of interest can be contacted with a fluorescent indicator (e.g., as disclosed herein). Complexation of a metal ion of interest in the chelator of the indicator can result in a detectable change in the fluorescence properties of the indicator. Detection and optionally quantification of the detectable change permits the ion of interest to be detected and optionally quantified.

Upon binding the target ion in the chelating moiety of the indicator, the optical properties of the attached fluorophore are generally affected in a detectable way, and this change may be correlated with the presence of the ion according to a defined standard. Compounds having relatively long wavelength excitation and emission bands can be used with a variety of optical devices and require no specialized (quartz) optics, such as are required by indicators that are excited or that emit at shorter wavelengths. These indicators are suitable for use in fluorescence microscopy, flow cytometry, fluorescence microplate readers, or any other application of interest where fluorescent metal ion indicators find use.

In some cases, the determination method may be based on the so-called "PET effect", or the transfer, induced by photons, of electrons (photoinduced electron transfer=PET) from the ionophoric moiety or ionophore, respectively, to the fluorophore moiety or fluorophore, respectively, which leads to a decrease in the (relative) fluorescence intensity and the fluorescence decay time of the fluorophore. Absorption and emission wavelengths, however, are not significantly affected in the process (J. R. Lakowicz in "Topics in Fluorescence Spectroscopy", Volume 4; Probe Design and Chemical Sensing; Plenum Press, New York & London (1994)).

By the binding of ions to the ionophore, the PET effect may be partly or completely inhibited, so that there is an increase in the fluorescence of the fluorophore moiety. Hence, the concentration or the activity of the ion to be determined can be deduced by measuring the change in fluorescence properties. i.e. fluorescence intensity and/or fluorescence decay time.

A variety of fluorescent indicators that are useful for the detection of biologically relevant soluble free metal ions (such as $Ca^{2+}$, $Mg^{2+}$ and $Zn^{2+}$) have been described that utilize oxygen-containing anionic or polyanionic chelators to bind to metal ions. In general, a useful property for metal ion indicators is selectivity, or the ability to detect and/or quantify a selected metal ion in the presence of other metal ions. Discrimination of $Ca^{2+}$, $Na^+$ and/or $K^+$ ions in the presence of other metal ions is particularly advantageous in certain biological or environmental samples. For most biological applications, it is useful that the indicators be effective in aqueous solutions. It is also beneficial if the indicator absorbs and emits light in the visible spectrum where biological materials typically have low intrinsic absorbance or fluorescence.

Optical methods using fluorescence detection of metal ions permit measurement of the entire course of ion flux in a single cell as well as in groups of cells. The advantages of monitoring transport by fluorescence techniques include the high level of sensitivity of these methods, temporal resolution, modest demand for biological material, lack of radioactivity, and the ability to continuously monitor ion transport to obtain kinetic information (Eidelman, O. Cabantchik, Z. I. Biochim. Biophys. Acta, 1989, 988, 319-334). The general principle of monitoring transport by fluorescence is based on having compartment-dependent variations in fluorescence properties associated with translocation of compounds.

Any convenient optical methods for measuring $Ca^{2+}$ ion flux can be adapted for use in the subject methods (e.g., U.S. Pat. No. 5,049,673; Scarpa, A. Methods of Enzymology, 1979, 56, 301 Academic Press, Orlando, Fla.; Tsien, R. Y. Biochemistry, 1980, 19, 2396; Grynkiewicz, G., Poenic, M., Tsien, R. Y. J. Biol Chem., 260, 3440) including methods modified for high-throughput assays (e.g., U.S. Pat. No. 6,057,114).

The indicator compound of interest is generally prepared for use as a detection reagent by dissolving the indicator in solution at a concentration that is optimal for detection of the indicator at the expected concentration of the target ion. Modifications that are designed to enhance permeability of the indicator through the membranes of live cells, such as functionalization of carboxylic acid moieties using acetoxymethyl esters and acetates, may require the indicator to be predissolved in an organic solvent such as dimethylsulfoxide (DMSO) to facilitate addition to a cell suspension, where the indicators may then readily enter the cells. Intracellular enzymes then cleave the esters, generating more polar acids and phenols which are then well-retained inside the cells. For applications where permeability of cell-membranes is required, the indicators of the present disclosure can be substituted by only one fluorophore.

The specific indicator used in a particular assay or experiment may be selected based on the desired affinity for the target ion as determined by the expected concentration range in the sample, the desired spectral properties, and/or the desired selectivity. Initially, the suitability of a material as an indicator of ion concentration can be tested by mixing a constant amount of the indicating reagent with a measured amount of the target ion under the expected experimental conditions.

Where the binding of an ion in the metal ion-binding moiety of the indicator results in a detectable change in spectral properties of the indicator compound, that indicator may be used for the detection and/or quantification of that ion (the target ion). Although the change in spectral properties may include for example a change in absorption intensity or wavelength, preferably the change in spectral properties is a detectable fluorescence response. Indicators of interest can display a high selectivity, that is, they show a sufficient rejection of non-target ions. The interference of a non-target ion can be tested by a comparable titration of the indicator with that ion.

A detectable fluorescence response, as used herein, is a change in a fluorescence property of the indicator that is capable of being perceived, either by direct visual observation or instrumentally, the presence or magnitude of which is a function of the presence and/or concentration of a target metal ion in the test sample. This change in a fluorescence property is typically a change in fluorescence quantum yield, fluorescence polarization, fluorescence lifetime, a shift in excitation or emission wavelength, among others, or a combination of one or more of such changes in fluorescence properties. The detectable change in a given spectral property is generally an increase or a decrease. However, spectral changes that result in an enhancement of fluorescence intensity and/or a shift in the wavelength of fluorescence emission or excitation may also be useful. The change in fluorescence on ion binding may be due to conformational or electronic changes in the indicator that may occur in either the excited or ground state of the fluorophore, due to changes in electron density at the ion binding site, due to quenching of fluorescence by the bound target metal ion, or due to any combination of these or other effects.

In some cases, an indicator for a specific target ion is an indicator that exhibits at least a 50-fold change in net fluorescence emission intensity (either an increase or decrease), or at least a 1 nanosecond difference in fluorescence lifetime (either shorter or longer). In one aspect of the present disclosure, the indicator exhibits a 50-fold or greater change in net fluorescence emission intensity, and/or a 100% change in fluorescence lifetime in the presence of the target ion. In certain aspects of the present disclosure, the indicator exhibits a shift in excitation or emission wavelength of at least 10 nm (either to shorter or longer wavelength), more preferably exhibiting a wavelength shift of 25 nm or greater.

The spectral response of a selected indicator to a specific metal ion is a function of the characteristics of the indicator in the presence and absence of the target ion. For example, binding to a metal ion may alter the relative electron densities of the fluorophore and the metal binding site. Additionally, or in the alternative, some metal ions may quench fluorescence emission when in close proximity to a fluorophore (heavy atom quenching). In one embodiment of the present disclosure, the indicator is essentially nonfluorescent or exhibits low fluorescence in target ion-free solution and exhibits an increase in fluorescence intensity or fluorescence lifetime (or both) upon target metal ion binding.

As the optical response of the indicating reagent is typically determined by changes in fluorescence, the threshold of detection of the target ion will be dependent upon the sensitivity of the equipment used for its detection.

If the optical response of the indicator will be determined using fluorescence measurements, the sample of interest is typically stained with indicator concentrations of $10^{-9}$ M to $10^{-3}$ M. The most useful range of analyte concentration includes about one log unit above and below the dissociation constant of the ion-indicator complex. This dissociation constant may be determined by titration of the indicator with known concentrations of the target ion, usually over the range of virtually zero concentration to approximately 100 mM of the target ion, depending on which ion is to be measured and which indicator is being used. The dissociation constant may be affected by the presence of other ions, particularly ions that have similar ionic radii and charge. It may also be affected by other conditions such as ionic strength, pH, temperature, viscosity, presence of organic solvents and incorporation of the sensor in a membrane or polymeric matrix, or conjugation or binding of the sensor to a protein or other biological molecule. Any or all of these effects are readily determined, and can be taken into account when calibrating a selected indicator.

The subject indicator can be combined with a sample in a way that will facilitate detection of the target ion concentration in the sample. The sample is generally a fluid or liquid suspension that is known or suspected to contain the target ion. Representative samples of interest include, but are not limited to, intracellular fluids from cells such as in blood cells, cultured cells, muscle tissue, neurons and the like; extracellular fluids in areas immediately outside of cells; fluids in vesicles; fluids in vascular tissue of plants and animals; biological fluids such as blood, saliva, and urine; biological fermentation media; environmental samples such as water, soil, waste water and sea water; industrial samples such as pharmaceuticals, foodstuffs and beverages; and samples from chemical reactors. Detection and quantitation of the target ion in a sample can help characterize the identity of an unknown sample, or facilitate quality control of a sample of known origin.

In one embodiment of the present disclosure, the sample includes cells, and the indicator is combined with the sample in such a way that the indicator is added within the sample cells. By selection of the appropriate chelating moiety, fluorophore, and the substituents thereon, indicators may be prepared that will selectively localize in a desired organelle, and provide measurements of the target ion in those organelles. Conjugates of the indicators of the present disclosure with organelle-targeting peptides are also provided and may be used to localize the indicator to the selected organelle, facilitating measurement of target ion presence or concentration within the organelle (as described in U.S. Pat. No. 5,773,227, hereby incorporated by reference). Alternatively, selection of a lipophilic fluorophore, (e.g., a fluorophore having predominantly lipophilic substituents), may result in localization of the indicator in lipophilic environments in the cell, such as cell membranes. Selection of cationic indicators will in some cases result in localization of the indicator in mitochondria.

In one embodiment of the present disclosure, the subject indicator compound optionally further includes a metal ion. In some embodiments, the subject compounds, e.g., as described in any of the embodiments described herein, are associated, either covalently or noncovalently, with a surface such as a microfluidic chip, a silicon chip, a microscope slide, a microplate well, or another solid or semisolid matrix, and is combined with the sample of interest as it flows over the surface. In this embodiment, the detectable optical response may therefore be detected on the matrix surface itself, typically by use of instrumental detection. This embodiment of the present disclosure may be particularly suited to high-throughput screening using automated methods.

The fluorescence response of the indicator to the target ion may be detected by various means that include without limitation measuring fluorescence changes with fluorometers, fluorescence microscopes, laser scanners, flow cytometers, and microfluidic devices, as well as by cameras and other imaging equipment. These measurements may be made remotely by incorporation of the fluorescent ion sensor as part of a fiber optic probe. The indicator may be covalently attached to the fiber optic probe material, typically glass or functionalized glass (e.g., aminopropyl glass) or the indicator may be attached to the fiber optic probe via an intermediate polymer, such as polyacrylamide. The indicator solution is alternatively incorporated non-covalently within a fiber optic probe, as long as there is a means whereby the target ion may come into contact with the indicator solution. More preferably, the indicators of the present disclosure are used with a fluorescence microplate reader that is equipped with an automated liquid handling system such as FLIPR, FLEXSTATION and FDSS.

In another aspect of the present disclosure, the subject fluorescent ion indicators may be used in combination with one or more non-fluorescent dyes that are not substantially cell-permeable in order to reduce the background fluorescence, e.g., analogous to the methods described in U.S. Pat. No. 6,420,183. Non-fluorescent dyes and dye mixtures that have large water solubilities and minimal effects on the physiology of the cells are preferred for this application. In some cases, the dyes are water-soluble azo dyes (such as trypan blue and those dyes which have been used in cell-based assays as described by H. W. Davis, R. W. Sauter. Histochemistry, 1977, 54, 177; W. E. Hathaway, L. A. Newby, J. H. Githens, Blood, 1964, 23, 517; C. W. Adams, O. B. Bayliss, R. S. Morgan. Atherosclerosis, 1977, 27, 353.

Aspects of the present disclosure include methods of screening using the subject compounds. The screening methods described herein can be performed with cells growing in or deposited on solid surfaces. One technique that finds use in the subject screening methods is to use a microwell plate where the fluorescence measurements are performing using a commercially available fluorescent plate reader. These methods lend themselves to use in high throughput screening using both automated and semi-automated systems.

Using the indicators of the present disclosure, the measurement of fluorescence intensity can provide a sensitive method for monitoring changes in intracellular ion concentrations. Thus, fluorescence measurements at appropriate excitation and emission wavelengths provide a fluorescence readout which is sensitive to the changes in the ion concentrations.

In some embodiments, the subject method includes a) adding a subject compound (e.g., as described herein) (e.g., a fluorogenic compound or precursor) to a sample containing a cell; b) incubating the sample for a time sufficient for the compound to be loaded into the cell and for an indicator compound (e.g., a fluorescent compound) to be generated intracellularly (e.g., in situ); c) illuminating the sample at a wavelength that generates a fluorescence response from the indicator compound; d) detecting a fluorescence response from the indicator compound (e.g., an indicator that is complexed with intracellular calcium ions); and e) correlating the fluorescence response with the presence of intracellular calcium.

In one aspect of the present disclosure, the subject method is useful for screening potential therapeutic drugs, for example drugs which may affect ion concentrations in biological cells. These methods may include measuring ion concentrations as described above in the presence and absence (as a control measurement) of the test sample. Control measurements are usually performed with a sample containing all components of the test sample except for the putative drug being screened. Detection of a change in ion concentration in the presence of the test agent relative to the control indicates that the test agent is active. Ion concentrations can also be determined in the presence or absence of a pharmacologic agent of known activity (i.e., a standard agent) or putative activity (i.e., a test agent). A difference in ion concentration as detected by the methods disclosed herein allows one to compare the activity of the test agent to that of a standard agent of known activity. It will be recognized that many combinations and permutations of drug screening protocols are known to one of skill in the art and they may be readily adapted to use with the method of ion concentration measurement disclosed herein to identify compounds of interest which affect ion concentrations.

In one aspect of the present disclosure, the disclosed cell-permeable PEGTA calcium indicators (AM esters) have the greatly improved water solubility, which significantly improves their cell loading rate. The improved water solubility (as shown in Table 1) may reduce the optimal concentration of a detergent (e.g., Pluronic F127) often used in loading calcium indicators into live cells. The decrease or elimination of a detergent for loading calcium indicators into cells enable many new applications of calcium assays in the cell lines or live organisms that are severely affected by the cytotoxicity of detergents (C. Nagant, P. B. Savage and J. P. Dehaye, J. Applied Microbiology 2012, 112, 1173).

TABLE 1

Water solubility comparison of PEGTA compounds and conventional BAPTA calcium indicator AM esters

| Fluorophore Class | Water solubility at 25° C. (BAPTA Compound) | Water solubility at 25° C. (PEGTA Compound) |
|---|---|---|
| Bodipy | 0.27 µg/ml PBS (BAPTA Bodipy AM) | 1.29 µg/ml PBS (Compound 188) |
| Fluo | 1.26 µg/ml PBS (Fluo-4 AM) | 2.18 µg/ml PBS (Compound 24) |
| Fluorescein | 0.92 µg/ml PBS (BAPTA Fluorescein AM) | 1.63 µg/ml PBS (Compound 22) |

In some embodiments, the fluorescent ion indicators are used in a method to measure calcium flux. Cells (e.g., CHO cells) stably transfected with muscarinic receptor 1 are plated—e.g., at 60,000 cells per 100 µl per well in F12 with 5% FBS and 1% glutamine in a 96-well black wall/clear bottom Costar plate—and incubated (e.g., in 5% $CO_2$ at 37° C. overnight). The growth medium is removed and the cells are incubated with a fluorescent ion indicator (e.g., with 100 µl/well of 1-8 µM Fluo-3 AM, Fluo-4 AM or one or more compounds selected from Compound 22, 23, 24, 28, 33, 34, 40, 41 or 188 in Hanks and HEPES buffer for 1 hour at 37° C., 5% $CO_2$) with or without probenecid. Carbachol or ATP is added (e.g., 50 µl/well by NOVOstar, FlexStation or FLIPR) to achieve a final concentration. Fluorescent ion indicators of the present disclosure (e.g., as described herein, such as Compound 22, 23, 24, 28, 33, 34, 40, 41 or 188) load into cells much better than the corresponding BAPTA compounds at different ATP concentrations (e.g., 0.1 µM, 0.2 µM, 0.3 µM, 0.4 µM, 0.5 µM, 0.6 µM, 0.7 µM, 0.8 µM, 0.9 µM, or 1.0 µM). When probenecid is not used, the fluorescence intensity of a fluorescent ion indicator of the present disclosure (e.g., Compound 24), is much greater than that of the corresponding BAPTA compounds (e.g., Fluo-4 AM). The PEGTA calcium indicators of the present disclosure are unexpectedly well retained inside cells compared to the existing BAPTA-based calcium indicators (such as Fluo-3 and Fluo-4) that quickly leak out of cell, a factor resulting IN higher assay background. When probenecid is not used, Fluo-4 AM is not capable of detecting calcium in some types of cells and tissues for which Compound 24 is used.

In some embodiments, the subject method facilitates the screening of test samples in order to identify one or more compounds that are capable of modulating the activity of an ion channel, pump or exchanger in a membrane, and the method further includes stimulating the cell, monitoring changes in the intensity of the fluorescence response from the indicator compound, and correlating the changes in fluorescence intensity with changes in intracellular calcium levels.

Any convenient additional methods may be used to evaluate the efficacy of a stimulus that generates a target ion response. In some instances, the method includes (a) loading a first set and a second set of cells with the ion indicators of the present disclosure which monitor ion concentrations; (b) optionally, exposing both the first and second set of cells to a stimulus which modulates the ion channel, pump or exchanger; (c) exposing the first set of cells to the test sample; (d) measuring the ion concentrations in the first and second sets of cells; and (e) relating the difference in ion concentrations between the first and second sets of cells to the ability of a compound in the test sample to modulate the activity of an ion channel, pump or exchanger in cells. In some cases, the method may include the addition of probenecid or a probenecid derivative to the sample.

One or more of the methods disclosed herein may be enhanced by the addition of a cell-impermeant and non-fluorescent dye to the sample, such that the dye remains in the extracellular solution, and acts as an acceptor dye for energy transfer from the indicator compound, thereby decreasing background signal from the sample solution. In one aspect of the method, the cell-impermeant and non-fluorescent dye is a water-soluble azo dye.

Ion channels of particular interest which may be of interest in various applications of the subject methods, may include, but are not limited to, sodium, calcium, potassium, nonspecific cation, and chloride ion channels, each of which may be constitutively open, voltage-gated, ligand-gated, or controlled by intracellular signaling pathways.

Biological cells of potential interest, e.g., for screening or assay applications, include, but are not limited to, primary cultures of mammalian cells, cells dissociated from mammalian tissue, either immediately or after primary culture. Cell types of interest in various applications of the subject methods include, but are not limited to, white blood cells (e.g. leukocytes), hepatocytes, pancreatic beta-cells, neurons, smooth muscle cells, intestinal epithelial cells, cardiac myocytes, glial cells, and the like. The subject methods may also include the use of recombinant cells into which ion transporters, ion channels, pumps and exchangers have been inserted and expressed by genetic engineering. Many cDNA sequences for such transporters have been cloned (see U.S. Pat. No. 5,380,836 for a cloned sodium channel) and methods for their expression in cell lines of interest are within the knowledge of one of skill in the art and may be adapted for use in the subject methods (see, U.S. Pat. No. 5,436,128). Representative cultured cell lines derived from humans and other mammals which find use in various applications of the subject methods include, but are not limited to, LM cells, HEK-293 (human embryonic kidney cells), 3T3 fibroblasts, COS cells, CHO cells, RAT1 and HepG2 cells, Hela cells, $U_2OS$ cells and Jurkat cells etc.

Assay Kits & Systems

Also provided are kits and systems that find use in practicing embodiments of the methods, such as those described herein. The term "system" as employed herein refers to a collection of two or more different compounds or dyes, present in a single or disparate composition, that are brought together for the purpose of practicing the subject methods. The term kit refers to a packaged compound or dye. In some embodiments, the subject system or kit includes a subject compound (e.g., as described herein) and an additional component (e.g., as described herein).

Due to the advantageous properties and the simplicity of use of the disclosed ion indicator compounds, they can possess particular utility in the formulation of a kit for the complexation, detection, or quantification of selected target ions. An exemplary kit may include one or more compounds or compositions of the present disclosure (e.g., as described in any of the embodiments described herein), e.g., present as a pure compound, in a suitable carrier composition, or dissolved in an appropriate stock solution. The kit may further include instructions for the use of the indicator compound to complex or detect a desired target ion. The kit may further include one or more additional components, such as an additional detection reagent.

The indicator of the present disclosure may be present in the kit associated with a surface, such as a chip, microplate well, or other solid or semi-solid matrix.

The additional kit components may be selected from, without limitation, calibration standards of a target ion, ionophores, dyes, quenchers, fluorescence standards, aqueous buffers, surfactants and organic solvents. In some cases, the dye is a quencher that is a non-fluorescent and cell-impermeant quencher dye (e.g., as described herein). The additional kit components may be present as pure compositions, or as aqueous solutions that incorporate one or more additional kit components. Any or all of the kit components optionally further comprise buffers.

In some embodiments, the kit includes at least one indicator compound as described herein, and a non-fluorescent and cell-impermeant quencher dye. The non-fluorescent and cell-impermeant quencher dye is optionally present in a combined buffer solution with the compound, or the buffer solution of the cell-impermeant quencher dye is present in a separate container from the indicator compound.

In addition to the above-mentioned components, a subject kit may further include instructions for using the components of the kit, e.g., to practice the subject method. The instructions are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. CD-ROM, diskette, Hard Disk Drive (HDD), portable flash drive, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

The examples provided below illustrate selected aspects of the invention. They are not intended to limit or define the entire scope of the invention.

EXAMPLES

Example 1. Preparation of Compound 3

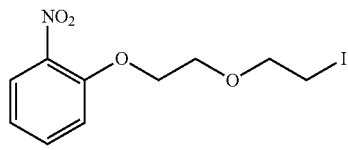 [SMILES: O=[N+]([O-])c1ccccc1OCCOCCI]

To the mixture of sodium 2-nitrophenolate (0.5 g, 3.1 mmol) in DMF (2 mL), 1-iodo-2-(2-iodoethoxy)ethane (3 g, 9.3 mmol) is added at room temperature. The mixture is heated at 80° C. for 1 hour. EtOAc (100 mL) is added at room temperature and the white precipitate is removed by filtration. The organic layer is washed with water, brine, dried (anhydrous $Na_2SO_4$) and concentrated under vacuum. The crude product is purified by silica gel column chromatography to give Compound 3 (0.9 g).

Example 2. Preparation of Compound 4

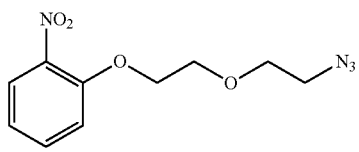 [SMILES: [N-]=[N+]=NCCOCCOc1ccccc1[N+](=O)[O-]]

The mixture of Compound 3 (0.85 g, 2.5 mmol) and sodium azide (0.33 g, 5 mmol) in DMF (6 mL) is heated at 80° C. for 1 hour. To the reaction mixture EtOAc (100 mL) is added at room temperature. The organic layer is washed with water, brine, dried over anhydrous $Na_2SO_4$ and concentrated under vacuum to give Compound 4 (0.6 g).

Example 3. Preparation of Compound 5

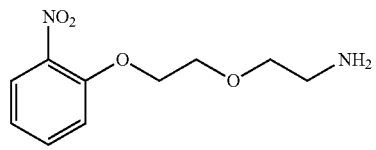 [SMILES: NCCOCCOc1ccccc1[N+](=O)[O-]]

To a steel pressure reactor, the solution of Compound 4 (0.64 g, 2.5 mmol) in EtOAc (20 mL) and MeOH (4 mL) is added, followed by Pd/C (10%, 0.1 g). The reaction vessel is filled with 60 psi hydrogen, and stirred at room temperature for two hours. The Pd/C is removed by Celite filtration. The organic layer is concentrated under vacuum to give Compound 5 (0.5 g).

Example 4. Preparation of Compound 6

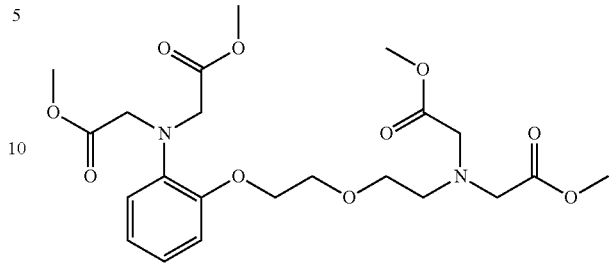

To the solution of Compound 5 (4 g, 20.4 mmol) and bromomethylaceate (31 g, 204 mmol) in MeCN (200 mL), diisopropylethylamine (35 mL) and sodium iodide (3.06 g, 20.4 mmol) are added at room temperature. The reaction mixture is refluxed for 36 hours, cooled to room temperature, and diluted with EtOAc (200 mL). The organic layer is washed with water, brine, dried (anhydrous $Na_2SO_4$) and concentrated under vacuum to give crude Compound 7, which is further purified by silica gel column to yield the pure product (9 g).

Example 5. Preparation of Compound 8

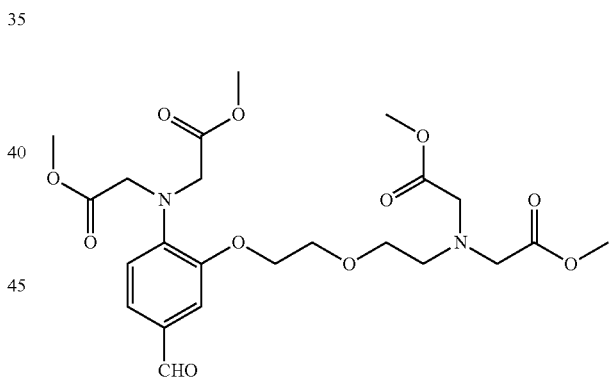

To a 100 mL flask with dry DMF (25 mL), $POCl_3$ (13.6 mL, 149 mmol) is added slowly at 0° C. The reaction mixture is stirred at 0° C. for 30 minutes at room temperature for 1 hour. To the solution of Compound 7 (9 g) in dry DMF (50 mL) in a 250 mL flask, the freshly made $POCl_3$/DMF solution is added dropwise at 0° C., via a cannulate. The mixture is stirred at room temperature for 30 minutes, and then 60 OC for 1 hour. The mixture is poured into ice-water (1000 mL) with NaOAc (100 g) and stirred overnight. The worked-up reaction mixture is extracted with EtOAc (200 mL), and the organic layer is washed with water, brine, dried (anhydrous $Na_2SO_4$) and concentrated under vacuum to give Compound 8 (9.1 g).

Example 6. Preparation of Compound 10

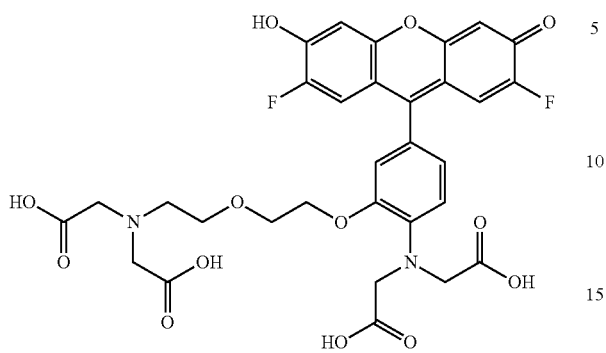

To the solution of compound 8 (0.15 g, 1.2 mmol) in methanesulfonic acid (5 mL), 4-fluororesorcinol (0.31 g, 2.4 mmol) is added at room temperature. The reaction mixture is heated at 65° C. for 30 minutes and then increased to 100° C. for 4 hours with $O_2$ bubbling. Ice water (50 mL) is added to stop the reaction, followed by 5M NaOH solution to make the reaction mixture pH>12. The mixture is stirring at room temperature for 1 hour. The crude Compound 10 is purified by HPLC, and give the pure Compound 10 (0.14 g) after lyophilization.

Example 7. Preparation of Compound 13

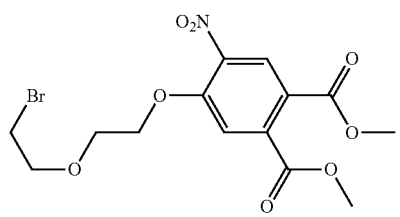

To the solution of dimethyl 4-hydroxy-5-nitrophthalate (1.5 g, 6 mmol) and 1-bromo-2-(2-bromoethoxy)ethane (4.1 g, 18 mmol) in DMF (6 mL), potassium carbonate (1.65 g, 12 mmol) is added at room temperature. The reaction mixture is heated at 80° C. for 2 hours. To the reaction mixture EtOAc (100 mL) is added at room temperature. The organic layer is washed with water, brine, dried (anhydrous $Na_2SO_4$) and concentrated under vacuum to give crude Compound 13, which is further purified by silica gel column to yield the pure Compound 13 (2.1 g).

Example 8. Preparation of Compound 14

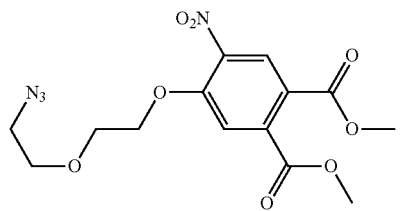 [SMILES: COC(=O)c1cc(OCCOCCBr)c([N+](=O)[O-])cc1C(=O)OC]

The mixture of compound 13 (2.1 g, 5.2 mmol) and sodium azide (0.67 g, 10.4 mmol) is heated at 80° C. in DMF (8 mL) for 1 hour. To the reaction mixture EtOAc (100 mL) is added at room temperature. The organic layer is washed with water, brine, dried (anhydrous $Na_2SO_4$) and concentrated under vacuum to give Compound 14 (1.9 g).

Example 9. Preparation of Compound 15

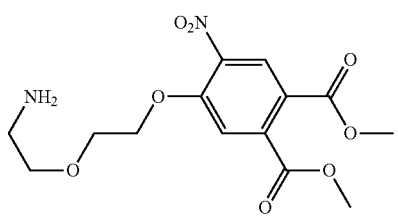

To a steel pressure reactor, the solution of compound 14 (1.3 g, 3.5 mmol) in EtOAc (40 mL) and MeOH (10 mL) is added, followed by Pd/C (10%, 0.15 g). The reactor is filled with hydrogen (60 psi), is stirred for two hours. The Pd/C is removed by Celite filtration. The organic layer is concentrated under vacuum to give 15 (1.1 g).

Example 10. Preparation of Compound 17

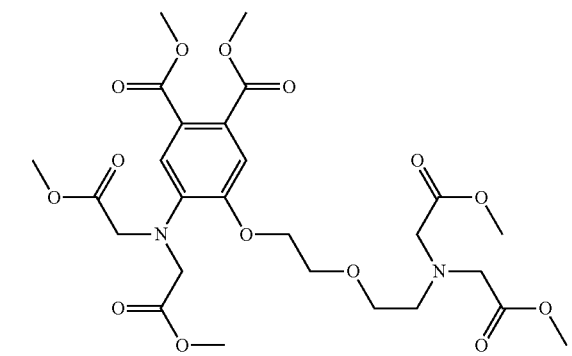

To the solution of compound 15 (1.1 g, 3.5 mmol) and bromomethylacetate (5.4 g, 35 mmol) in MeCN (50 mL), diisopropylethylamine (6 mL, 35 mmol) and sodium iodide (0.53 g, 3.5 mmol) are added. The mixture is refluxed for 4 days. To reaction mixture EtOAc (200 mL) is added at room temperature. The organic layer is washed with water, brine, dried (anhydrous $Na_2SO_4$) and concentrated under vacuum to give crude Compound 17, which is further purified by silica gel column to yield the pure Compound 17 (1.5 g).

Example 11. Preparation of Compounds 19 and 20

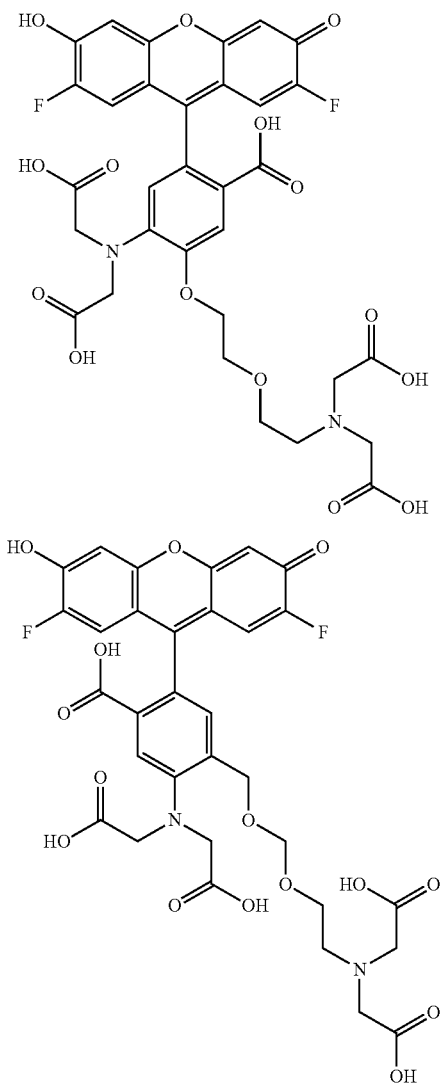

To the solution of compound 17 (1.5 g, 2.5 mmol) in methanesulfonic acid (15 mL), 4-fluororesorcinol (0.97 g, 7.5 mmol) is added at room temperature. The mixture is heated at 100° C. for 10 hours. Ice water (100 mL) is added to stop the reaction, followed by the addition of 5M NaOH solution to make the reaction mixture pH>12. The mixture is stirring at room temperature for 1 hour. The reaction mixture is purified by HPLC to give compound 19 (450 mg) and compound 20 (550 mg).

Example 12. Preparation of Compound 21

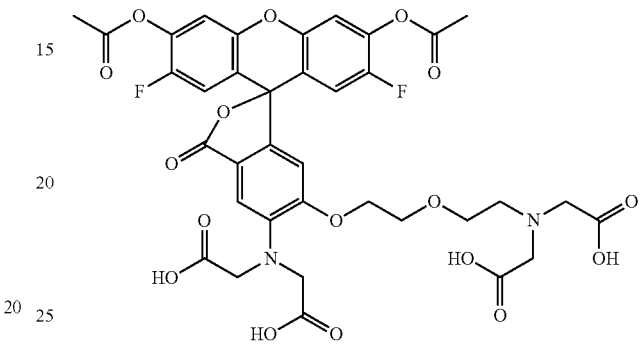

Compound 20 (350 mg) is heated at 80° C. with $Ac_2O$ (5 mL) and pyridine (0.1 mL) until Compound 20 is completely consumed. The solution is cooled to room temperature. The reaction mixture is poured into ice water, and carefully adjusted to pH=4-5. The aqueous mixture is titrated with dioxane to give a precipitate that is collected by filtration. The resulting mixture is first air-dried, and further vacuum-dried in a desiccator with $P_2O_5$ for 12 hours to yield crude Compound 21 that is directly used for next step reaction.

Example 13. Preparation of Compound 22

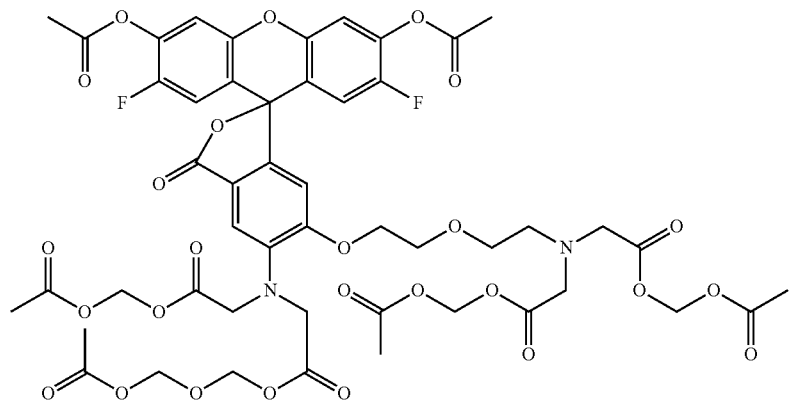 [SMILES: CC(=O)OCOCOC(=O)CN(CC(=O)OCOC(C)=O)c1cc2c(cc1OCCOCCN(CC(=O)OCOC(C)=O)CC(=O)OCOC(C)=O)C1(OC2=O)c2cc(F)c(OC(C)=O)cc2Oc2cc(OC(C)=O)c(F)cc21]

The crude Compound 21 (100 mg) is dissolved in anhydrous DMF (3 mL) at room temperature. To the solution BrCH₂OAc (0.18 mL) is slowly added while stirring in a water bath. To the resulted mixture iPr₂NEt (0.38 mL) is added slowly. The reaction mixture is stirred for 24-36 hours, and concentrated in vacuo. The residue is suspended in ethyl acetate (20 mL) and stirred for 1-2 hours. The mixture is filtered to remove the solid that is washed with ethyl acetate, and the filtrate is evaporated to dryness. The filtrate residue is purified on a silica gel column using 3:1:1 hexanes/EtOAc/chloroform as an eluent to give the desired Compound 22.

Example 14. Preparation of Compound 23

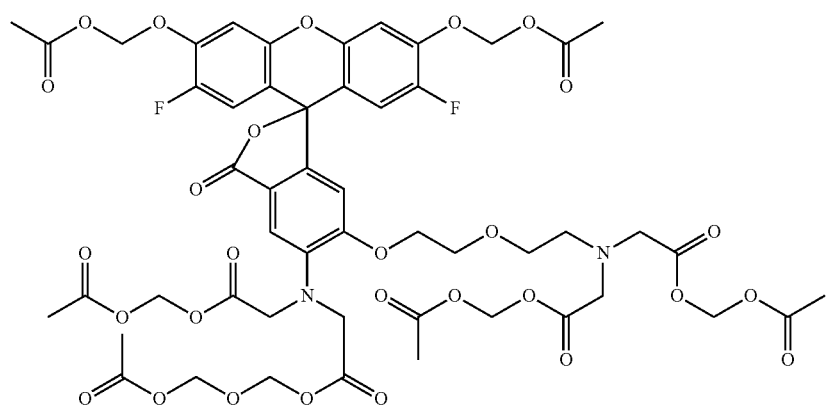 [SMILES: CC(=O)OCOCOC(=O)CN(CC(=O)OCOC(C)=O)c1cc2c(cc1OCCOCCN(CC(=O)OCOC(C)=O)CC(=O)OCOC(C)=O)C1(OC2=O)c2cc(F)c(OCOC(C)=O)cc2Oc2cc(OCOC(C)=O)c(F)cc21]

Compound 20 (100 mg) is dissolved in anhydrous DMF (3 mL) at RT. To the solution BrCH₂OAc (0.5 mL) is slowly added while stirring in a water bath. To the resulted mixture iPr₂NEt (0.38 mL) is added slowly. The reaction mixture is stirred for 24-36 hours, and concentrated in vacuo. The oily residue is purified on a silica gel column using 3:1:1 EtOAc/Hexanes/chloroform as an eluent to give the desired Compound 23.

Example 15. Preparation of Compound 24

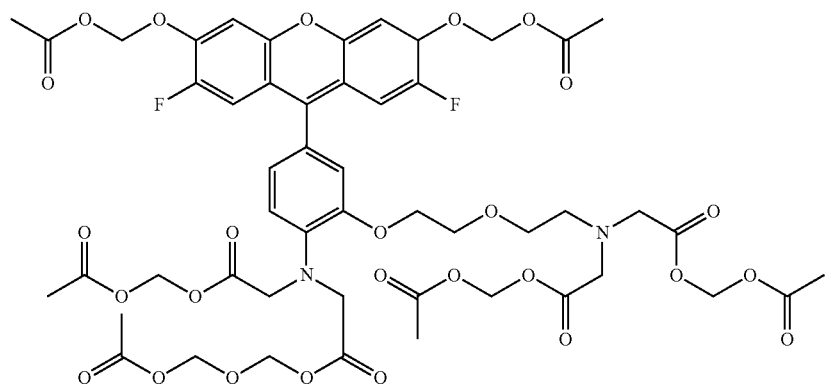 [SMILES: CC(=O)OCOCOC(=O)CN(CC(=O)OCOC(C)=O)c1ccc(C2=C3C=C(F)C(OCOC(C)=O)C=C3Oc3cc(OCOC(C)=O)c(F)cc32)cc1OCCOCCN(CC(=O)OCOC(C)=O)CC(=O)OCOC(C)=O]

Compound 10 (100 mg) is dissolved in anhydrous DMF (3 mL) at RT. To the solution BrCH₂OAc (0.5 mL) is slowly added while stirring in a water bath. To the resulted mixture iPr₂NEt (0.38 mL) is added slowly. The reaction mixture is stirred for 24-36 hours, and concentrated in vacuo. The oily residue is purified on a silica gel column using 3:1:1 EtOAc/Hexanes/chloroform as an eluent to give the desired Compound 24.

Example 16. Preparation of Compound 25

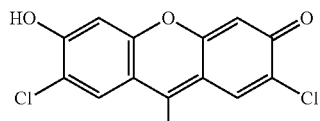

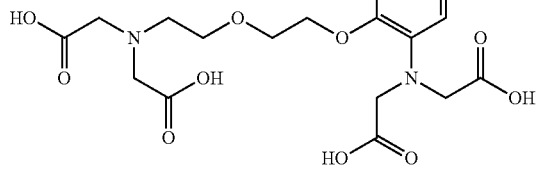

To the solution of compound 8 (0.15 g, 1.2 mmol) in methanesulfonic acid (5 mL), 4-chlororesorcinol (0.35 g, 2.4 mmol) is added at room temperature. The reaction mixture is heated at 65° C. for 30 minutes and then increased to 100° C. for 4 hours with $O_2$ bubbling. Ice water (50 mL) is added to stop the reaction, followed by 5M NaOH solution to make the reaction mixture pH>12. The mixture is stirring at room temperature for 1 hour. The crude Compound 25 is purified by HPLC, and give the pure Compound 25 (0.15 g) after lyophilization.

Example 17. Preparation of Compound 26

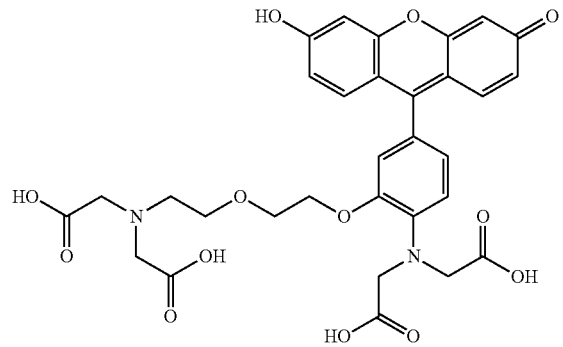

To the solution of compound 8 (0.15 g, 1.2 mmol) in methanesulfonic acid (5 mL), resorcinol (0.4 g, 3.6 mmol) is added at room temperature. The reaction mixture is heated at 65° C. for 30 minutes and then increased to 100° C. for 4 hours with $O_2$ bubbling. Ice water (50 mL) is added to stop the reaction, followed by 5M NaOH solution to make the reaction mixture pH>12. The mixture is stirring at room temperature for 1 hour. The crude Compound 26 is purified by HPLC, and give the pure Compound 26 (0.1 g) after lyophilization.

Example 18. Preparation of Compound 27

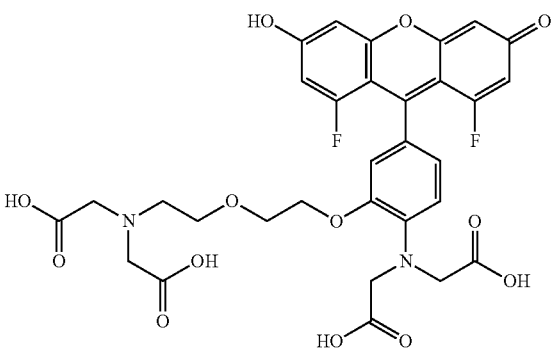 [SMILES: O=C(O)CN(CCOCCOc1cc(-c2c3c(F)cc(=O)cc-3oc3cc(O)cc(F)c23)ccc1N(CC(=O)O)CC(=O)O)CC(=O)O]

To the solution of compound 8 (0.15 g, 1.2 mmol) in methanesulfonic acid (5 mL), 3-fluororesorcinol (0.8 g, 7.2 mmol) is added at room temperature. The reaction mixture is heated at 65° C. for 90 minutes and then increased to 100° C. for 4 hours with $O_2$ bubbling. Ice water (50 mL) is added to stop the reaction, followed by 5M NaOH solution to make the reaction mixture pH>12. The mixture is stirring at room temperature for 1 hour. The crude Compound 27 is purified by HPLC, and give the pure Compound 27 after lyophilization.

Example 19. Preparation of Compound 28

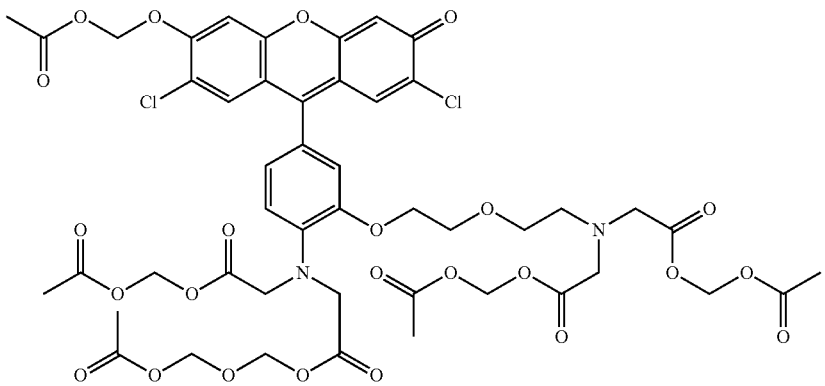 [SMILES: CC(=O)OCOCOC(=O)CN(CC(=O)OCOC(C)=O)c1ccc(-c2c3cc(Cl)c(=O)cc-3oc3cc(OCOC(C)=O)c(Cl)cc23)cc1OCCOCCN(CC(=O)OCOC(C)=O)CC(=O)OCOC(C)=O]

Compound 28 is prepared from Compound 25 analogously to the procedure of Compound 24.

Example 20. Preparation of Compound 29

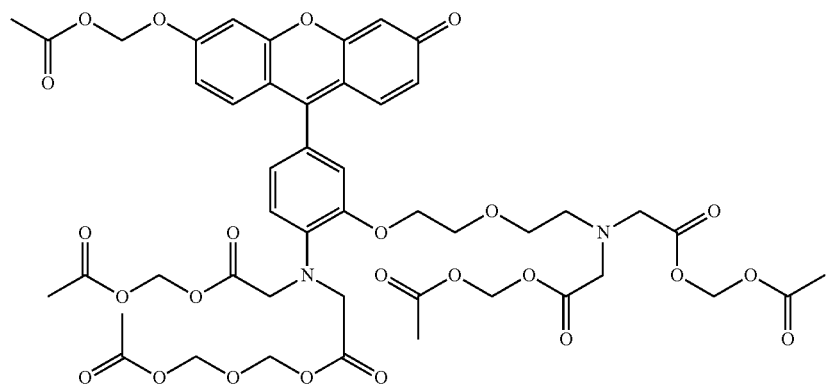 [SMILES: CC(=O)OCOCOC(=O)CN(CC(=O)OCOC(C)=O)c1ccc(-c2c3ccc(=O)cc-3oc3cc(OCOC(C)=O)ccc23)cc1OCCOCCN(CC(=O)OCOC(C)=O)CC(=O)OCOC(C)=O]

Compound 29 is prepared from Compound 26 analogously to the procedure of Compound 24.

Example 21. Preparation of Compounds 30 and 31

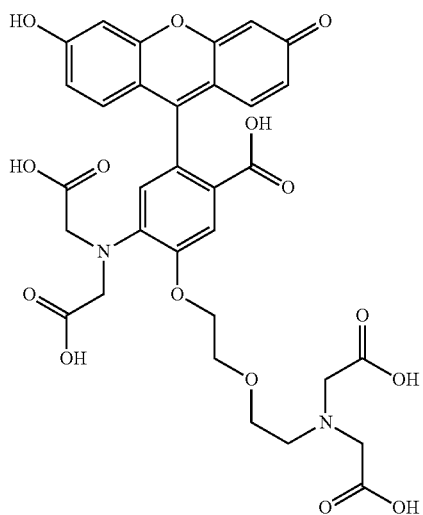

30

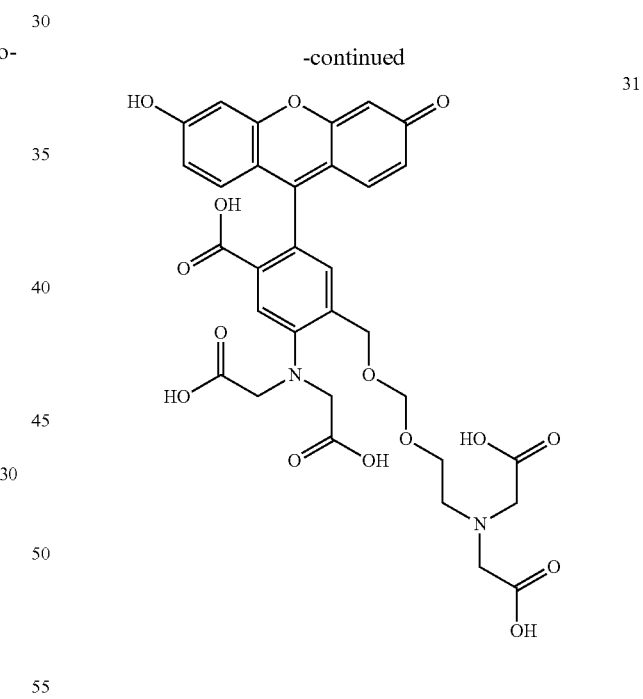

31

To the solution of compound 17 (1.5 g, 2.5 mmol) in methanesulfonic acid (15 mL), resorcinol (1 g, 9.1 mmol) is added at room temperature. The mixture is heated at 100° C. for 10 hours. Ice water (100 mL) is added to stop the reaction, followed by the addition of 5M NaOH solution to make the reaction mixture pH>12. The mixture is stirring at room temperature for 1 hour. The reaction mixture is purified by HPLC to give compound 30 (300 mg) and compound 31 (430 mg).

Example 22. Preparation of Compound 32

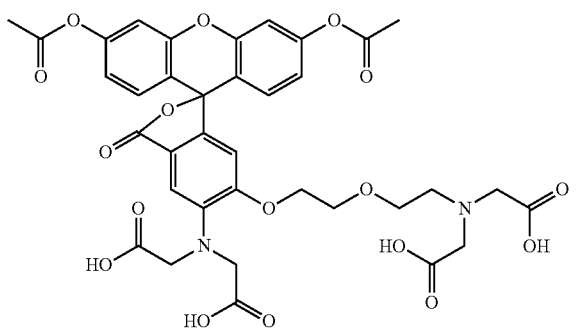 [SMILES: CC(=O)Oc1ccc2c(c1)Oc1cc(OC(C)=O)ccc1C21OC(=O)c2cc(N(CC(=O)O)CC(=O)O)c(OCCOCCN(CC(=O)O)CC(=O)O)cc21]

Compound 32 is prepared from Compound 30 analogously to the procedure of Compound 21.

Example 23. Preparation of Compound 33

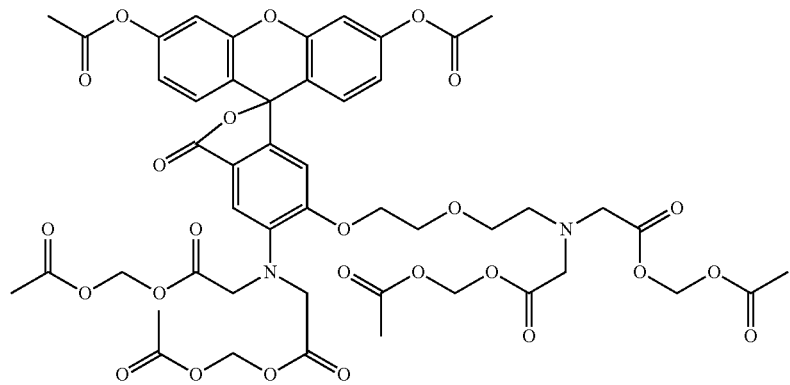 [SMILES: CC(=O)OCOC(=O)CN(CCOCCOc1cc2c(cc1N(CC(=O)OCOC(C)=O)CC(=O)OCOC(C)=O)C(=O)OC21c2ccc(OC(C)=O)cc2Oc2cc(OC(C)=O)ccc21)CC(=O)OCOC(C)=O]

Compound 33 is prepared from Compound 31 analogously to the procedure of Compound 22.

Example 24. Preparation of Compound 34

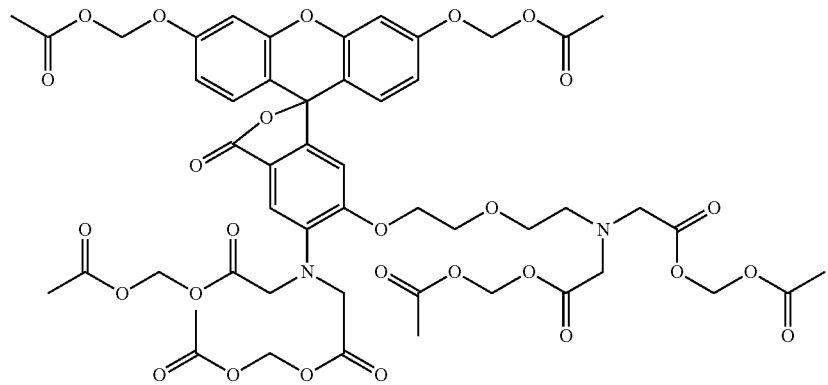 [SMILES: CC(=O)OCOC(=O)CN(CCOCCOc1cc2c(cc1N(CC(=O)OCOC(C)=O)CC(=O)OCOC(C)=O)C(=O)OC21c2ccc(OCOC(C)=O)cc2Oc2cc(OCOC(C)=O)ccc21)CC(=O)OCOC(C)=O]

Compound 34 is prepared from Compound 30 analogously to the procedure of Compound 23.

Example 25. Preparation of Compound 35

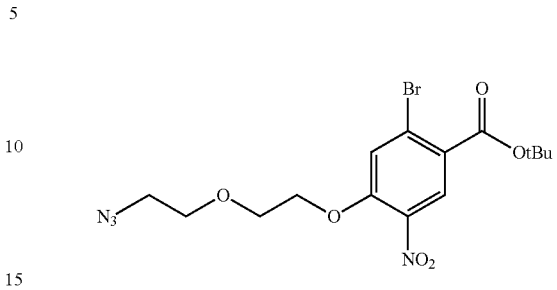

To the solution of 1-azido-2-(2-chloroethoxy)ethane (2.12 g, 6.66 mmol), tert-butyl 2-bromo-4-hydroxy-5-nitrobenzoate (1.05 g, 7.99 mmol) and $PPh_3$ (2.80 g, 10.66 mmol) in dry THF (20 mL) was added DIAD (2.1 mL, 10.66 mmol) dropwise at 0° C. in 30 min. The mixture is stirred at room temperature overnight. The solvent is removed in vacuo. Purification by flash chromatography on silica gel (Hexanes to 30% EtOAc) gives Compound 35 (1.79 g) as a light brown oil.

Example 26. Preparation of Compound 36

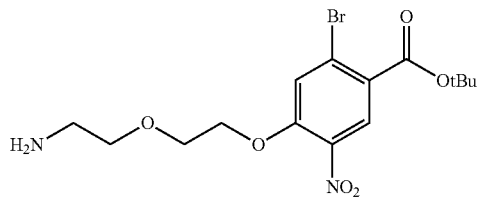 [SMILES: CC(C)(C)OC(=O)c1cc([N+](=O)[O-])c(OCCOCCN)cc1Br]

The mixture of 35 (4.66 g, 10.8 mmol) and SnCl₂ (8.19 g, 43.2 mmol) in MeOH (30 mL) is refluxed for 1 h. After cooling to room temperature, the solvent is removed in vacuo. The residue is dissolved in H₂O (100 mL). After filtration, the filtrate is purified by flash chromatography on C-18 column (0.1% TFA/H₂O to 30% acetonitrile). Lyophilization gives Compound 36 (3.33 g) as a light brown gel.

Example 27. Preparation of Compound 37

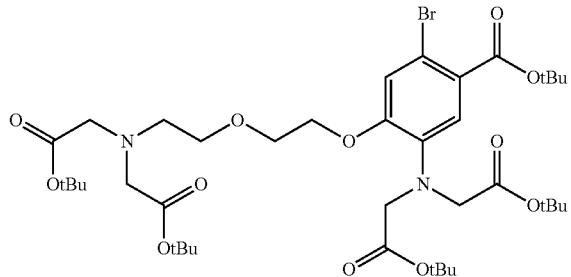 [SMILES: CC(C)(C)OC(=O)CN(CCOCCOc1cc(Br)c(C(=O)OC(C)(C)C)cc1N(CC(=O)OC(C)(C)C)CC(=O)OC(C)(C)C)CC(=O)OC(C)(C)C]

To the solution of 36 (3.33 g, 6.8 mmol) and tert-butylbromoacatate (10 mL, 68 mmol) in dry acetonitrile (40 mL) is added KI (564 mg, 3.4 mmol) followed by DIPEA (11.6 mL, 68 mmol) at room temperature. The mixture is refluxed for 24 h. After cooling to room temperature, the solvent is removed in vacuo. The residue is dried under high vacuum for 2 h. The residue is dissolved in dry acetonitrile (30 mL). tert-butylbromoacatate (3.38 mL, 22.88 mmol), KI (237 mg, 1.43 mmol) and proton sponge (1.84 g, 8.58 mmol) are added separately. The mixture is refluxed for 24 h. After cooling to room temperature, the mixture is filtered. The filtrate is dissolved in EtOAc (300 mL) and washed by pH 4 buffer (4×100 mL). The solvent is removed in vacuo. Purification by flash chromatography on silica gel (Hexanes to 40% EtOAc) gives Compound 37 (3.68 g) as a light brown oil.

Example 28. Preparation of Compound 38

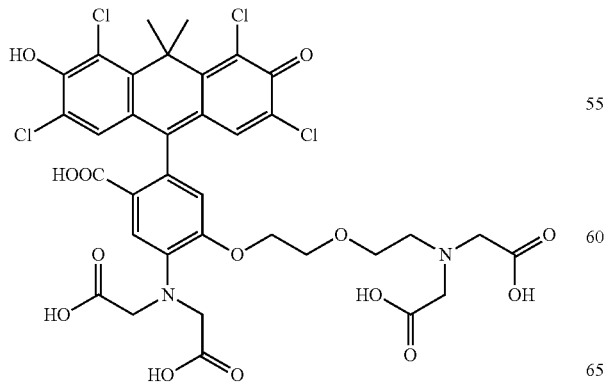

Compound 37 (220 mg) is dissolved in methyltetrahydrofuran (3 ml), and solution is cooled to −150° C. To the cold solution of Compound 37 is added 1.7 M t-BuLi (0.9 ml). The solution is stirred at −150° C. for 1 hour. To the solution of Compound 37 the solution of 2,4,5,7-tetrachloro-3,6-bis(methoxymethoxy)-10,10-dimethylanthracen-9 (10H)-one (240 mg, Tianjin Biolite) in methyltetrahydrofuran (3 ml) is carefully added to maintain the reaction solution around −150° C. The reaction solution is stirred at −150° C. for 2 hours. To the reaction mixture is carefully added 1:1 water/tetrahydrofuran (5 ml) to stop the reaction. The reaction mixture is extracted with EtOAc, and the organic phase is washed with brine, and dried over sodium sulfate. The EtOAc solution is evaporated under vacuum, and the residue is redissolved in dichloromethane (3 ml). To the dichloromethane solution is added trifluoroacetic acid (3 ml), and followed by the addition of anisole (0.1 ml), and stirred at room temperature until the solution change to red. The solution is evaporated under vacuum, and redissolved in water. The aqueous solution is washed with EtOAc for three times. The resulted aqueous solution is concentrated under high vacuum, and the residue is further purified on a C18 reverse phase silica gel column with a gradient of triethylammonium bicarbonate buffer/acetonitrile to give the desired Compound 38.

Example 29. Preparation of Compound 39

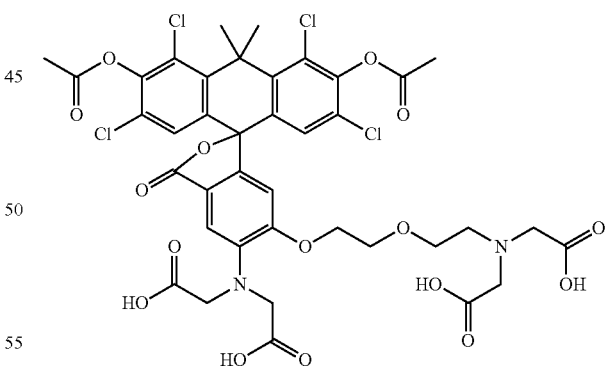

Compound 39 is prepared from Compound 38 analogously to the procedure of Compound 21.

Example 30. Preparation of Compound 40

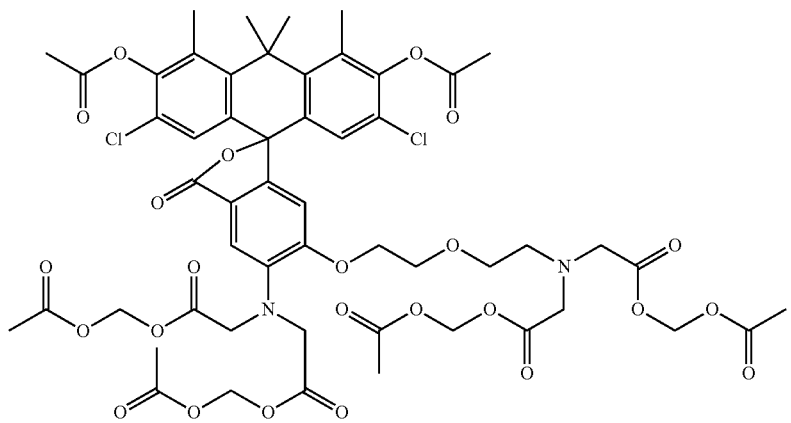 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OC(C)=O)c(C)c2C(C)(C)c2c1cc(Cl)c(OC(C)=O)c2C)CC(=O)OCOC(C)=O]

Compound 40 is prepared from Compound 39 analogously to the procedure of Compound 22.

Example 31. Preparation of Compound 41

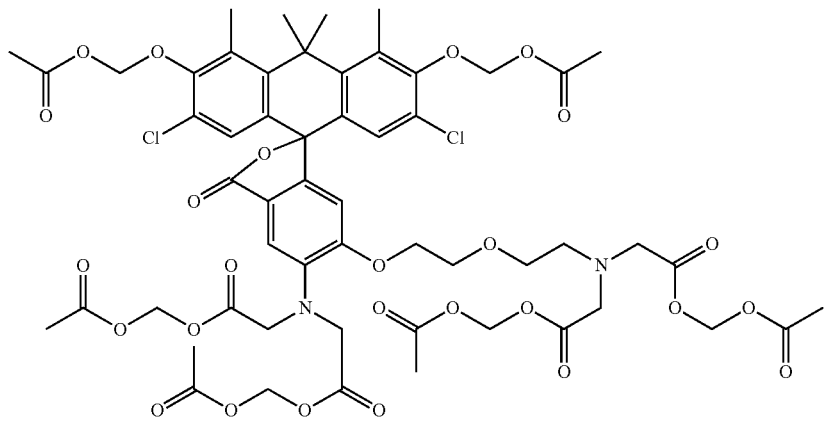 [SMILES: CC(=O)OCOC(=O)CN(CCOCCOc1cc2c(cc1N(CC(=O)OCOC(C)=O)CC(=O)OCOC(C)=O)C(=O)OC21c2cc(Cl)c(OCOC(C)=O)c(C)c2C(C)(C)c2c1cc(Cl)c(OCOC(C)=O)c2C)CC(=O)OCOC(C)=O]

Compound 41 is prepared from Compound 40 analogously to the procedure of Compound 23.

Example 32. Calcium Responses of the Fluorescent Indicators Measured Using a Microplate Reader Equipped with an Automated Liquid Handling System Calcium flux assays are preferred methods in drug discovery for screening G protein coupled receptors (GPCR). The fluorescent indicators of the present disclosure provide a homogeneous fluorescence-based assay for detecting the intracellular calcium mobilization. Cells expressing a GPCR of interest that signals through calcium are pre-loaded with the indicator AM esters (such as Fluo-3 AM, Fluo-4 AM, Compounds 22, 23, 24, 28, 33, 34, 40, 41 or 188) which can cross cell membrane. Once inside the cell, the lipophilic blocking groups are cleaved by non-specific cell esterase, resulting in a negatively charged fluorescein dye that is well-retained in cells, and its fluorescence is greatly enhanced upon binding to calcium. When the sample cells are stimulated with screening compounds, the receptor triggers a release of intracellular calcium, which then greatly increases the fluorescence of the intracellular indicators. The combination of long wavelength fluorescence properties, high sensitivity, and often a large increase in fluorescence upon binding with calcium makes the disclosed indicators well-suited for measurement of cellular calcium.

Figure 5:
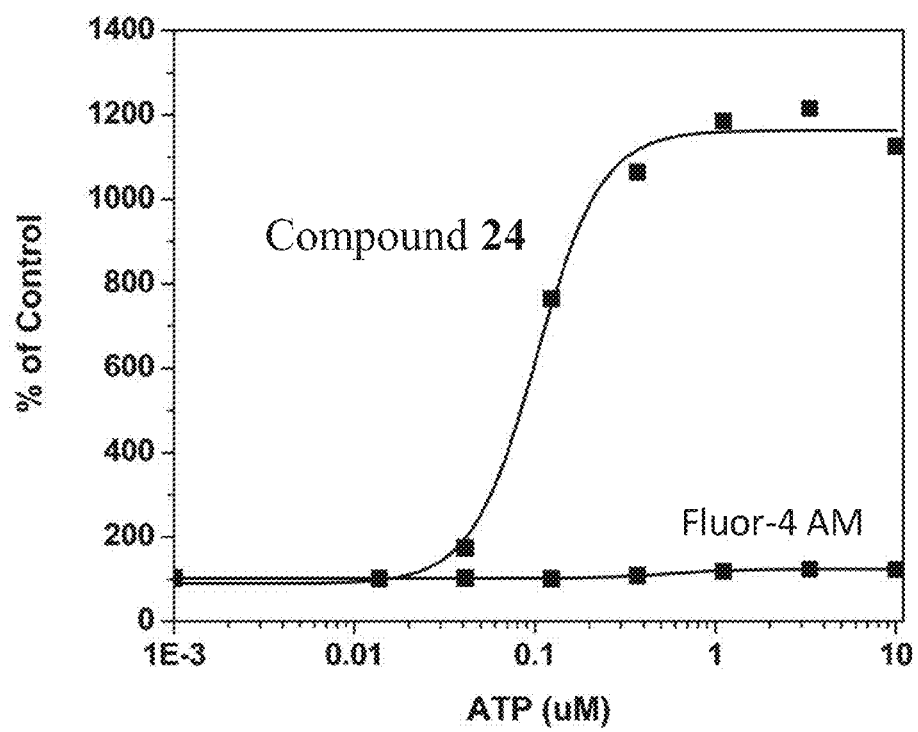
FIG. 5 shows a comparison of % response relative to control of Compound 24 and Fluo-4 AM in CHO-K1 cells in the absence of probenecid. CHO-K1 cells are seeded overnight at 50,000 cells per 100 μl per well in a 96-well black wall/clear bottom costar plate. The growth medium is removed, and the cells are incubated with 100 μl of Compound 24 and Fluo-4 AM at 5 μM in Hanks and Hepes buffer for 2 hours at 25° C. ATP (50 μL/well) is added by FlexStation to achieve the final desired concentrations.

Specifically, CHO cells stably transfected with muscarinic receptor 1 are plated at 60,000 cells per 100 µl per well in F12 with 5% FBS and 1% L-glutamine in a 96-well black wall/clear bottom Costar plate, incubated in 5% $CO_2$, 37° C. incubator overnight. The growth medium is removed and the cells are incubated with 100 µL/well of 1-8 µM a reference compound (Fluo-3 AM, Fluo-4 AM, BAPTA bodipy AM or BAPTA fluorescein AM) or a calcium indicator of the present disclosure (Compounds 22, 23, 24, 28, 33, 34, 40, 41 or 188) in Hanks and HEPES buffer with 0 mM or 2.5 mM probenecid for 1 hour AT 37° C. and 5% $CO_2$. Carbachol (50 µl/well) is added by FlexStation (Molecular Devices) to achieve the final indicated concentration. A representative dose response is shown in FIG. 5.

Figure 2:
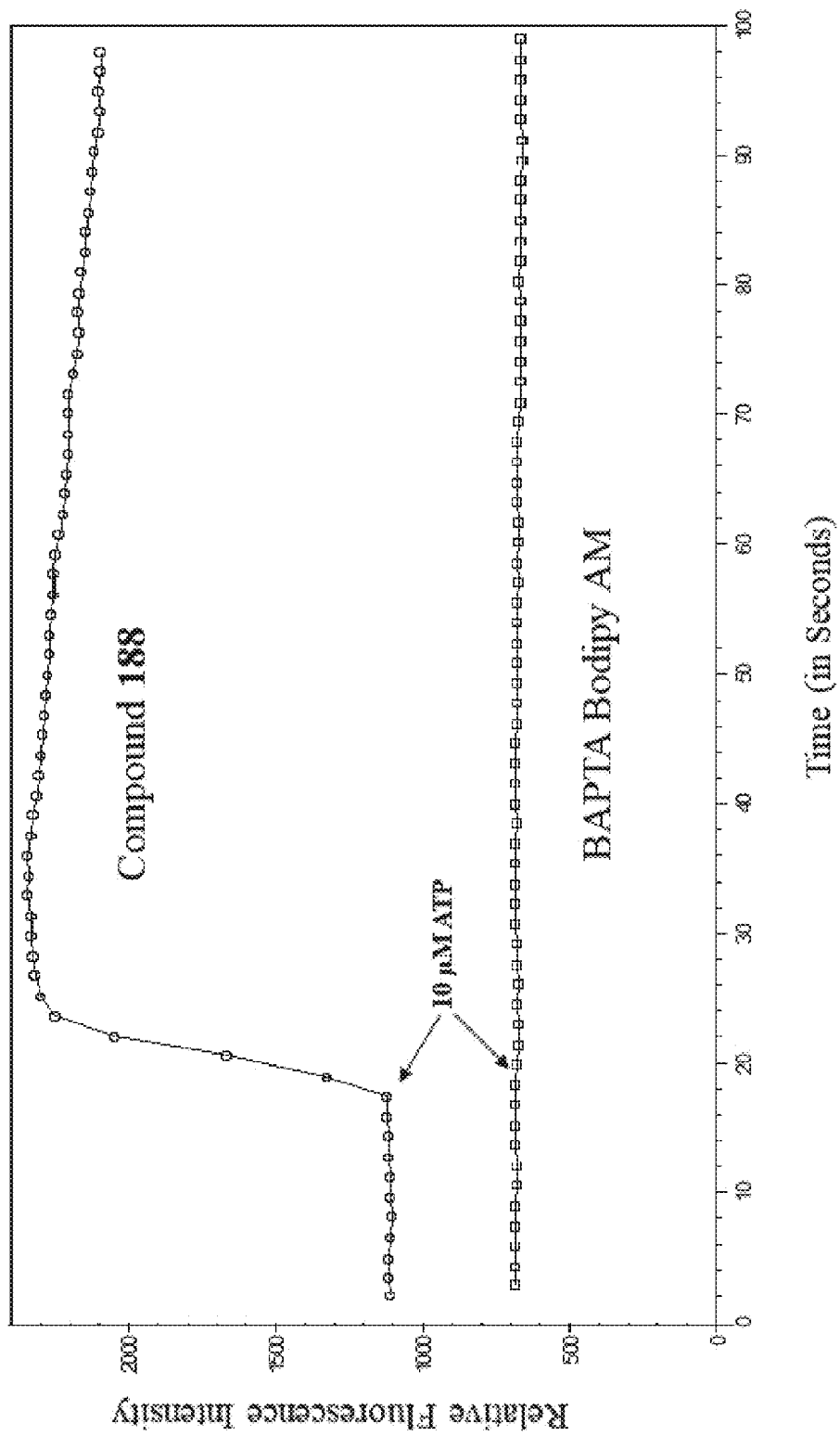
FIG. 2 shows a time course comparison of relative fluorescence of Compound 188 and BAPTA Bodipy AM in CHO-K1 cells in the presence of probenecid. CHO-K1 cells are seeded overnight at 50,000 cells per 100 μl per well in a 96-well black wall/clear bottom costar plate. The growth medium is removed, and the cells are incubated with 100 μl of Compound 188 and BAPTA Bodipy AM at 5 μM in Hanks and Hepes buffer in the presence of 2.5 mM probenecid for 1 hour at 37° C., 5% $CO_2$ incubator. ATP (10 μM) is added by FlexStation to stimulate cell calcium, and the time-dependent calcium response is monitored with FlexStation.

FIG. 2 shows a time course comparison of relative fluorescence of Compound 188 and BAPTA Bodipy AM in CHO-KI cells in the presence of probenecid. CHO-KI cells are seeded overnight at 50,000 cells per 100 μl per well in a 96-well black wall/clear bottom costar plate. The growth medium is removed, and the cells are incubated with 100 μl of Compound 188 and BAPTA Bodipy AM at 5 μM in Hanks and Hepes buffer in the presence of 2.5 mM probenecid for 1 hour at 37° C., 5% $CO_2$ incubator. ATP (10 μM) is added by FlexStation to stimulate cell calcium, and the time-dependent calcium response is monitored with FlexStation.

Figure 3:
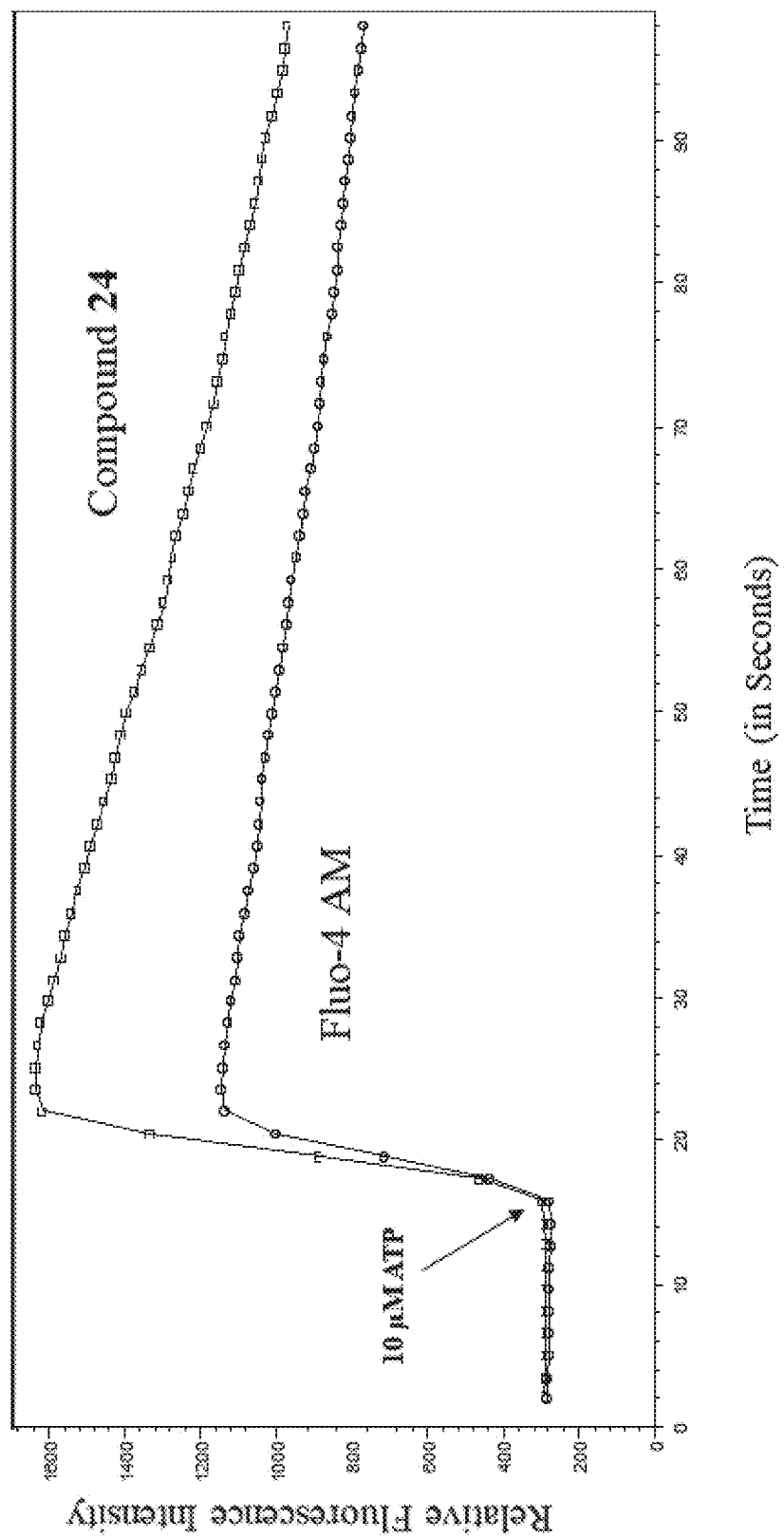
FIG. 3 shows a time course comparison of relative fluorescence of Compound 24 and Fluo-4 AM in CHO-K1 cells in the presence of probenecid. CHO-K1 cells are seeded overnight at 50,000 cells per 100 μl per well in a 96-well black wall/clear bottom costar plate. The growth medium is removed, and the cells are incubated with 100 μl of Compound 24 and Fluo-4 AM at 5 μM in Hanks and Hepes buffer in the presence of 2.5 mM probenecid for 1 hour at 37° C., 5% $CO_2$ incubator. ATP (10 μM) is added by FlexStation to stimulate cell calcium, and the time-dependent calcium response is monitored with FlexStation.

FIG. 3 shows a time course comparison of relative fluorescence of Compound 24 and Fluo-4 AM in CHO-K cells in the presence of probenecid. CHO-K cells are seeded overnight at 50,000 cells per 100 μl per well in a 96-well black wall/clear bottom costar plate. The growth medium is removed, and the cells are incubated with 100 μl of Compound 24 and Fluo-4 AM at 5 μM in Hanks and Hepes buffer in the presence of 2.5 mM probenecid for 1 hour at 37° C., 5% $CO_2$ incubator. ATP (10 μM) is added by FlexStation to stimulate cell calcium, and the time-dependent calcium response is monitored with FlexStation.

Figure 4:
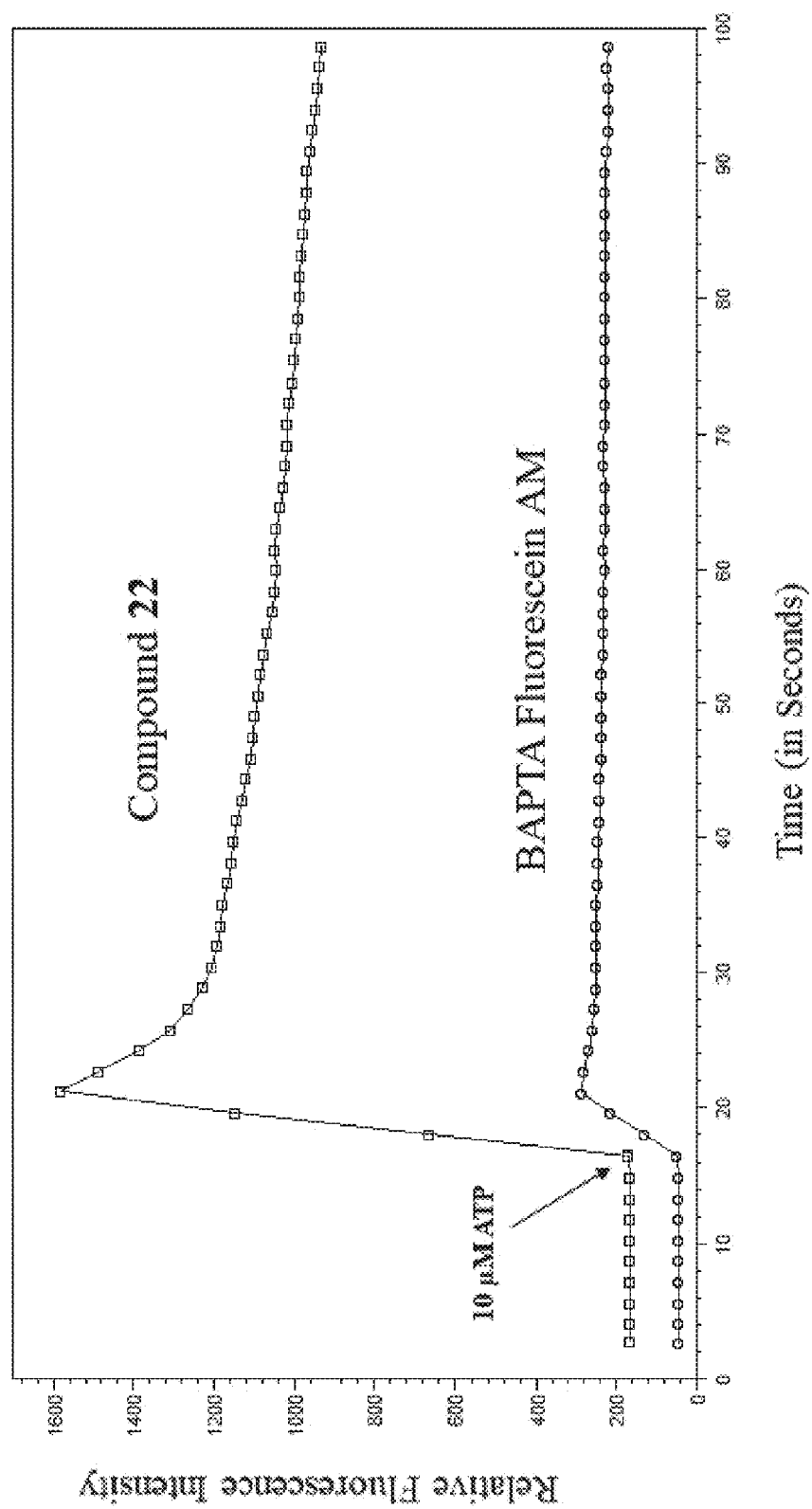
FIG. 4 shows a time course comparison of relative fluorescence of Compound 22 and BAPTA Fluorescein AM in CHO-K1 cells in the presence of probenecid. CHO-K1 cells are seeded overnight at 50,000 cells per 100 μl per well in a 96-well black wall/clear bottom costar plate. The growth medium is removed, and the cells are incubated with 100 μl of Compound 22 and BAPTA Fluorescein AM at 5 μM in Hanks and Hepes buffer in the presence of 2.5 mM probenecid for 2 hours at 37° C., 5% $CO_2$ incubator. ATP (10 μM) is added by FlexStation to stimulate cell calcium, and the time-dependent calcium response is monitored with FlexStation.

FIG. 4 shows a time course comparison of relative fluorescence of Compound 22 and BAPTA Fluorescein AM in CHO-K1 cells in the presence of probenecid. CHO-K1 cells are seeded overnight at 50,000 cells per 100 μl per well in a 96-well black wall/clear bottom costar plate. The growth medium is removed, and the cells are incubated with 100 μl of Compound 22 and BAPTA Fluorescein AM at 5 μM in Hanks and Hepes buffer in the presence of 2.5 mM probenecid for 2 hours at 37° C., 5% $CO_2$ incubator. ATP (10 μM) is added by FlexStation to stimulate cell calcium, and the time-dependent calcium response is monitored with FlexStation.

FIG. 5 shows a comparison of % response relative to control of Compound 24 and Fluo-4 AM in CHO-K1 cells in the absence of probenecid. CHO-KI cells are seeded overnight at 50,000 cells per 100 μl per well in a 96-well black wall/clear bottom costar plate. The growth medium is removed, and the cells are incubated with 100 μl of Compound 24 and Fluo-4 AM at 5 μM in Hanks and Hepes buffer for 2 hours at 25° C. ATP (50 μL/well) is added by FlexStation to achieve the final desired concentrations.

Compound 24 is loaded into cells much faster than Fluo-4 AM, the "gold" standard of green fluorescent calcium indicators. In addition, in the absence of probenecid Compound 24 demonstrates the unexpected better fluorescence intensity enhancement upon calcium stimulation than that of Fluo-4 AM.

Figure 6A:
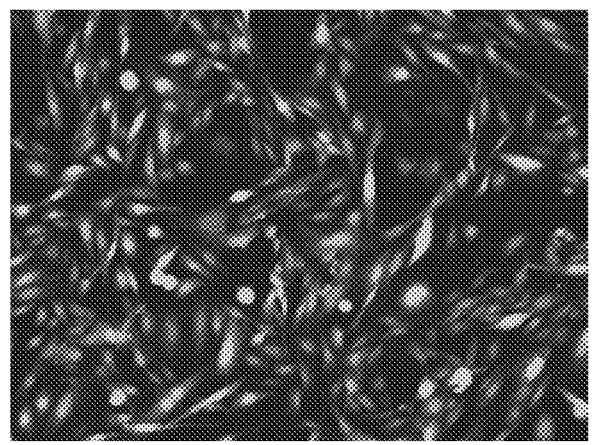
FIG. 6A to FIG. 6B, show fluorescence microscope images of HEKF cells incubated with BAPTA Fluorescein AM (FIG. 6A) or Compound 22 (FIG. 6B). HEK cells are seeded overnight at 40,000 cells/100 UL/well in a 96-well black wall/clear bottom costar plate. The growth medium is removed, and the cells are incubated with 100 μL of BAPTA Fluorescein AM, or Compound 22 in HHBS at a concentration of 5 μM in a 37° C., 5% $CO_2$ incubator for 1 hour. The cells are stimulated with 10 μM ATP, and washed twice with 200 μL HHBS, then treated with 10 μM ATP. All the images are taken with a fluorescence microscope (Olympus IX71) using FITC channel.
Figure 6B:
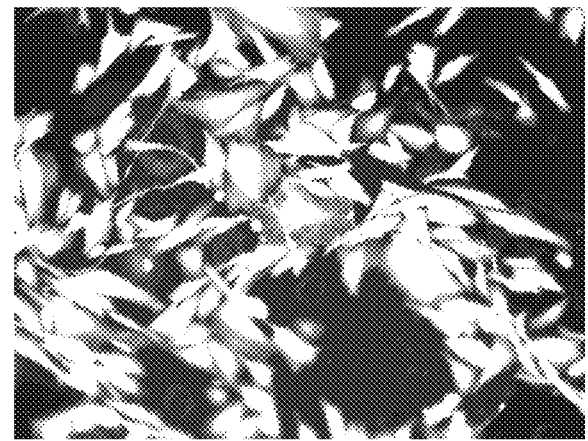

FIG. 6A-FIG. 6B show fluorescence microscope images of HEKF cells incubated with BAPTA Fluorescein AM (FIG. 6A) or Compound 22 (FIG. 6B). HEK cells are seeded overnight at 40,000 cells/100 μL/well in a 96-well black wall/clear bottom costar plate. The growth medium is removed, and the cells are incubated with 100 μL of BAPTA Fluorescein AM, or Compound 22 in HHBS at a concentration of 5 μM in a 37° C., 5% $CO_2$ incubator for 1 hour. The cells are stimulated with 10 μM ATP, and washed twice with 200 μL HHBS, then treated with 10 μM ATP. All the images are taken with a fluorescence microscope (Olympus IX71) using FITC channel.

Notwithstanding the appended claims, the disclosure set forth herein is also defined by the following clauses:

Clause 1. A fluorogenic calcium indicator of Formula 1:

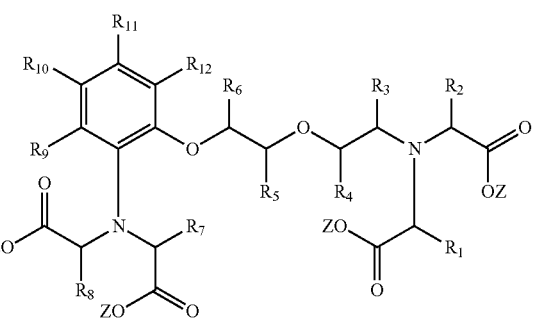

Formula 1 wherein:

$R_1$-$R_8$ are independently H, an alkyl, an aryl or a heteroaryl;

$R_9$-$R_{12}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl, a heteroaryl, a heterocycle or a fluorophore moiety;

Z is H, a counter cation, or an alkyl having 1-10 carbons;

wherein at least one of $R_9$-$R_{12}$ is a fluorophore moiety or any two of $R_9$-$R_{12}$ are cyclically linked together with ring A to define a fluorophore moiety comprising a benzo-fused aryl, heteroaryl or heterocycle ring.

Clause 2. The compound of clause 1, wherein Z is an acyloxymethyl having 1-10 carbons.

Clause 3. The compound of clause 1, wherein:

$R_1$-$R_8$ are independently H or alkyl;

$R_9$-$R_{12}$ are independently H, halogen, an alkyl, carboxy, acyloxymethylcarbonyl, an alkoxy, an aryloxy, thiol, an alkylthiol, an arylthiol, azido, nitro, cyano, an amino, hydroxy, a carbonyl, a boronyl, an aryl or a heteroaryl; and Z is acetoxymethyl.

Clause 4. The compound of clause 1, wherein:

$R_1$-$R_8$ are independently H or methyl;

$R_9$-$R_{12}$ are independently H, halogen, an alkyl, carboxy, acyloxymethylcarbonyl, alkoxy, azido aryl or heteroaryl; and Z is acetoxymethyl.

Clause 5. The compound of clause 1, wherein:

$R_1$-$R_8$ are independently H or methyl:

$R_9$-$R_{12}$ are independently H, halogen, an alkyl, carboxy, acyloxymethylcarbonyl, alkoxy, nitro, aryl or heteroaryl;

Z is acetoxymethyl; and the fluorophore moiety is selected from a fluorescein, a rhodamine, a cyanine, a bodipy, a squaraine, a pyrene, an indole, an furan, a pyrylium, a thiazole, quinoline, a fluorene, an acridine, an acridone, a phenazine, a phenanthroline, a carbazole, a pyridine, a pyrimidine, a purine, a quinolizine, a quinoxaline, a naphthyridine, a phthalazine, a pyridopyrimidine, a pteridine, a chromone, a thiophene, an oxadiazole, an oxatriazole, a thiadiazole, a pyranopyrrole, a furopyridine, an oxazolopyridine, a benzoisothiazole, a thienopyridine, a phenoxazine, a phenothiazine, a ruthenium complex, an europium complex, a terbium complex, a perylenediimide, a coumarin, an oxazine, an oxazole and a phthalocyanine.

Clause 6. The compound of clause 1, wherein:
$R_1$-$R_8$ are H;
$R_9$-$R_{12}$ are independently H, fluoro, an alkyl, carboxy, an acyloxymethylcarbonyl, an alkoxy, azido, an aryl or a heteroaryl;
Z is acetoxymethyl:
at least one of $R_9$-$R_{12}$ is selected from a fluorescein, a rhodamine, a bodipy, an indole, a furan, a coumarin, an oxazine, and an oxazole.

Clause 7. The compound of clause 1, wherein the compound is a fluorogenic calcium indicator of Formula 2 or 3:

Formula 2

Formula 3 wherein:
$R_1$-$R_8$ are independently H, an alkyl, an aryl or a heteroaryl;
$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;
X and Z are independently H, a counter cation, an acyl, an acyloxymethyl, or an alkyl having 1-10 carbons; and
Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

Clause 8. The compound of clause 7, wherein X and Z are independently an acyl or an acyloxymethyl having 1-10 carbons.

Clause 9. The compound of clause 8, wherein X and Z are independently acetyl or acetoxymethyl.

Clause 10. The compound of clause 7, wherein:
$R_1$-$R_8$ are independently H or alkyl;
$R_9$-$R_{18}$ are independently H, an alkyl, chloro, fluoro, carboxy, an acyloxymethylcarbonyl, an alkoxy, cyano, an amino or hydroxy;
X and Z are independently H, a metal ion, an ammonium, an acyl, an acyloxymethyl, or an alkyl having 1-10 carbons; and
Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

Clause 11. The compound of clause 7, wherein:
$R_1$-$R_8$ are independently H or methyl; $R_9$-$R_{12}$ are independently H, alkyl, chloro, fluoro, an acyloxymethylcarbonyl, an alkoxy or nitro;
$R_{13}$-$R_{18}$ are independently H, chloro or fluoro;
X and Z are independently H, a metal ion, an ammonium, an acyl, an acyoxymethyl or an alkyl having 1-10 carbons; and Y is O, N—R$_{25}$, O=P—R$_{25}$, R$_{25}$—C—R$_2$, or R$_{25}$—Si—R$_{26}$ wherein R$_{25}$ and R$_{26}$ are independently H, an alkyl, an aryl or a heteroaryl.

Clause 12. The compound of clause 7, wherein:
$R_1$-$R_8$ are H;
$R_9$-$R_{12}$ are independently H, alkyl, chloro, fluoro, an acyloxymethylcarbonyl, an alkoxy or nitro;
$R_{13}$-$R_{18}$ are independently H, chloro or fluoro;
X is acetyl or acetoxymethyl;
Y is O, O=P—R$_{25}$, R$_{25}$—C—R$_{26}$, or R$_{25}$—Si—R$_{26}$ wherein R$_{25}$ and R$_{26}$ are an alkyl; and
Z is acetoxymethyl.

Clause 13. The compound of clause 1, wherein the compound is a fluorogenic calcium indicator of Formula 4 or 5:

Formula 4

163

-continued

Formula 5

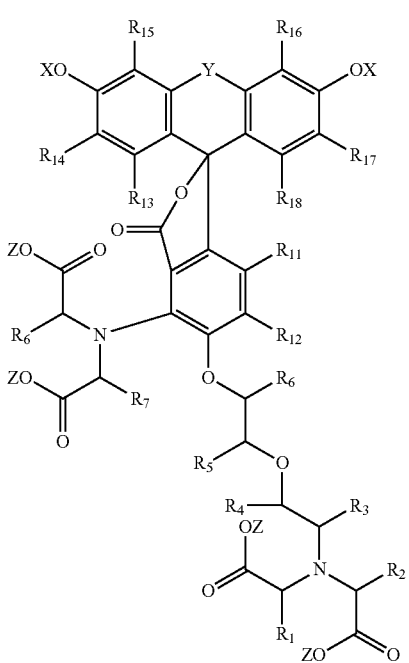

wherein:

$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

X and Z are independently an acyl or an acyloxymethyl having 1-10 carbons; and

Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

Clause 14. The compound of clause 13, wherein X and Z are acetyl or acetoxymethyl.

Clause 15. The compound of clause 13, wherein:

$R_1$-$R_8$ are independently H or alkyl;

$R_9$-$R_{18}$ are independently H, alkyl, chloro, fluoro, an alkoxy, azido, nitro, cyano, amino or hydroxy;

X is acetyl or acetoxymethyl;

Y is O, O=P—R$_{25}$, R$_{25}$—C—R$_{26}$, or R$_{25}$—Si—R$_{26}$ wherein R$_{25}$ and R$_{26}$ are an alkyl; and Z is acetoxymethyl.

Clause 16. The compound of clause 13, wherein:

$R_1$-$R_8$ are independently H or methyl;

$R_9$-$R_{12}$ are independently H, alkyl, chloro, fluoro, an alkoxy or nitro:

$R_{13}$-$R_{18}$ are independently H, chloro or fluoro;

X is acetyl or acetoxymethyl

Y is O, O=P—R$_{25}$, R$_{25}$—C—R$_{26}$, or R$_{25}$—Si—R$_{26}$ wherein R$_{25}$ and R$_{26}$ are an alkyl; and Z is acetoxymethyl.

164

Clause 17. The compound of clause 13, wherein:

$R_1$-$R_8$ are H:

$R_9$-$R_{12}$ are independently H, alkyl, chloro, fluoro, alkoxy or nitro;

$R_{13}$-$R_{18}$ are independently H, chloro or fluoro; X is acetyl or acetoxymethyl;

Y is O, O=P—R$_{25}$, R$_{25}$—C—R$_{26}$, or R$_{25}$—Si—R$_{26}$ wherein R$_{25}$ and R$_{26}$ are methyl, ethyl, propyl or butyl; and Z is acetoxymethyl.

Clause 18. The compounds of clause 1, wherein the compound is a fluorogenic calcium indicator Formula 6 or 7:

Formula 6

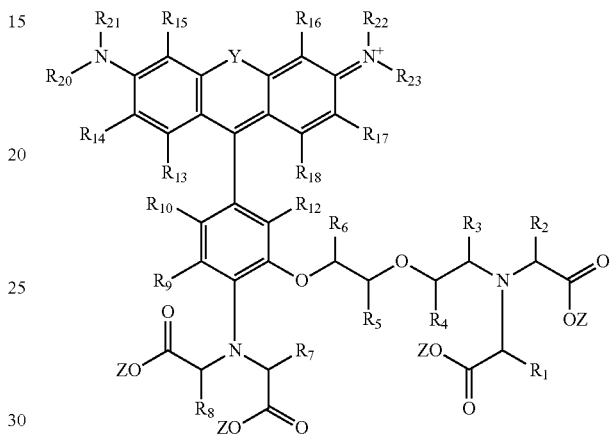

Formula 7

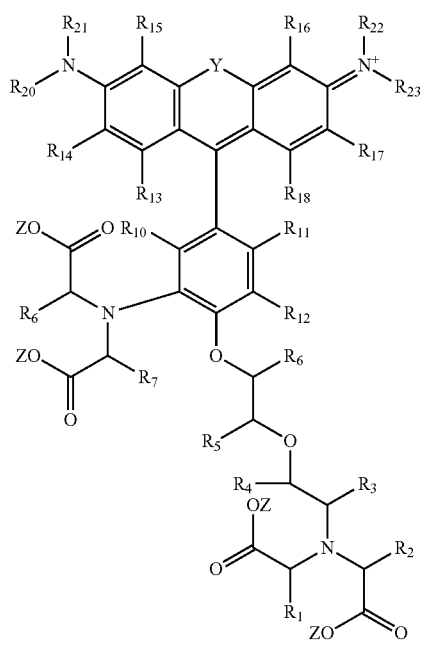

wherein:

$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

$R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 3-8 membered ring;

Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, P—R$_{25}$, O=P—R$_{25}$, R$_{25}$—C—R$_{26}$, or R$_{25}$—Si—R$_{26}$ wherein $R_{25}$ and $R_{26}$ are independently H, an alkyl, an aryl or a heteroaryl; and Z is H, a counter cation, an acyl, an acyloxymethyl, or an alkyl having 1-10 carbons.

Clause 19. The compound of clause 18, wherein Z is an acyloxymethyl having 1-10 carbons.

Clause 20. The compound of clause 18, wherein Z is acetoxymethyl.

Clause 21. The compound of clause 18, wherein:

$R_1$-$R_8$ are independently H or alkyl;

$R_9$-$R_{18}$ are independently H, an alkyl, chloro, fluoro, carboxy, an acyloxymethylcarbonyl, an alkoxy, cyano, an amino or hydroxy; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{21}$ and $R_{17}$, or $R_{22}$ and $R_{23}$ combine to form a 5- or 6-membered ring;

Y is O, N—R$_{25}$, O=P—R$_{25}$, R$_{25}$—C—R$_{26}$, or R$_{25}$—Si—R$_{26}$ wherein $R_{25}$ and $R_{26}$ are independently H, an alkyl, an aryl or a heteroaryl; and Z is H, a metal ion, an ammonium, an acyl, an acyloxymethyl, or an alkyl having 1-10 carbons.

Clause 22. The compound of clause 18, wherein:

$R_1$-$R_8$ are independently H or methyl;

$R_9$-$R_{12}$ are independently H, alkyl, chloro, fluoro, an acyloxymethylcarbonyl, an alkoxy or nitro;

$R_{13}$-$R_{12}$ are independently H, chloro or fluoro;

$R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring;

Y is O, N—R$_{25}$, O=P—R$_{25}$, R$_{25}$—C—R$_{26}$, or R$_{25}$—Si—R$_{26}$ wherein $R_{25}$ and $R_{26}$ are independently H, an alkyl, an aryl or a heteroaryl; and Z is H, a metal ion, an ammonium, an acyl, an acyoxymethyl or an alkyl having 1-10 carbons.

Clause 23. The compound of clause 18, wherein:

$R_1$-$R_8$ are H;

$R_9$-$R_{12}$ are independently H, alkyl, chloro, fluoro, an acyloxymethylcarbonyl, an alkoxy or nitro;

$R_{13}$-$R_{18}$ are independently H, chloro or fluoro; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring;

Y is O, O=P—R$_{25}$, R$_{25}$—C—R$_{26}$, or R$_{25}$—Si—R$_{26}$ wherein $R_{25}$ and $R_{26}$ are an alkyl; and Z is acetoxymethyl.

Clause 24. The compound of clause 1, wherein the compound is a fluorogenic calcium indicator of Formula 8 or 9:

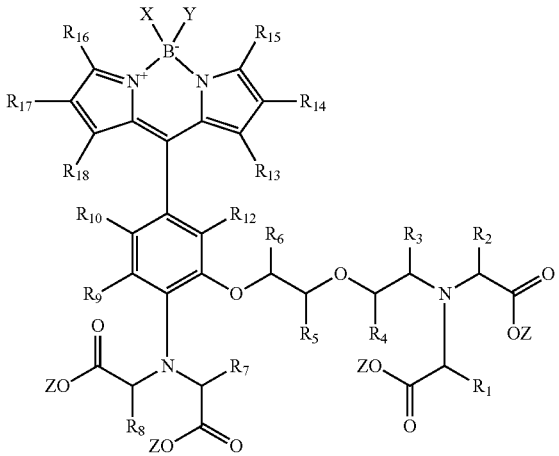

Formula 8

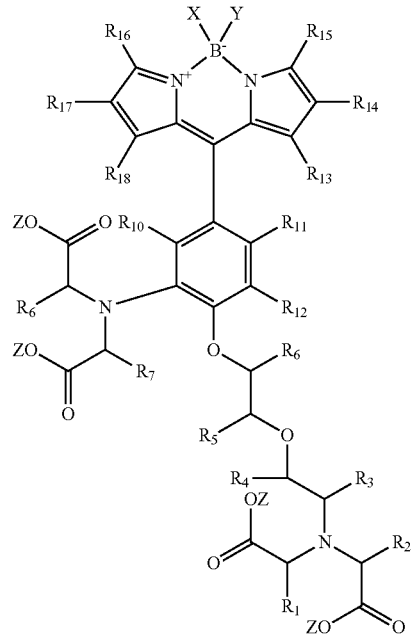

Formula 9 wherein:

$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; wherein $R_{13}$ and $R_{14}$, $R_{14}$ and $R_{15}$, $R_{17}$ and $R_{18}$, and/or $R_{16}$ and $R_{17}$ are optionally cyclically linked to form a 5- or 6-membered fused aromatic ring or a heteroaryl ring;

X and Y are independently F, an alkynyl, an alkoxy or an aryloxy; and

Z is H, a counter cation, an acyl, an acyloxymethyl, or an alkyl having 1-10 carbons.

Clause 25. The compound of clause 24, wherein Z is an acyloxymethyl having 1-10 carbons.

Clause 26. The compound of clause 24, wherein Z is acetoxymethyl.

Clause 27. The compound of clause 24, wherein:

$R_1$-$R_8$ are independently H or alkyl;

$R_9$-$R_{18}$ are independently H, an alkyl, chloro, fluoro, an acyloxymethylcarbonyl, an alkoxy, cyano, aryl or a heteroaryl; wherein $R_{13}$ and $R_{14}$, $R_{14}$ and $R_{15}$, $R_{17}$ and $R_{15}$, and/or $R_{16}$ and $R_{17}$ are optionally cyclically linked to form a 5- or 6-membered fused aromatic ring or a heteroaryl ring;

X and Y are independently F or an alkoxy; and

Z is an acyloxymethyl having 1-10 carbons.

Clause 28. The compound of clause 24, wherein:

$R_1$-$R_8$ are H;

$R_9$-$R_{18}$ are independently H, an alkyl, chloro, fluoro, an acyloxymethylcarbonyl, an alkoxy, cyano, aryl or a heteroaryl; wherein $R_{13}$ and $R_{14}$, $R_{14}$ and $R_{15}$, $R_{17}$ and $R_{15}$, and/or $R_{16}$ and $R_{17}$ are optionally cyclically linked to form a 5- or 6-membered fused aromatic ring or a heteroaryl ring;

X and Y are F; and

Z is acetoxymethyl.

Clause 29. The compound of any one of clauses 1-28, wherein the compound has the structure of a compound of Table 2, or a salt thereof.

Clause 30. A method of detecting intracellular calcium, the method comprising:

a) contacting a sample containing a cell with a compound according to any one of clauses 1-29:

b) incubating the sample for a time sufficient for the compound to be loaded into the cell and an indicator compound to be generated intracellularly;

c) illuminating the sample with incident light at a wavelength that generates a fluorescence response from the indicator compound;

d) detecting a fluorescence response from the indicator compound.

Clause 31. The method of clause 30, further comprising:

stimulating the cell;

monitoring the fluorescence response from the indicator compound to detect changes in intensity; and correlating the changes in fluorescence intensity with changes in intracellular calcium levels.

Clause 32. The method of clause 30 or 31, wherein the compound is a cell-permeant dye indicator of Formula 2 or 3:

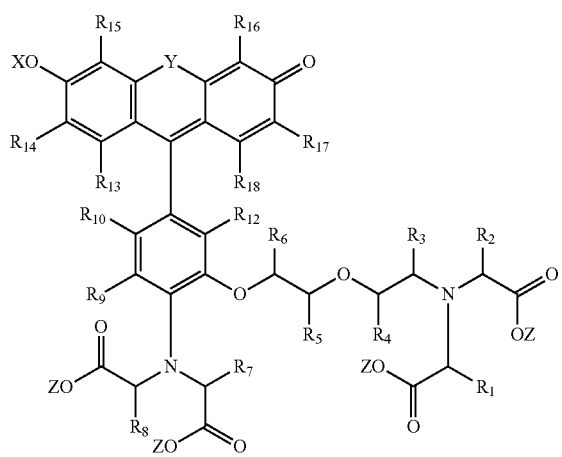

Formula 2

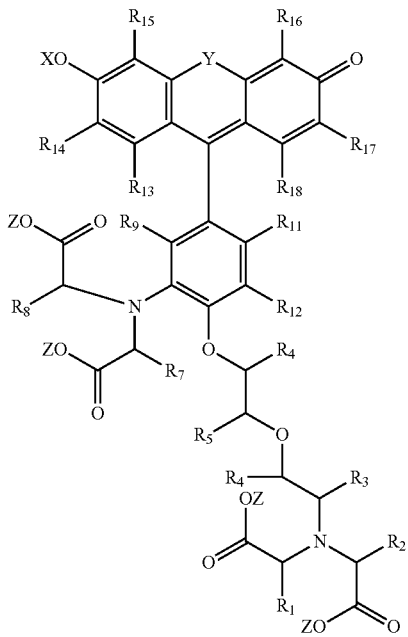

Formula 3 wherein:

$R_1$-$R_8$ are H:

$R_9$-$R_{12}$ are independently H, alkyl, chloro, fluoro, an acyloxymethylcarbonyl, an alkoxy or nitro;

$R_{13}$-$R_{18}$ are independently H, chloro or fluoro;

X is acetyl or acetoxymethyl;

Y is O, O=P—$R_{25}$, $R_{25}$—C—$R_{25}$, or $R_{25}$—Si—$R_{26}$ wherein $R_{25}$ and $R_{26}$ are an alkyl; and Z is acetoxymethyl.

Clause 33. The method of clause 30 or 31, wherein the compound is a cell-permeant dye indicator of Formula 4 or 5:

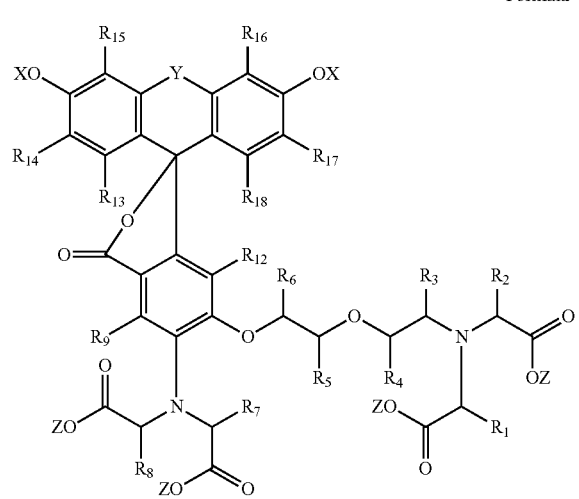

Formula 4

169
-continued

Formula 5

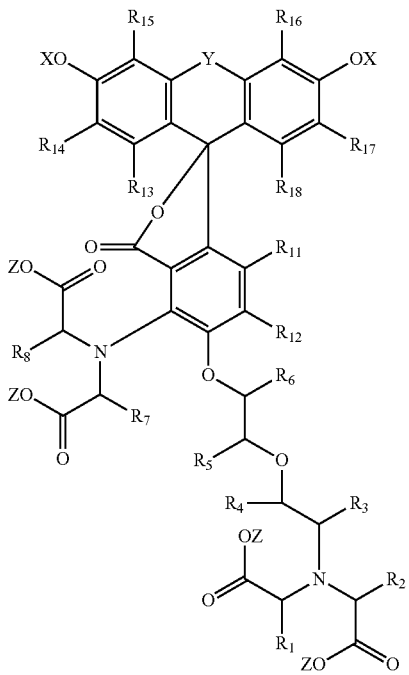

wherein:

$R_1$-$R_8$ are H;

$R_9$-$R_{12}$ are independently H, alkyl, chloro, fluoro, alkoxy or nitro;

$R_{13}$-$R_{18}$ are independently H, chloro or fluoro;

X is acetyl or acetoxymethyl;

Y is O, O=P—$R_{25}$, $R_{25}$—C—$R_{25}$, or $R_{25}$—Si—$R_{26}$ wherein $R_{25}$ and $R_{26}$ are methyl, ethyl, propyl or butyl; and Z is acetoxymethyl.

Clause 34. The method of clause 30 or 31, wherein the compound is a cell-permeant dye indicator of Formula 8 or 9:

Formula 8

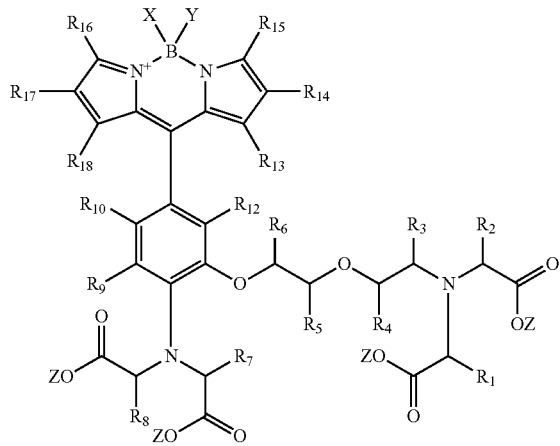

170
-continued

Formula 9

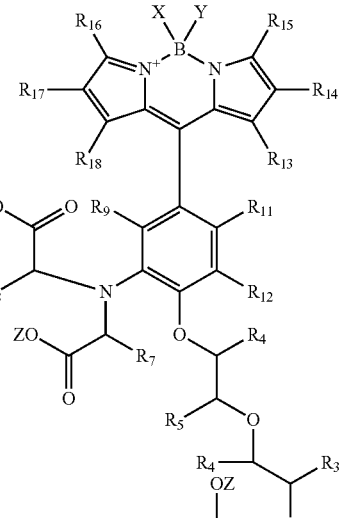

wherein:

$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

$R_{13}$ and $R_{14}$, $R_{14}$ and $R_{15}$, $R_{17}$ and $R_{18}$, and/or $R_{16}$ and $R_{17}$ are optionally cyclically linked to form a 5- or 6-membered fused aromatic ring or a heteroaryl ring:

X and Y are independently F, an alkynyl, an alkoxy or an aryloxy; and

Z is acetoxymethyl.

Clause 35. A kit for performing a calcium assay, the kit comprising:

a compound of clause 1; and an additional component selected from a calibration standard of a target ion, an ionophore, a fluorescence standard, a fluorophore, a quencher, an aqueous buffer, a surfactant and an organic solvent.

Clause 36. The kit of clause 35, wherein the additional component is a non-fluorescent and cell-impermeant quencher dye.

Clause 37. The kit of clause 36, wherein the non-fluorescent and cell-impermeant quencher dye is mixed with the compound as a mixed powder or mixed solution.

Clause 38. The kit of clause 36, wherein the non-fluorescent and cell-impermeant quencher dye is provided in a separate container.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the following.

What is claimed is:

1. A fluorogenic calcium indicator of Formula 1:

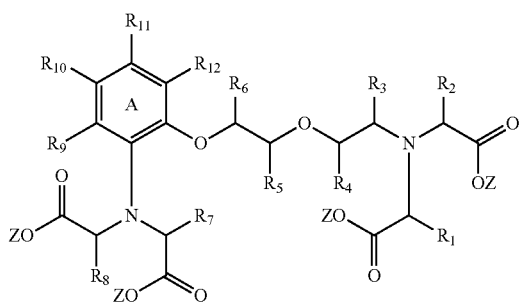

Formula 1 wherein:
$R_1$-$R_8$ are independently H, an alkyl, an aryl or a heteroaryl;
$R_9$-$R_{12}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl, a heteroaryl, a heterocycle or a fluorophore moiety;
Z is H, a counter cation, or an alkyl having 1-10 carbons;
wherein at least one of $R_9$-$R_{12}$ is a fluorophore moiety or any two of $R_9$-$R_{12}$ are cyclically linked together with ring A to define a fluorophore moiety comprising a benzo-fused aryl, heteroaryl or heterocycle ring.

2. The compound of claim 1, wherein:
$R_1$-$R_8$ are independently H or alkyl;
$R_9$-$R_{12}$ are independently H, halogen, an alkyl, carboxy, acyloxymethylcarbonyl, an alkoxy, an aryloxy, thiol, an alkylthiol, an arylthiol, azido, nitro, cyano, an amino, hydroxy, a carbonyl, a boronyl, an aryl or a heteroaryl; and
Z is acetoxymethyl.

3. The compound of claim 1, wherein:
$R_1$-$R_8$ are independently H or methyl;
$R_9$-$R_{12}$ are independently H, halogen, an alkyl, carboxy, acyloxymethylcarbonyl, alkoxy, nitro, aryl or heteroaryl;
Z is acetoxymethyl; and
the fluorophore moiety is selected from a fluorescein, a rhodamine, a cyanine, a bodipy, a squaraine, a pyrene, an indole, an furan, a pyrylium, a thiazole, quinoline, a fluorene, an acridine, an acridone, a phenazine, a phenanthroline, a carbazole, a pyridine, a pyrimidine, a purine, a quinolizine, a quinoxaline, a naphthyridine, a phthalazine, a pyridopyrimidine, a pteridine, a chromone, a thiophene, an oxadiazole, an oxatriazole, a thiadiazole, a pyranopyrrole, a furopyridine, an oxazolopyridine, a benzoisothiazole, a thienopyridine, a phenoxazine, a phenothiazine, a ruthenium complex, an europium complex, a terbium complex, a perylenediimide, a coumarin, an oxazine, an oxazole and a phthalocyanine.

4. The compound of claim 1, wherein:
$R_1$-$R_8$ are H;
$R_9$-$R_{12}$ are independently H, fluoro, an alkyl, carboxy, an acyloxymethylcarbonyl, an alkoxy, azido, an aryl or a heteroaryl;
Z is acetoxymethyl;
at least one of $R_9$-$R_{12}$ is selected from a fluorescein, a rhodamine, a bodipy, an indole, a furan, a coumarin, an oxazine, and an oxazole.

5. The compound of claim 1, wherein the compound is a fluorogenic calcium indicator of Formula 2 or 3:

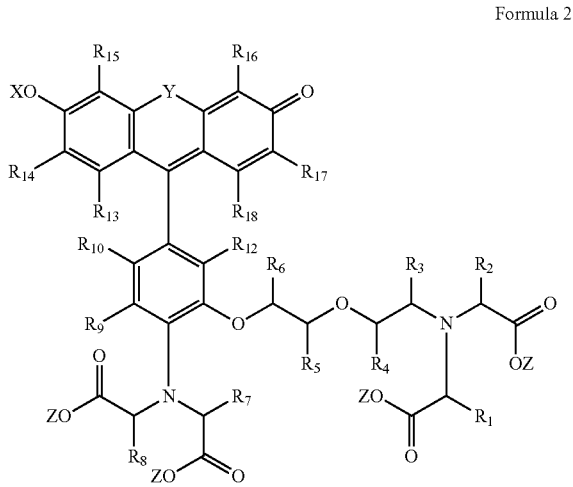

Formula 2

Formula 3

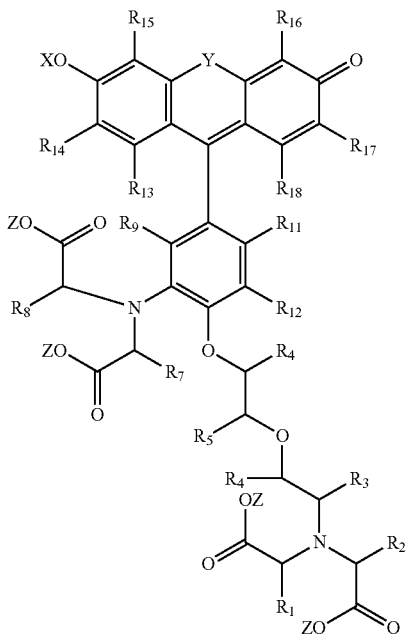

wherein:
R$_1$-R$_8$ are independently H, an alkyl, an aryl or a heteroaryl;
R$_9$-R$_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;
X and Z are independently H, a counter cation, an acyl, an acyloxymethyl, or an alkyl having 1-10 carbons; and
Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

6. The compound of claim 5, wherein:
R$_1$-R$_8$ are independently H or alkyl;
R$_9$-R$_{18}$ are independently H, an alkyl, chloro, fluoro, carboxy, an acyloxymethylcarbonyl, an alkoxy, cyano, an amino or hydroxy;
X and Z are independently H, a metal ion, an ammonium, an acyl, an acyloxymethyl, or an alkyl having 1-10 carbons; and
Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

7. The compound of claim 5, wherein:
R$_1$-R$_8$ are independently H or methyl;
R$_9$-R$_{12}$ are independently H, alkyl, chloro, fluoro, an acyloxymethylcarbonyl, an alkoxy or nitro;
R$_{13}$-R$_{18}$ are independently H, chloro or fluoro;
X and Z are independently H, a metal ion, an ammonium, an acyl, an acyoxymethyl or an alkyl having 1-10 carbons; and
Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

8. The compound of claim 5, wherein:
R$_1$-R$_8$ are H;
R$_9$-R$_{12}$ are independently H, alkyl, chloro, fluoro, an acyloxymethylcarbonyl, an alkoxy or nitro;
R$_{13}$-R$_{18}$ are independently H, chloro or fluoro;
X is acetyl or acetoxymethyl;
Y is O, O=P—R$_{25}$, R$_{25}$—C—R$_{26}$, or R$_{25}$—Si—R$_{26}$ wherein R$_{25}$ and R$_{26}$ are an alkyl; and
Z is acetoxymethyl.

9. The compound of claim 1, wherein the compound is a fluorogenic calcium indicator of Formula 4 or 5:

Formula 4

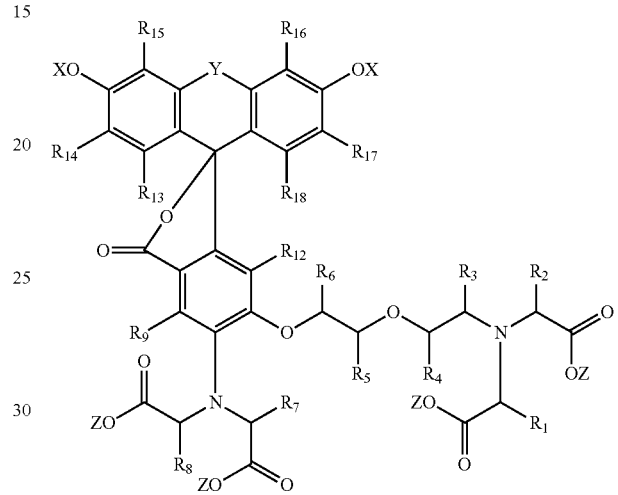

Formula 5

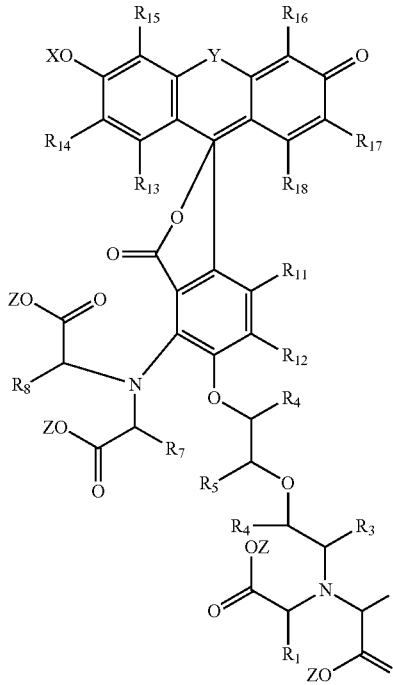

wherein:
R$_1$-R$_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

X and Z are independently an acyl or an acyloxymethyl having 1-10 carbons; and

Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl.

10. The compound of claim 9, wherein:

$R_1$-$R_8$ are independently H or alkyl;

$R_9$-$R_{18}$ are independently H, alkyl, chloro, fluoro, an alkoxy, azido, nitro, cyano, amino or hydroxy;

X is acetyl or acetoxymethyl;

Y is O, O=P—R$_{25}$, R$_{25}$—C—R$_{25}$, or R$_{25}$—Si—R$_{26}$ wherein R$_{25}$ and R$_{26}$ are an alkyl; and Z is acetoxymethyl.

11. The compound of claim 9, wherein:

$R_1$-$R_8$ are independently H or methyl:

$R_9$-$R_{12}$ are independently H, alkyl, chloro, fluoro, an alkoxy or nitro;

$R_{13}$-$R_{18}$ are independently H, chloro or fluoro;

X is acetyl or acetoxymethyl;

Y is O, O=P—R$_{25}$, R$_{25}$—C—R$_{26}$, or R$_{25}$—Si—R$_{26}$ wherein R$_{25}$ and R$_{26}$ are an alkyl; and Z is acetoxymethyl.

12. The compounds of claim 1, wherein the compound is a fluorogenic calcium indicator of Formula 6 or 7:

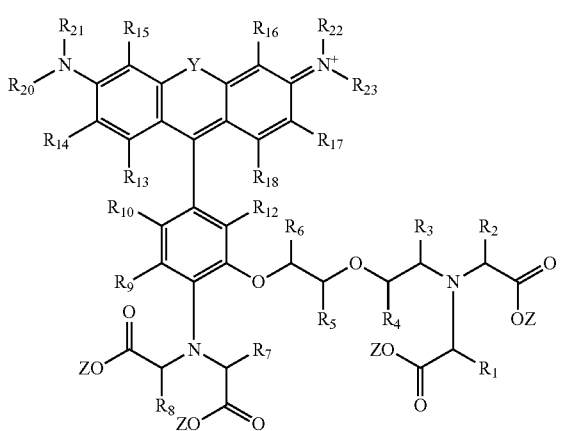

Formula 6

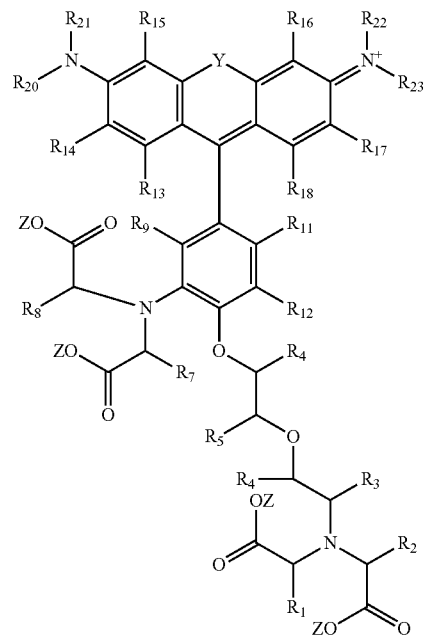

Formula 7 wherein:

$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

$R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 3-8 membered ring;

Y is O, S, S=O, O=S=O, B—OH, B(OH)$_2$, B—OR$_{25}$, R$_{25}$O—B—OR$_{26}$, Si(OH)$_2$, R$_{25}$OSiOR$_{26}$, N—R$_{25}$, P—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl; and Z is H, a counter cation, an acyl, an acyloxymethyl, or an alkyl having 1-10 carbons.

13. The compound of claim 12, wherein:

$R_1$-$R_8$ are independently H or alkyl;

$R_9$-$R_{18}$ are independently H, an alkyl, chloro, fluoro, carboxy, an acyloxymethylcarbonyl, an alkoxy, cyano, an amino or hydroxy; $R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring;

Y is O, N—R$_{25}$, O=P—R$_{25}$, R$_{25}$—C—R$_{26}$, or R$_{25}$—Si—R$_{26}$ wherein R$_{25}$ and R$_{26}$ are independently H, an alkyl, an aryl or a heteroaryl; and Z is H, a metal ion, an ammonium, an acyl, an acyloxymethyl, or an alkyl having 1-10 carbons.

14. The compound of claim 12, wherein:
$R_1$-$R_8$ are independently H or methyl;
$R_9$-$R_{12}$ are independently H, alkyl, chloro, fluoro, an acyloxymethylcarbonyl, an alkoxy or nitro;
$R_{13}$-$R_{18}$ are independently H, chloro or fluoro;
$R_{20}$-$R_{23}$ are independently H, an alkyl, or a cycloalkyl, or a heterocycle wherein $R_{20}$ and $R_{14}$, $R_{21}$ and $R_{15}$, $R_{20}$ and $R_{21}$, $R_{22}$ and $R_{16}$, $R_{23}$ and $R_{17}$, or $R_{22}$ and $R_{23}$ combine to form a 5- or 6-membered ring;
Y is O, N—$R_{25}$, O=P—$R_{25}$, $R_{25}$—C—$R_{26}$, or $R_{25}$—Si—$R_{26}$ wherein $R_{25}$ and $R_{26}$ are independently H, an alkyl, an aryl or a heteroaryl; and
Z is H, a metal ion, an ammonium, an acyl, an acyoxymethyl or an alkyl having 1-10 carbons.

15. The compound of claim 1, wherein the compound is a fluorogenic calcium indicator of Formula 8 or 9:

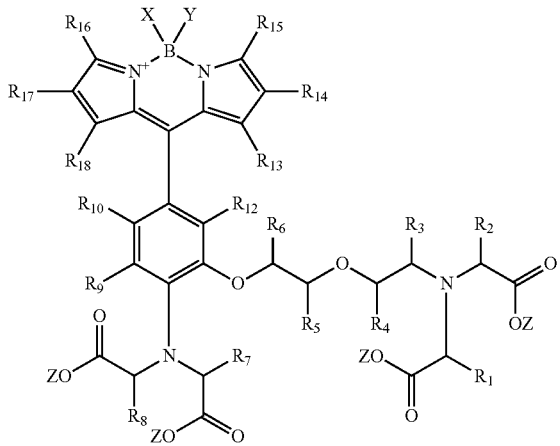

Formula 8

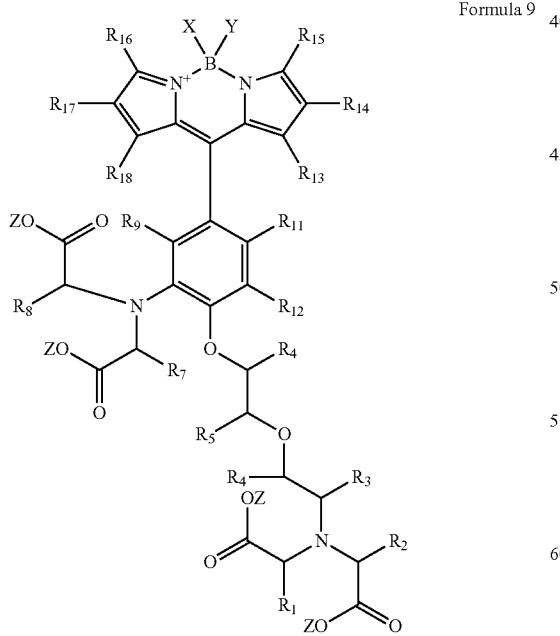

Formula 9 wherein:
$R_1$-$R_8$ are independently H, an alkyl, an aryl or a heteroaryl;

$R_9$-$R_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl; wherein $R_{13}$ and $R_{14}$, $R_{14}$ and $R_{15}$, $R_{17}$ and $R_{18}$, and/or $R_{16}$ and $R_{17}$ are optionally cyclically linked to form a 5- or 6-membered fused aromatic ring or a heteroaryl ring;
X and Y are independently F, an alkynyl, an alkoxy or an aryloxy; and
Z is H, a counter cation, an acyl, an acyloxymethyl, or an alkyl having 1-10 carbons.

16. The compound of claim 15, wherein:
$R_1$-$R_8$ are independently H or alkyl;
$R_9$-$R_{18}$ are independently H, an alkyl, chloro, fluoro, an acyloxymethylcarbonyl, an alkoxy, cyano, aryl or a heteroaryl; wherein $R_{13}$ and $R_{14}$, $R_{14}$ and $R_{15}$, $R_{17}$ and $R_{18}$, and/or $R_{16}$ and $R_{17}$ are optionally cyclically linked to form a 5- or 6-membered fused aromatic ring or a heteroaryl ring;
X and Y are independently F or an alkoxy; and
Z is an acyloxymethyl having 1-10 carbons.

17. A method of detecting intracellular calcium, the method comprising:
a) contacting a sample containing a cell with a compound according to claim 1;
b) incubating the sample for a time sufficient for the compound to be loaded into the cell and an indicator compound to be generated intracellularly;
c) illuminating the sample with incident light at a wavelength that generates a fluorescence response from the indicator compound;
d) detecting a fluorescence response from the indicator compound.

18. The method of claim 17, further comprising:
stimulating the cell;
monitoring the fluorescence response from the indicator compound to detect changes in intensity; and
correlating the changes in fluorescence intensity with changes in intracellular calcium levels.

19. The method of claim 17, wherein:
a) the compound is a cell-permeant dye indicator of Formula 2 or 3:

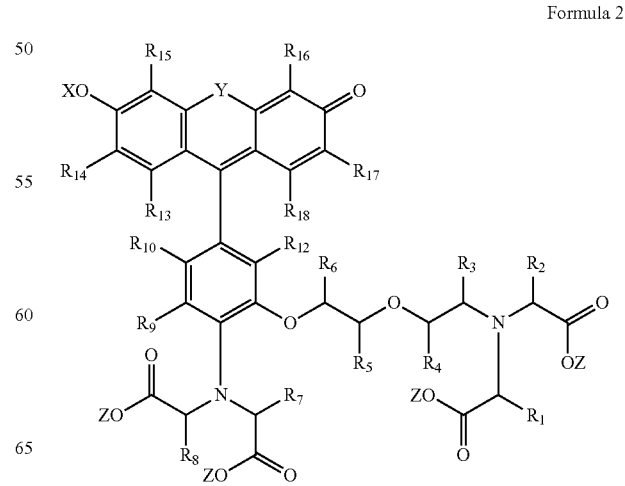

Formula 2

-continued

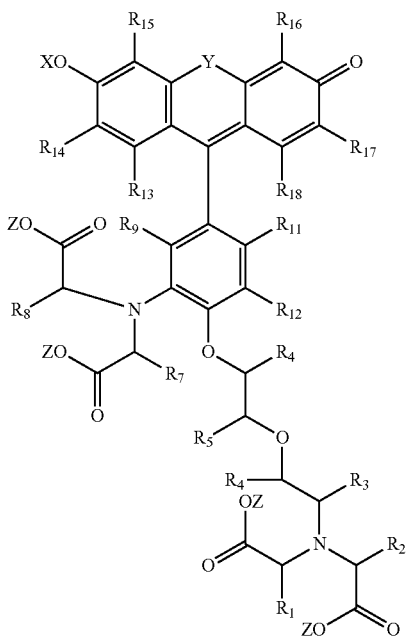

Formula 3 wherein:
R$_1$-R$_8$ are H;
R$_9$-R$_{12}$ are independently H, alkyl, chloro, fluoro, an acyloxymethylcarbonyl, an alkoxy or nitro;
R$_{13}$-R$_{18}$ are independently H, chloro or fluoro;
X is acetyl or acetoxymethyl;
Y is O, O=P—R$_{25}$, R$_{25}$—C—R$_{26}$, or R$_{25}$—Si—R$_{26}$ wherein R$_{25}$ and R$_{26}$ are an alkyl; and
Z is acetoxymethyl;
b) the compound is a cell-permeant dye indicator of Formula 4 or 5:

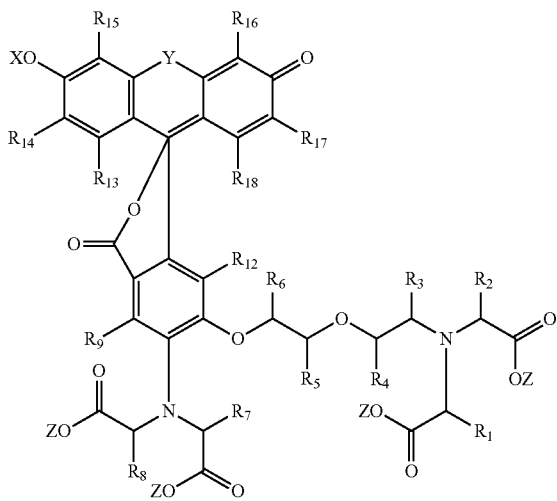

Formula 4

-continued

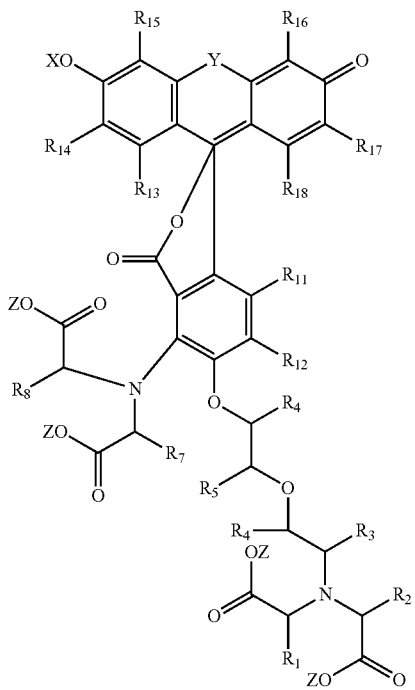

Formula 5 wherein:
R$_1$-R$_8$ are H;
R$_9$-R$_{12}$ are independently H, alkyl, chloro, fluoro, alkoxy or nitro;
R$_{13}$-R$_{18}$ are independently H, chloro or fluoro;
X is acetyl or acetoxymethyl;
Y is O, O=P—R$_{25}$, R$_{25}$—C—R$_{26}$, or R$_{25}$—Si—R$_{26}$ wherein R$_{25}$ and R$_{26}$ are methyl, ethyl, propyl or butyl; and
Z is acetoxymethyl; or
c) the compound is a cell-permeant dye indicator of Formula 8 or 9:

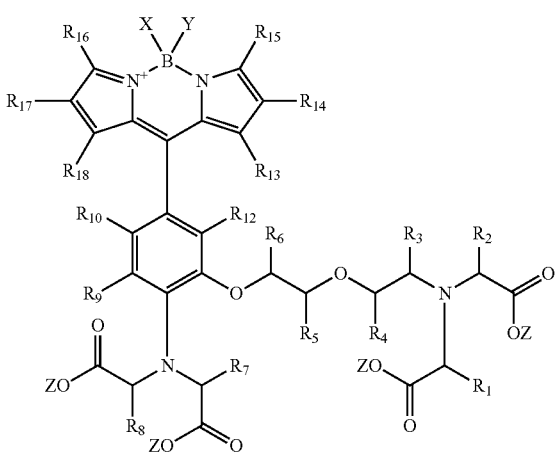

Formula 8

-continued

Formula 9

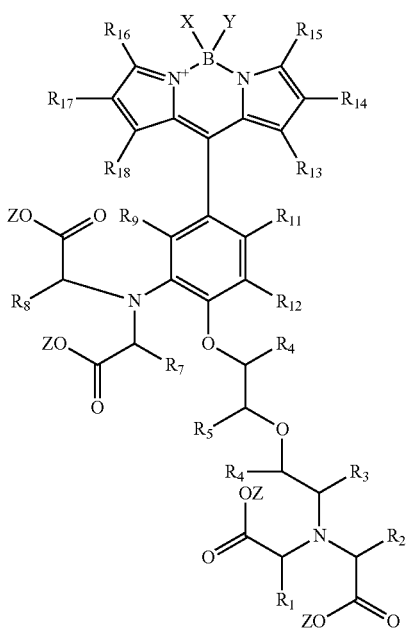

wherein:

R$_1$-R$_8$ are independently H, an alkyl, an aryl or a heteroaryl;

R$_9$-R$_{18}$ are independently H, an alkyl, a halogen, carboxy, an acyloxymethylcarbonyl, an alkoxy, an aryloxy, thiol, a alkylthiol, an arylthiol, azido, nitro, nitroso, cyano, an amino, hydroxy, a phosphonyl, a sulfonyl, a carbonyl, a boronyl, an aryl or a heteroaryl; or an alkyl, or an alkoxy that is itself optionally substituted one or more times by a halogen, an amino, hydroxy, a phosphonyl, a sulfonyl, a carbonyl, a boronyl, an aryl or a heteroaryl;

R$_{13}$ and R$_{14}$, R$_{14}$ and R$_{15}$, R$_{17}$ and R$_{18}$, and/or R$_{16}$ and R$_{17}$ are optionally cyclically linked to form a 5- or 6-membered fused aromatic ring or a heteroaryl ring;

X and Y are independently F, an alkynyl, an alkoxy or an aryloxy; and

Z is acetoxymethyl.

20. A kit for performing a calcium assay, the kit comprising:

a compound of claim 1; and an additional component selected from a calibration standard of a target ion, an ionophore, a fluorescence standard, a fluorophore, a quencher, an aqueous buffer, a surfactant and an organic solvent.

\* \* \* \* \*